United States Patent
Takeuchi et al.

(10) Patent No.: US 8,466,334 B2
(45) Date of Patent: *Jun. 18, 2013

(54) BODY FLUID ABSORBENT ARTICLE

(75) Inventors: Tomonari Takeuchi, Tochigi (JP);
Satoko Konawa, Tochigi (JP);
Tomotsugu Matsui, Ehime (JP)

(73) Assignee: Daio Paper Corporation (JP)

( * ) Notice: Subject to any disclaimer, the term of this patent is extended or adjusted under 35 U.S.C. 154(b) by 613 days.

This patent is subject to a terminal disclaimer.

(21) Appl. No.: 11/631,227

(22) PCT Filed: Jun. 30, 2005

(86) PCT No.: PCT/JP2005/012130
§ 371 (c)(1), (2), (4) Date: Jan. 3, 2008

(87) PCT Pub. No.: WO2006/004017
PCT Pub. Date: Jan. 12, 2006

(65) Prior Publication Data
US 2008/0312627 A1    Dec. 18, 2008

(30) Foreign Application Priority Data

Jun. 30, 2004 (JP) ................. 2004-194870
Jun. 30, 2004 (JP) ................. 2004-194871
Jun. 30, 2004 (JP) ................. 2004-194874
Feb. 8, 2005 (JP) ................. 2005-031662

(51) Int. Cl.
*A61F 13/15* (2006.01)

(52) U.S. Cl.
USPC .................. 604/367; 604/385.101

(58) Field of Classification Search
USPC .......... 604/367, 365, 389, 385.101, 378, 604/385.01, 354, 385.24
See application file for complete search history.

(56) References Cited

U.S. PATENT DOCUMENTS

| 4,001,565 A | 1/1977 | Kawai |
| 4,685,914 A * | 8/1987 | Holtman ................ 604/368 |
| 5,281,208 A * | 1/1994 | Thompson et al. ........... 604/378 |
| 5,382,245 A * | 1/1995 | Thompson et al. ........... 604/367 |
| 5,972,505 A * | 10/1999 | Phillips et al. ............... 428/397 |
| 6,372,954 B1 * | 4/2002 | Johnston et al. ............. 604/378 |

(Continued)

FOREIGN PATENT DOCUMENTS

| CN | 2258390 Y | 7/1997 |
| CN | 1342446 A | 4/2002 |

(Continued)

OTHER PUBLICATIONS

Supplementary European Search Report for corresponding application EP 05765331, having a completion date of Feb. 9, 2011.

*Primary Examiner* — Tatyana Zalukaeva
*Assistant Examiner* — Benedict L Hanrahan
(74) *Attorney, Agent, or Firm* — Andrus, Sceales, Starke & Sawall, LLP

(57) ABSTRACT

[Subject] To obtain a body fluid absorbent article with the perfect protection against the body fluid leakage.
[Means for Solving Problem] In the body fluid absorbent, the body fluid retainable absorbent member 53A is disposed under the face sheet 51. Then, the body fluid permeable absorbent member 52, which include the assembly of fibers in tows, is disposed between the face sheet 51 and the body fluid retainable absorbent member 53A.

27 Claims, 63 Drawing Sheets

U.S. PATENT DOCUMENTS

| | | | |
|---|---|---|---|
| 6,417,427 B1 * | 7/2002 | Roxendal et al. | 604/378 |
| 6,488,670 B1 * | 12/2002 | Schild et al. | 604/385.24 |
| 6,548,147 B1 * | 4/2003 | Raidel et al. | 428/182 |
| 6,646,180 B1 | 11/2003 | Chmielewski | |
| 6,660,902 B2 | 12/2003 | Widlund et al. | |
| 2002/0029025 A1 | 3/2002 | Furuya et al. | |
| 2003/0017776 A1 * | 1/2003 | Ohnishi et al. | 442/400 |
| 2003/0134559 A1 | 7/2003 | Delzer et al. | |
| 2004/0024375 A1 | 2/2004 | Litvay | |
| 2004/0030317 A1 * | 2/2004 | Torigoshi | 604/385.27 |
| 2004/0087927 A1 * | 5/2004 | Suzuki | 604/378 |
| 2008/0038504 A1 * | 2/2008 | Manabe et al. | 428/71 |
| 2008/0044616 A1 * | 2/2008 | Hanao et al. | 428/68 |
| 2008/0262459 A1 * | 10/2008 | Kamoto et al. | 604/375 |
| 2009/0004435 A1 * | 1/2009 | Hanao et al. | 428/156 |

FOREIGN PATENT DOCUMENTS

| | | |
|---|---|---|
| JP | H4 504285 A | 7/1992 |
| JP | H5-277147 A | 10/1993 |
| JP | 3025258 U | 3/1996 |
| JP | 9-117471 A | 5/1997 |
| JP | 9-310259 | 12/1997 |
| JP | H10 118113 A | 5/1998 |
| JP | 10-192342 A | 7/1998 |
| JP | 2001-231815 A | 8/2001 |
| JP | 2001-524350 A | 12/2001 |
| JP | 2002 65743 A | 3/2002 |
| JP | 2002-509764 A | 4/2002 |
| JP | 2002-177330 A | 6/2002 |
| JP | 2002-282304 A | 10/2002 |
| JP | 2002-291804 A | 10/2002 |
| JP | 2003-33397 A | 2/2003 |
| JP | 2003-70820 A | 3/2003 |
| JP | 2003 144489 A | 5/2003 |
| JP | 2003-190210 A | 7/2003 |
| JP | 2004-41339 A | 2/2004 |
| JP | 2004-121382 | 4/2004 |
| WO | WO-83/03267 | 9/1983 |
| WO | 93/02235 A1 | 2/1993 |
| WO | 99/27876 A1 | 6/1999 |
| WO | 99/27879 A2 | 6/1999 |
| WO | WO-99/27876 | 6/1999 |
| WO | 99/49826 A1 | 10/1999 |
| WO | 01/17475 A1 | 3/2001 |
| WO | 02/091975 A1 | 11/2002 |
| WO | 2004/017883 A1 | 3/2004 |

* cited by examiner

FIG. 21
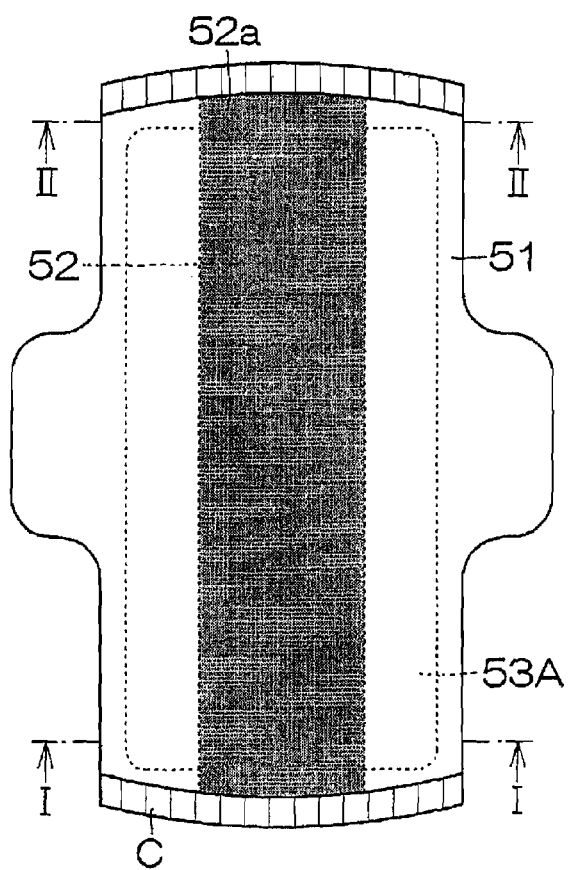
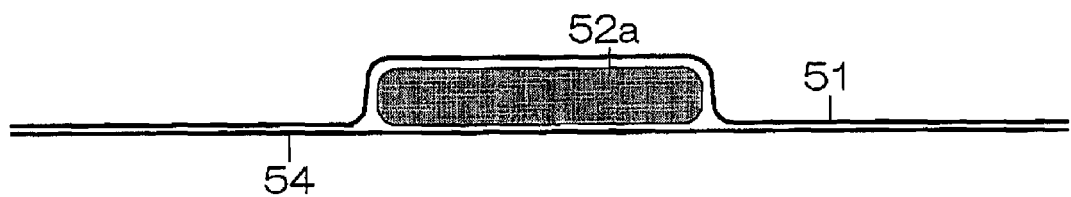
FIG. 22

BODY FLUID ABSORBENT ARTICLE

TECHNICAL FIELD

The invention relates to body fluid absorbent articles such as disposable diapers, sanitary napkins, urine pads, incontinence pads or the like.

BACKGROUND ART

Each body fluid absorbent article such as a disposable diaper, a sanitary napkin, a urine pad, an incontinence pad or the like has generally a body fluid absorbent structure provided with a face sheet and a body fluid retainable absorbent member disposed under the face sheet. Such body fluid retainable absorbent member has been conventionally made of pulp e.g. flocculent pulp or synthetic pulp or fluff pulp, into which absorbent polymer is mixed in the form of e.g., particles. The absorbent member fabricated like this absorbs the body fluid with the rather low speed. Thus, before the body fluid is completely absorbed into the absorbent member, the body fluid is moved to reach the ends or edges of the article, which might cause the body fluid leakage at the ends or edges of the article.

To cope with it, in these days, a non-woven sheet is disposed between the face sheet and the body fluid retainable absorbent member (See, for example, Patent Citation 1). The non-woven sheet has the function to absorb the body fluid quickly in order to prevent the body fluid from moving to reach the ends or edges of the article.

However, since the non-woven sheet has the small absorbing capacity for the body fluid, there are remained the following problems in the body fluid absorbent structure including the non-woven sheet disposed like this.

The body fluid is absorbed into and then passed through the non-woven sheet as it is. Subsequently, the body fluid is absorbed into the body fluid retainable absorbent member. As stated above, although the body fluid is absorbed into the non-woven sheet quickly, after that they are absorbed into the body fluid retainable absorbent member with the low speed. Accordingly, as for the permeability of the body fluid through the non-woven sheet, in figurative saying, the sheet has a wide inlet and a narrow outlet. Such configuration leads the body fluid to the deadlock in the non-woven sheet. In this way, when the large amount of body fluid should be absorbed, for example, when the body fluid is continuously discharged and should be absorbed, the over-flow situation cannot be avoided in the non-woven sheet due to its small absorbing capacity. As a result, it is impossible to prevent perfectly the body fluid from moving to reach the ends or edges of the article, which might cause leakage.

[Patent Citation 1] published Japanese translation of PCT international publication WO 99/27876 for Japanese patent application No. 2001-524399, the PCT published application being in the English language.

DISCLOSURE OF INVENTION

Problem to be Solved by the Invention

The main problem to be solved by the present invention is to provide a body fluid absorbent article offering perfect protection against the leakage of the body fluid.

Means for Solving Problem

The present invention solving this problem is stated in the following.

[Invention Claimed in Claim 1]
A body fluid absorbent article having a body fluid absorbent structure with a body fluid retainable absorbent member disposed under a face sheet, comprising a body fluid permeable absorbent member, which is interposed between the above face sheet and the above body fluid retainable absorbent member, and which includes an assembly of fibers in tows.

[Invention Claimed in Claim 2]
A body fluid absorbent article as defined in Claim 1, wherein the above body fluid retainable absorbent member is formed with an absorbent member obtained by moving absorbent polymer into an assembly of fibers in tows.

[Invention Claimed in Claim 3]
A body fluid absorbent article as defined in Claim 1 or 2, wherein binder is added to the above assembly of fibers in tows in at least one of the above body fluid retainable absorbent member and the above body fluid permeable absorbent member.

[Invention Claimed in Claim 4]
A body fluid absorbent article as defined in Claim 3, wherein by adding the above binder, contacting portions of the above fibers are adhered or fused in the form of at least one of line and dot.

[Invention Claimed in Claim 5]
A body fluid absorbent article as defined in Claim 4, wherein the above assembly of fibers in tows comprises at least two zones being different in adhesion degree or fusion degree of the fibers by adjusting the added amount of binder.

[Invention Claimed in Claim 6]
A body fluid absorbent article as defined in Claim 5, wherein, in the above assembly of fibers in tows, the adhesion degree or fusion degree of the fibers at a middle portion in the width direction is stronger than the adhesion degree or fusion degree of the fibers at both side portions in the width direction by adjusting the added amount of binder to the above middle portion so as to be larger than the added amount of binder to the above both side portions.

[Invention Claimed in Claim 7]
A body fluid absorbent article as defined in Claim 5, wherein, in the above assembly of fibers in tows, the adhesion degrees or fusion degrees of the fibers at both side portions in the width direction are stronger than the adhesion degree or fusion degree of the fibers at a middle portion in the width direction by adjusting the added amount of binder to the above both side portions so as to be larger than the added amount of binder to the above middle portion.

[Invention Claimed in Claim 8]
A body fluid absorbent article as defined in Claim 5, wherein, in the above assembly of fibers in tows, the adhesion degrees or fusion degrees of the fibers at a portion near a top face and at a portion near a bottom face are stronger than the adhesion degree or fusion degree of the fibers at an intermediate portion between the top face and the bottom face by adjusting the added amount of binder to the above portion near the top face and to the above portion near the bottom face so as to be larger than the added amount of binder to the above intermediate portion.

[Invention Claimed in Claim 9]
A body fluid absorbent article as defined in Claim 5, wherein, in the above assembly of fibers in tows, the adhesion degrees or fusion degrees of the fibers at a portion near a top face and at a portion near a bottom face and at both side end portions on the cross section in the width direction are stronger than the adhesion degree or fusion degree of the fibers at a central portion by adjusting the added amount of binder to the above portion near the top face and to the above portion near the bottom face and to the above both side end portions so as to be larger than the added amount of binder to the above central portion.

[Invention Claimed in Claim 10]

A body fluid absorbent article as defined in Claim 5, wherein, in the above assembly of fibers in tows, the adhesion degrees or fusion degrees of the fibers at both side end portions on the cross section in the width direction are stronger than the adhesion degree or fusion degree of the fibers at an intermediate portion on the cross section in the width direction by adjusting the added amount of binder to the above both side end portions so as to be larger than the added amount of binder to the above midway portion.

[Invention Claimed in Claim 11]

A body fluid absorbent article as defined in Claim 5, wherein, in the above assembly of fibers in tows, the adhesion degree or fusion degree of the fibers at an intermediate portion on the cross section in the width direction is stronger than the adhesion degrees or fusion degrees of the fibers at both side end portions on the cross section in the width direction by adjusting the added amount of binder to the above midway portion so as to be larger than the added amount of binder to the above both side end portions.

[Invention Claimed in Claim 12]

A body fluid absorbent article as defined in any one of Claims 1 to 11, wherein an absorbent member made of an absorbent material other than the tow is laminated on the under surface of the above body fluid retainable absorbent member.

[Invention Claimed in Claim 13]

A body fluid absorbent article as defined in Claim 12, wherein the above absorbent material other than the tow comprises at least one of a pulp fiber, porous foam, a cotton fiber and a non-woven fabric.

[Invention Claimed in Claim 14]

A body fluid absorbent article as defined in Claim 12 or 13, wherein embossing is carried out on the above absorbent member made of the above absorbent material other than the tow.

[Invention Claimed in Claim 15]

A body fluid absorbent article as defined in any one of Claims 1 to 14, wherein the above body fluid retainable absorbent member has the compressive resilience RC of 40 to 60%.

[Invention Claimed in Claim 16]

A body fluid absorbent article as defined in any one of Claims 1 to 15, wherein the above body fluid retainable absorbent member has the work of compression WC of 4.0 to 10.0 gf·cm/cm².

[Invention Claimed in Claim 17]

A body fluid absorbent article as defined in any one of Claims 1 to 16, wherein the above body fluid retainable absorbent member has the tow fiber density of 0.03 to 0.25 g/cm³.

[Invention Claimed in Claim 18]

A body fluid absorbent article as defined in any one of Claims 1 to 17, wherein the above body fluid retainable absorbent member has the basis weight of 30 to 300 g/m².

[Invention Claimed in Claim 19]

A body fluid absorbent article as defined in any one of Claims 1 to 18, wherein the above body fluid retainable absorbent member has the mass of 1 to 15 g.

[Invention Claimed in Claim 20]

A body fluid absorbent article as defined in any one of Claims 1 to 19, wherein the above body fluid permeable absorbent member has the porosity of 60 to 85%.

[Invention Claimed in Claim 21]

A body fluid absorbent article as defined in any one of Claims 1 to 20, wherein the above body fluid permeable absorbent member is interposed, between the above face sheet and the middle portion in the width direction of the above body fluid retainable absorbent member, along its longitudinal direction and pressing is carried out along the longitudinal direction on portions on the both sides of said body fluid permeable absorbent member, the portions where said body fluid permeable absorbent member is not interposed.

[Invention Claimed in Claim 22]

A body fluid absorbent article as defined in any one of Claims 1 to 20, wherein the above body fluid permeable absorbent member is interposed in the width direction, between the above face sheet and the intermediate portion in the longitudinal direction of the above body fluid retainable absorbent member and pressing is carried out along the width direction of said body fluid retainable absorbent member on portions in front and back of said body fluid permeable absorbent member, the portions where said body fluid permeable absorbent member is not interposed.

[Invention Claimed in Claim 23]

A body fluid absorbent article as defined in any one of Claims 1 to 22, wherein a body fluid diffusion sheet is interposed between the above body fluid retainable absorbent member and the above body fluid permeable absorbent member.

[Invention Claimed in Claim 24]

A body fluid absorbent article as defined in Claim 23, wherein pressing is carried out on said body fluid diffusion sheet along at least the longitudinal direction of said body fluid retainable absorbent member.

[Invention Claimed in Claim 25]

A body fluid absorbent article as defined in any one of Claims 1 to 24, wherein a body fluid permeable absorbent sheet is interposed between the above face sheet and the above absorbent member including the above assembly of fibers in tows.

[Invention Claimed in Claim 26]

A body fluid absorbent article as defined in any one of Claims 1 to 25, wherein the constituent fiber of the above assembly of fibers in tows is cellulose acetate.

[Invention Claimed in Claim 27]

A body fluid absorbent article as defined in any one of Claims 1 to 26, wherein the constituent fiber of the above assembly of fibers in tows has the cross section of a circle or an ellipse.

[Invention Claimed in Claim 28]

A body fluid absorbent article as defined in any one of Claims 1 to 27, wherein pressing is carried out on the above body fluid retainable absorbent member so as to extend in at least its longitudinal direction.

[Invention Claimed in Claim 29]

A body fluid absorbent article as defined in any one of Claims 1 to 28, wherein the above body fluid retainable absorbent member is wrapped with a covering sheet.

[Invention Claimed in Claim 30]

A body fluid absorbent article as defined in Claim 29, wherein the above covering sheet is tissue paper.

[Invention Claimed in Claim 31]

A body fluid absorbent article as defined in Claim 29, wherein the above covering sheet is a non-woven fabric.

[Invention Claimed in Claim 32]

A body fluid absorbent article as defined in any one of Claims 1 to 31, wherein a holding sheet is provided on the back surface side of said body fluid retainable absorbent member.

[Invention Claimed in Claim 33]

A body fluid absorbent article as defined in Claim 32, wherein the above holding sheet is a non-woven fabric having the work of compression of 0.01 to 10.00 gf·cm/cm$^2$ and the compressive resilience of 10 to 100% based on KES test.

[Invention Claimed in Claim 34]

A body fluid absorbent article as defined in any one of Claims 1 to 33, wherein the above body fluid retainable absorbent member has the thickness of 0.1 to 1 cm.

Effect of the Invention

In accordance with the present invention, a perfect protection effect against the leakage of the body fluid can be offered.

BRIEF DESCRIPTION OF THE DRAWINGS

FIG. 21 is a plan view of a body fluid absorbent article according to the second example.

FIG. 22 is a cross section taken on line II-II of FIG. 21.

BEST MODE FOR CARRYING OUT THE INVENTION

Now, the embodiments of the present invention will be explained.

[Application]

The body fluid absorbent structure in accordance with the present invention can be applied to general body fluid absorbent articles each of which absorbs urine, menstrual blood and the like. As the body fluid absorbent article of this kind, there can be listed, for example, a disposable diaper, a sanitary napkin, a urine pad, an incontinence pad and the like.

[Body Fluid Absorbent Structure]

The First Embodiment

Figure 1:
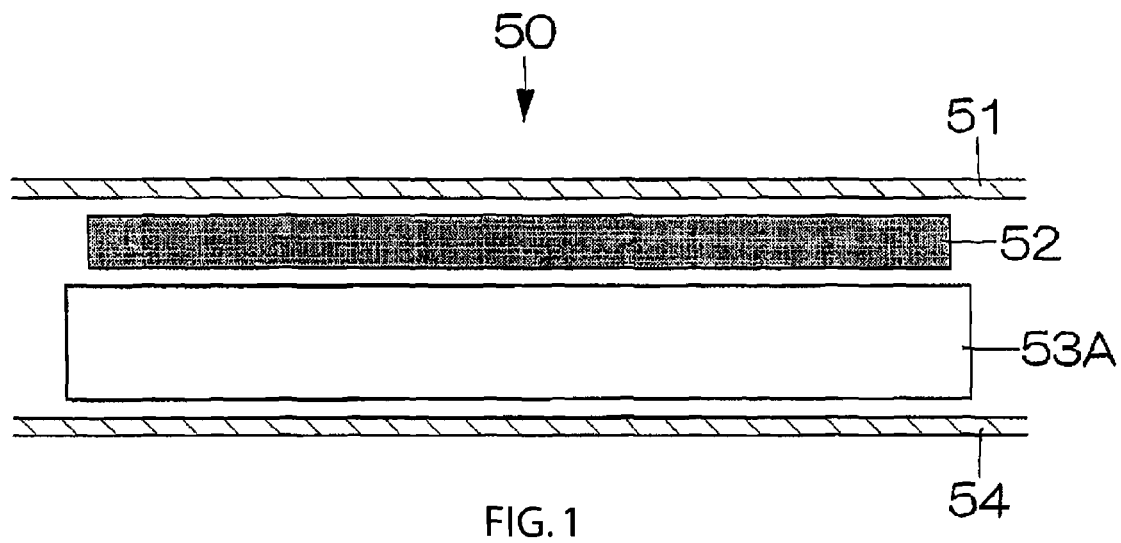
FIG. 1 is a cross section of a body fluid absorbent structure according to the first embodiment.

As shown in FIG. 1, the body fluid absorbent structure 50 of the first embodiment is provided with the body fluid retainable absorbent member 53A, which is disposed under the face (top) sheet 51 located at the wearer-side of the structure 50. Then, the body fluid permeable absorbent member 52, which includes an assembly of fibers in tows, is interposed between the face sheet 51 and the body fluid retainable absorbent member 53A, instead of a non-woven sheet, which was conventionally interposed between them. Since the absorbing capacity of the assembly of fibers in tows is much larger than that of the non-woven sheet, even if the large amount of body fluid is absorbed, for example, when the body fluid is continuously discharged and absorbed, the over-flow situation can be avoided. Accordingly, the body fluid can be prevented completely from moving to reach the ends or edges of the article. Therefore, the body fluid absorbent structure 50 offers a perfect protection effect against the leakage of the body fluid.

In this body fluid absorbent structure 50, the under surface of the body fluid retainable absorbent member 53A is covered with, for example, the body fluid non-permeable back sheet 54. This back sheet 54 provides protection against the leakage of the body fluid at the under surface of the article.

The Second Embodiment

Figure 2:
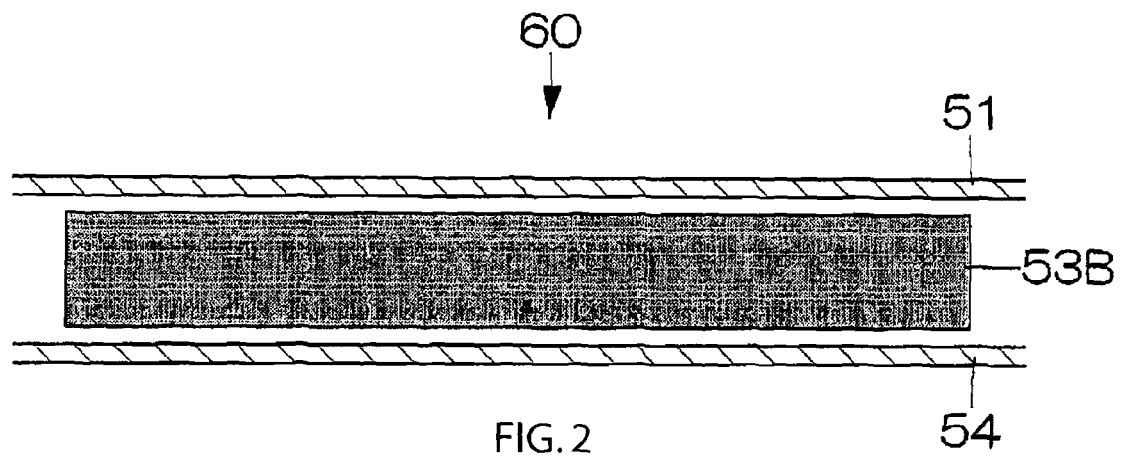
FIG. 2 is a cross section of a body fluid absorbent structure according to the second embodiment.

As shown in FIG. 2, the body fluid absorbent structure 60 of the second embodiment is provided with the body fluid retainable absorbent member 53B, which is disposed under the face sheet 51 located at the wearer-side of the structure 60. Then, the body fluid retainable absorbent member 53B is formed with an absorbent member obtained by moving absorbent polymer into an assembly of fibers in tows. This absorbent member obtained by moving the absorbent polymer into the assembly of fibers in tows absorbs the body fluid at the high speed and at the same time has the remarkably large absorbing capacity for the body fluid. Accordingly, even if the large amount of body fluid should be absorbed, for example, when the body fluid is continuously discharged and absorbed, the over-flow situation can be avoided. Thus, the body fluid can be prevented completely from moving to reach the ends or edges of the article. Therefore, this body fluid absorbent structure 60 also offers perfect protection against the leakage of the body fluid in the same manner as, in the first embodiment, so does the body fluid absorbent structure 50, which is provided with the body fluid permeable absorbent member 52 and the body fluid retainable absorbent member 53A.

The Third Embodiment

Figure 3:
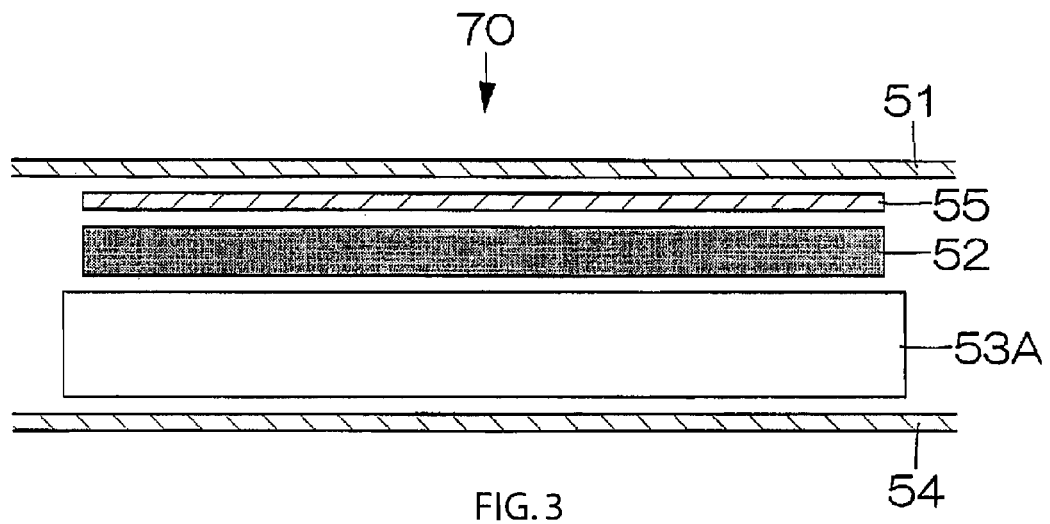
FIG. 3 is a cross section of a body fluid absorbent structure according to the third embodiment.

As shown in FIG. 3, the body fluid absorbent structure 70 of the third embodiment is application of the body fluid absorbent structure 50 according to the first embodiment. In this body fluid absorbent structure 70, the body fluid permeable absorbent sheet 55 is interposed between the face sheet 51 and the absorbent member including an assembly of fibers in tows, namely the body fluid permeable absorbent member 52. In this body fluid absorbent structure 70, the body fluid permeable absorbent member 52, which is disposed under the absorbent sheet 55, includes the assembly of fibers in tows, and so the body fluid permeable absorbent member 52 absorbs the body fluid with the remarkably high speed. That is to say, as for the body fluid permeability, the absorbent sheet 55, in figurative saying, has a wide inlet and a wide outlet. Accordingly, the body fluid permeates (is passed) quickly through the absorbent sheet 55. Therefore, even after the absorbent sheet 55 once absorbs the body fluid, it will dry quickly. As a result, since the body fluid is prevented from reversing through the face sheet 51, the comfortable feeling of the article can be ensured. Further, it is needless to say that the absorbent sheet 55 gives another advantage of increasing the absorbing capacity of the whole body fluid permeable member (in this embodiment, the absorbent member 52 and the absorbent sheet 55).

The Fourth Embodiment

Figure 4:
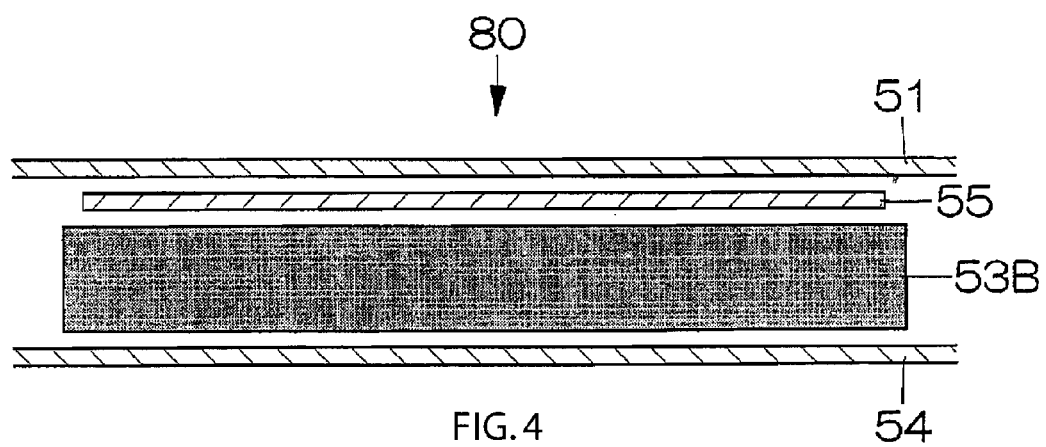
FIG. 4 is a cross section of a body fluid absorbent structure according to the fourth embodiment.

As shown in FIG. 4, the body fluid absorbent structure 80 of the fourth embodiment is application of the body fluid absorbent structure 60 according to the second embodiment on the basis of viewpoint used in the third embodiment. In this body fluid absorbent structure 80, the body fluid permeable absorbent sheet 55 is interposed between the face sheet 51 and the absorbent member including an assembly of fibers in tows, namely the body fluid retainable absorbent member 53B. In this body fluid absorbent structure 80, the body fluid retainable absorbent member 53B, which is disposed under the absorbent sheet 55, includes the assembly of fibers in tows. Thus, the body fluid retainable absorbent member 53B absorbs the body fluid with the remarkably high speed. That is to say, as for the permeability of the body fluid, the absorbent sheet 55 functions in the same manner as the absorbent sheet of the third embodiment does. Accordingly, the body fluid permeates (is passed) quickly through the absorbent sheet 55. Therefore, even after the absorbent sheet 55 once absorbs the body fluid, it will dry quickly. As a result, since the body fluid is prevented from reversing through the face sheet 51, the comfortable feeling of the article can be ensured. Further, it is needless to say that also in this embodiment, the absorbent sheet 55 gives another advantage of increasing the absorbing capacity.

The Fifth Embodiment

Figure 5:
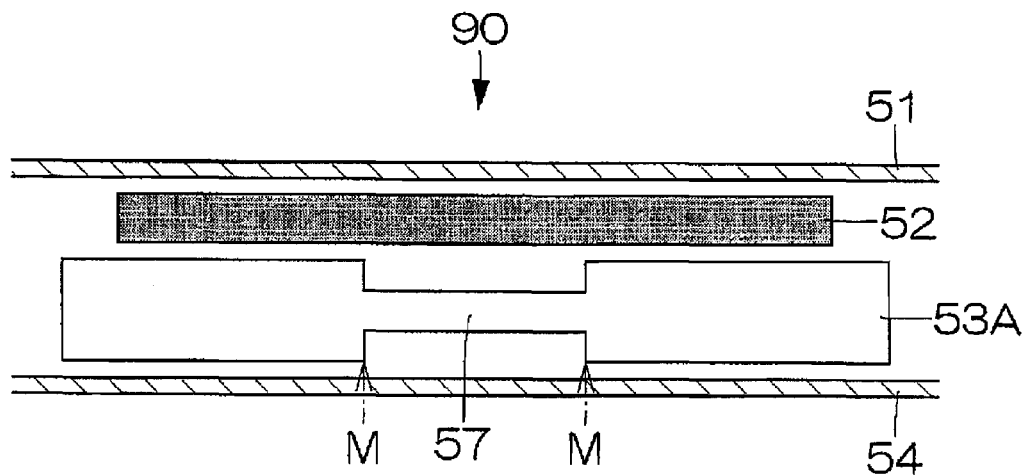
FIG. 5 is a cross section of a body fluid absorbent structure according to the fifth embodiment.

As shown in FIG. 5, the body fluid absorbent structure 90 of the fifth embodiment comprises the body fluid retainable absorbent member 53A, which is disposed under the face sheet 51 located at the wearer-side. Then, the body fluid permeable absorbent member 52, which includes an assembly of fibers in tows, is interposed between the face sheet 51 and the body fluid retainable absorbent member 53A, instead of a non-woven sheet, which was conventionally interposed between them. Since the absorbing capacity of the assembly of fibers in tows is much larger than that of the non-woven sheet, even if the large amount of body fluid should be absorbed, for example, when the body fluid is continuously discharged and absorbed, the over-flow situation can be avoided.

Additionally, in this body fluid absorbent structure 90, pressing e.g., embossing is carried out at least longitudinally on the body fluid retainable absorbent member 53A. Due to this pressing, the body fluid is diffused quickly along a pressed portion (high density portion) 57, which is formed by such pressing. This enables to enlarge the body fluid absorbing zone of the body fluid retainable absorbent member 53A. That is to say, as for the permeability of the body fluid, the body fluid permeable absorbent member 52, in figurative saying, has a wide inlet and a wide outlet. Consequently, it is ensured that the over-flow situation is avoided. Accordingly, in this body fluid absorbent structure 90, the body fluid can be prevented completely from moving to reach the ends or edges of the article, leading to the remarkable protection against the leakage of the body fluid.

Further, as for the permeability of the body fluid, the body fluid permeable absorbent member 52, in figurative saying, has a wide inlet and a wide outlet. Thus, the body fluid permeates (is passed) quickly through the absorbent member 52. Therefore, even after the body fluid permeable absorbent member 52 once absorbs the body fluid, it will dry quickly. As a result, since the body fluid is prevented from reversing through the face sheet 51, the comfortable feeling of the article can be ensured.

Figure 6:
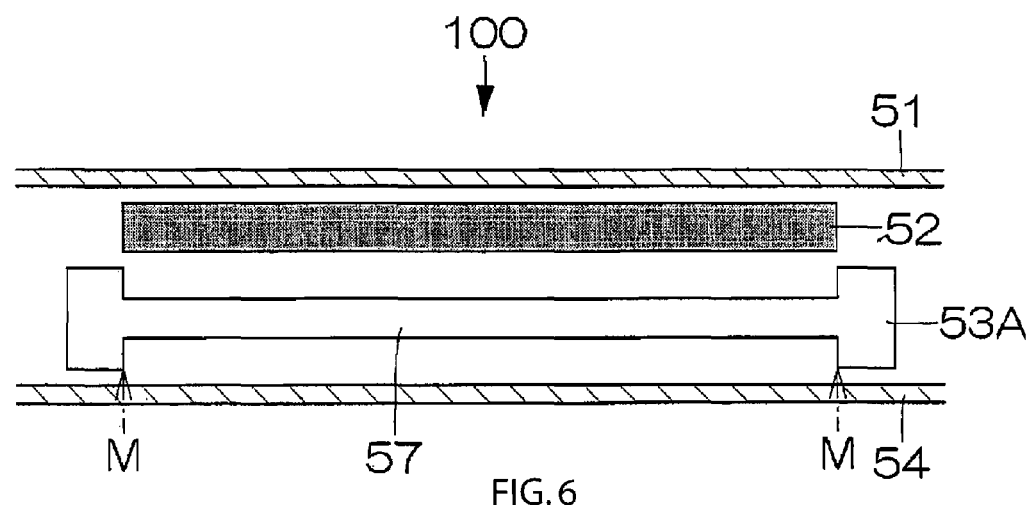
FIG. 6 is a cross section of a body fluid absorbent structure according to the fifth embodiment.

In this embodiment, the pressed portion 57 is extended along the longitudinal direction. For example, when this body fluid absorbent structure 90 is applied to an absorbent article such as a disposable diaper, a sanitary napkin, or the like, the pressed portion is formed so as to extend between the front end-side and the back end-side of the article while the both side edges M, M of the pressed portion correspond to the side edges of the middle portion of the body fluid permeable absorbent member 52 in the width direction. However, the configuration of the pressed portion is not restricted to such situation. For example, as the body fluid absorbent structure 100 shown in FIG. 6, the pressed portion 57 can be formed so that its both side edges M, M correspond to the both side edges of the body fluid permeable absorbent member 52. That is to say, the width of the pressed portion can be changed desirably.

The number of pressed portion 57 is not limited specifically. For example, as indicated in this embodiment, the pressed portion can be formed in one line. Not restricted to one line, two lines, three lines, four lines, or more are possible.

The pressed portion 57, in this embodiment, is preferably extended at least along the longitudinal direction, in other words, extended in the direction crossing to the width direction of the body fluid retainable absorbent member 53A. This is because the increase of body fluid diffusion in the longitudinal direction contributes to enlarge the body fluid absorbing zone in the body fluid retainable absorbent member 53A. Accordingly, angle made by the pressed portion 57 crossing to the width direction of the absorbent member 53A is not limited specifically but can be designed desirably from the above viewpoint. As the way of forming the pressed portion 57 other than above ways, embossing can be listed in the same manner as shown in Japanese Unexamined Patent Application Publication No. 2004-121382.

In this body fluid absorbent structure 90, the under surface of the body fluid retainable absorbent member 53A is covered with, for example, a body fluid non-permeable back sheet 54. This back sheet 54 provides protection against the leakage of the body fluid at the under surface of the article.

The Sixth Embodiment

Figure 7:
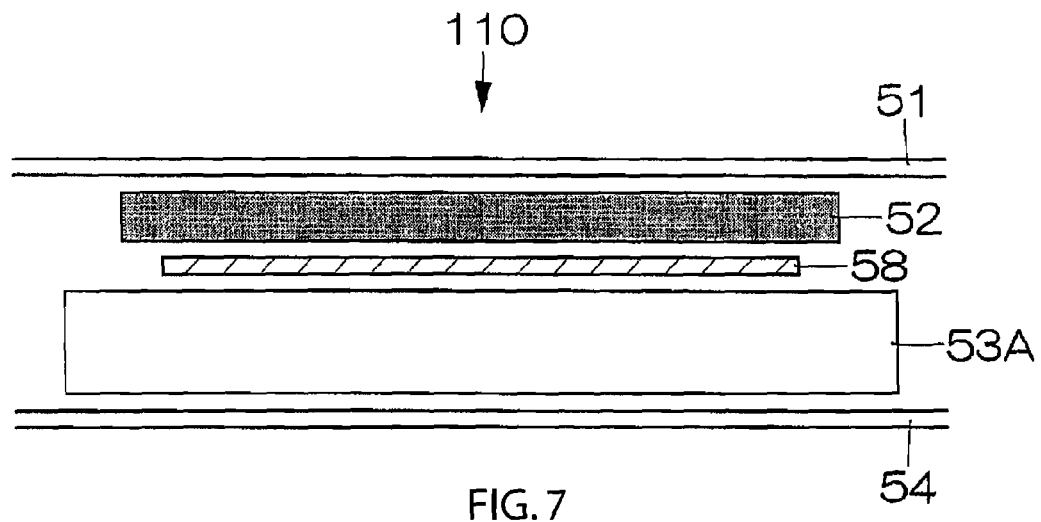
FIG. 7 is a cross section of a body fluid absorbent structure according to the sixth embodiment.

As shown in FIG. 7, the body fluid absorbent structure 110 of the sixth embodiment is the modification of the body fluid absorbent structure 90, 100 according to the fifth embodiment. In this body fluid absorbent structure 110, the pressed portion is not formed on the body fluid retainable absorbent member 53A, but the body fluid diffusion sheet 58 is interposed between the body fluid retainable absorbent member 53A and the body fluid permeable absorbent member 52 instead. The body fluid, after permeating through the face sheet 51 and the body fluid permeable absorbent member 52, is diffused quickly in the body fluid diffusion sheet 58. Accordingly, the body fluid can be absorbed into the enlarged zone of the body fluid retainable absorbent member 53A, which leads to the same effect as the pressed portion 57. Therefore, it is preferable that the body fluid diffusion sheet 58 is extended at least along the longitudinal direction.

Additionally, according to this embodiment, since the body fluid diffusion sheet 58 is disposed under the face sheet 51 and the body fluid permeable absorbent member 52, the body fluid is diffused at places where the wearer cannot see directly. Therefore, the wearer does not feel the body fluid diffused widely, which brings some relief to the wearer.

The Seventh Embodiment

Figure 8:
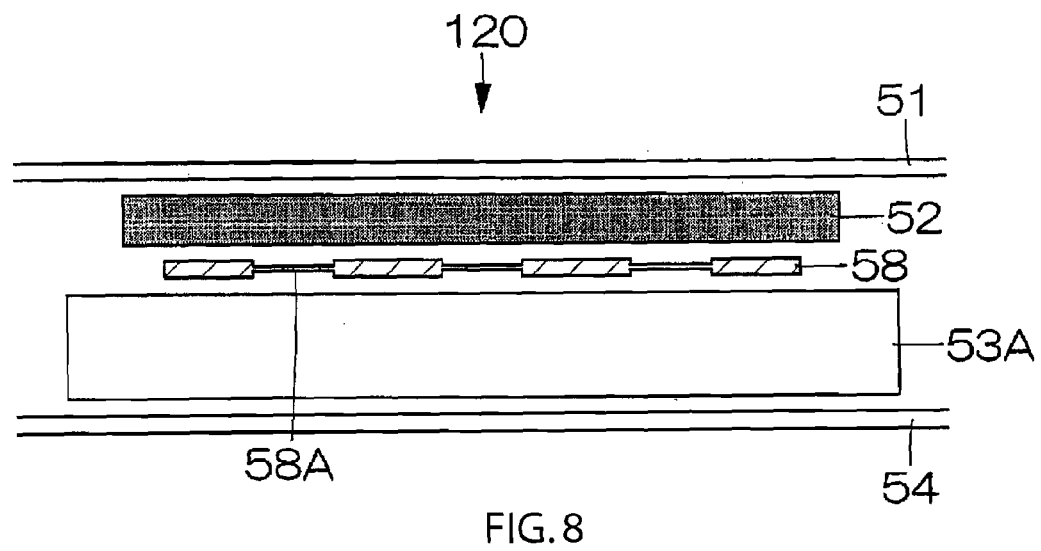
FIG. 8 is a cross section of a body fluid absorbent structure according to the seventh embodiment.

As shown in FIG. 8, the body fluid absorbent structure 120 of the seventh embodiment is the modification of the body fluid absorbent structure 110 according to the sixth embodiment. In this body fluid absorbent structure 120, pressing e.g., embossing is carried out on the body fluid diffusion sheet 58 at least along its longitudinal direction. Due to this pressing, the body fluid is diffused quickly along the resultant pressed portions (high density portions) 58A, 58A . . . . In the fifth embodiment, the pressed portion 57 is extended on the body fluid retainable absorbent member 53A at least along its longitudinal direction, because the increase of body fluid diffusion in the longitudinal direction contributes to enlarge the body fluid absorbing zone in the body fluid retainable absorbent member 53A. Also in this body fluid absorbent structure 120, from the same reason, the pressed portions 58A, 58A . . . are configured.

The method for forming these pressed portions 58A, 58A . . . is not limited specifically and there are similar methods to those stated in the case of pressed portion 57 in the body fluid retainable absorbent member 53A.

The Eighth Embodiment

Figure 9:
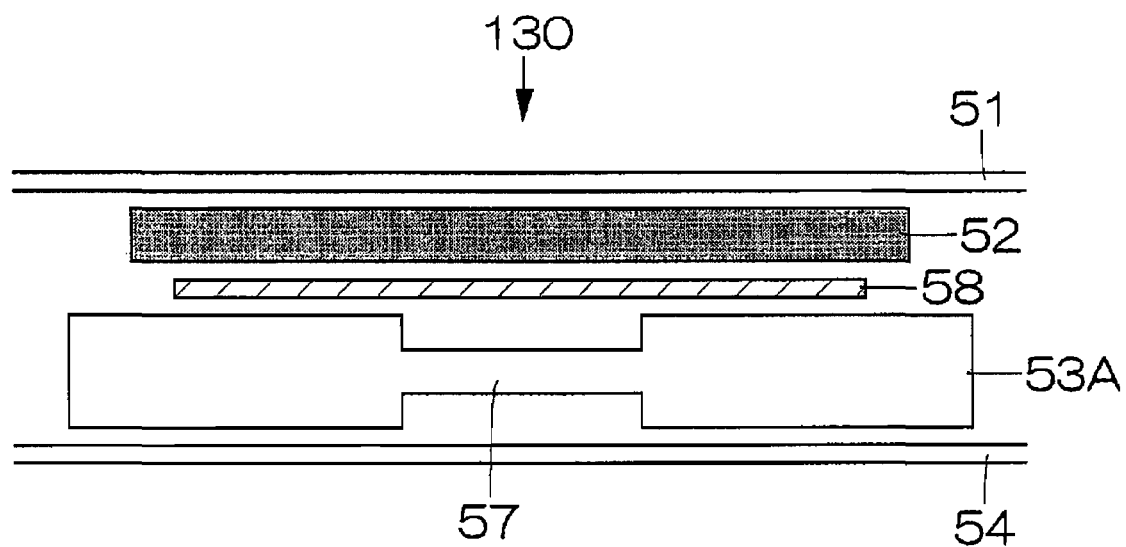
FIG. 9 is a cross section of a body fluid absorbent structure according to the eighth embodiment.

As shown in FIG. 9, the body fluid absorbent structure 130 of the eighth embodiment is the combination of the body fluid absorbent structure 90, 100 according to the fifth embodiment and the body fluid absorbent structure 110 according to the sixth embodiment. In this body fluid absorbent structure 130, pressing e.g., embossing is carried out on the body fluid retainable absorbent member 53A, at least along its longitudinal direction. Then, at the same time the body fluid diffusion sheet 58 is interposed between the body fluid retainable absorbent member 53A and the body fluid permeable absorbent member 52. Accordingly, body fluid diffusion can be improved by the synergic effect, which facilitates the body fluid absorption into the larger zone of the body fluid retainable absorbent member 53A. Therefore, the body fluid is prevented completely from moving to reach the ends or edges of the article, which leads to the remarkably high effect of protection against the leakage of body fluid.

Other Embodiments

In the above first to eighth embodiments, it is not described specifically about what zone each body fluid permeable absorbent member 52 is disposed. That is to say, such zone is not intended to limit. Like the conventional non-woven sheets, the body fluid permeable absorbent member 52 is disposed under the face sheet 51 so as to extend totally over its under surface or so as to extend partly over its under surface, both of which are possible.

Figure 12:
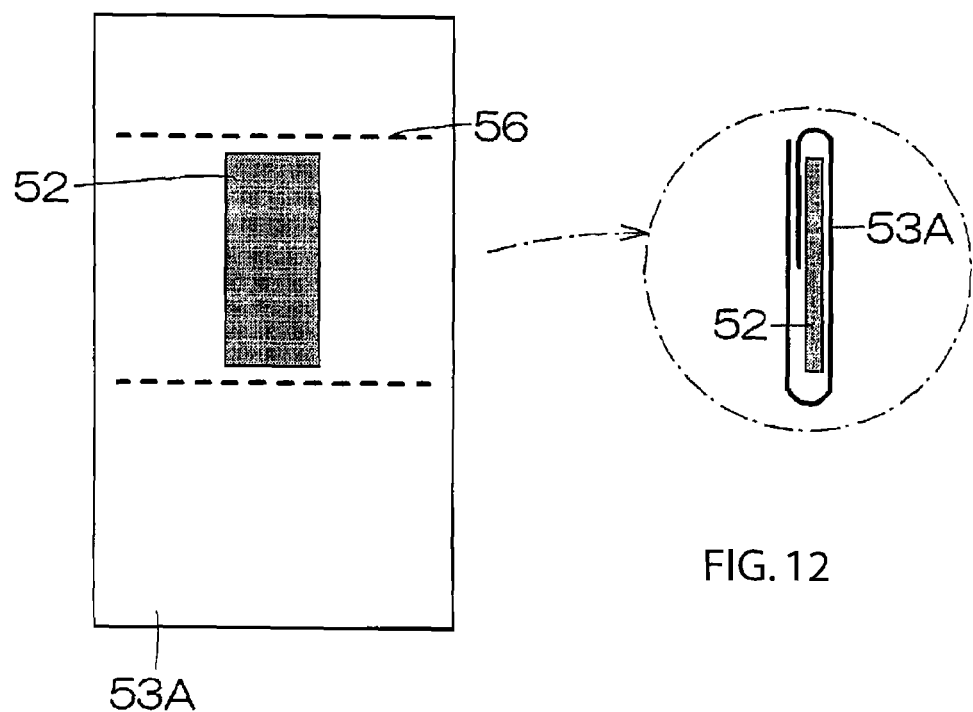
FIG. 12 is a plan view of a body fluid absorbent structure according to another embodiment.
Figure 13:
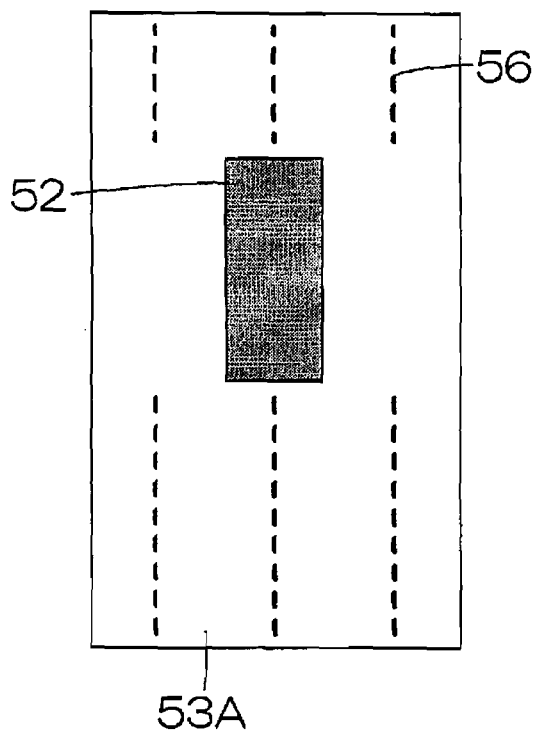
FIG. 13 is a plan view of a body fluid absorbent structure according to another embodiment.
Figure 14:
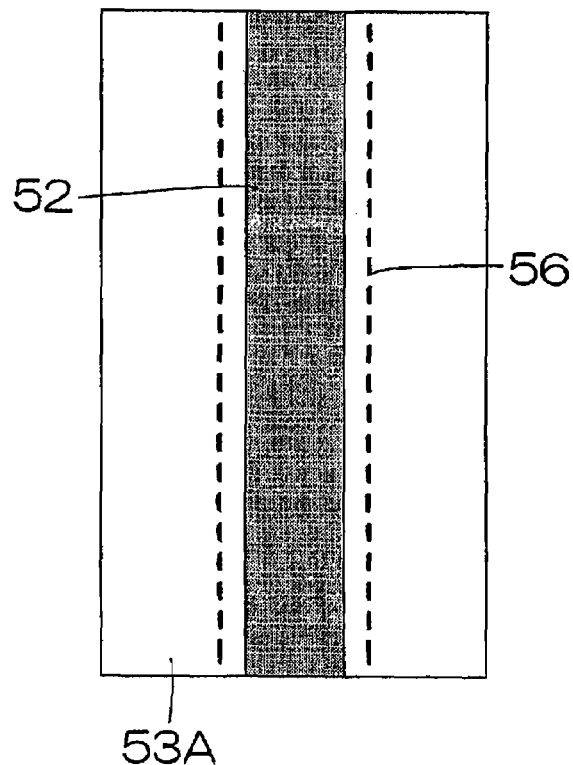
FIG. 14 is a plan view of a body fluid absorbent structure according to another embodiment.
Figure 15:
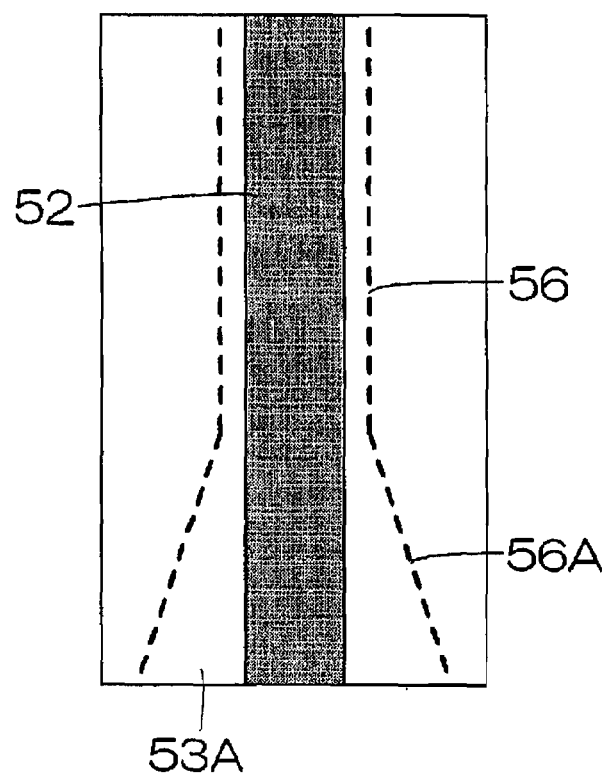
FIG. 15 is a plan view of a body fluid absorbent structure according to another embodiment.

As the embodiment of the body fluid permeable absorbent member, which is disposed on the body fluid retainable member so as to extend partly over its upper surface, there can be exemplified embodiments like those of non-woven sheet. Concretely, as shown in FIGS. 12, 13, 16 and 17, the body fluid permeable absorbent member is disposed at only a certain zone of the body fluid retainable member, which is the middle portion in its width direction and at the same time, which is the intermediate portion in its longitudinal direction. Alternatively, as shown in FIGS. 14 and 15, the body fluid permeable absorbent member is disposed at the middle portion in its width direction and at the same time so as to extend from its front end to its back end. The former embodiments (e.g., FIG. 12) permit to decrease the thickness of the article when folded, for example, folded into three by turning its front end portion and back end portion as shown in the right drawing of FIG. 12, resulting in a preferable article for the market. On the other hand, the latter embodiments (e.g., FIG. 14) are preferable in that the zone absorbing the body fluid can be enlarged in the longitudinal direction.

In the examples shown in FIG. 12 to 17, each body fluid permeable absorbent member 52 is disposed on the body fluid retainable member 53 so as to extend partly over its upper surface. Such partly extension allows pressing, e.g., embossing on the body fluid retainable absorbent member 53 at its portions, which are not faced with the body fluid permeable absorbent member 52 (In this case, the pressing may be carried out on the body fluid retainable absorbent member together with the face sheet 1 and so forth) so that the gutters 56 are formed on the body fluid retainable absorbent member. The gutters 56 are formed with the intention of controlling the body fluid diffusion by making use of characteristic that for the body fluid, it is difficult to diffuse cross the gutters 56, while it is easy to diffuse along the gutters 56.

Now, the concrete explanation will be given. For example, as shown in FIG. 12, the gutters 56, 56 are formed along the width direction in the back and front with respect to the body fluid permeable absorbent member 52. In this embodiment, after the body fluid is diffused through the permeable absorbent member 52, the gutters 56, 56 prevent the body fluid from diffusing across them toward the front end and back end of the body fluid retainable absorbent member. Such embodiment facilitates the protection against the leakage at the front end and back end. Additionally, in such embodiment, the body fluid can be diffused in the width direction quickly. Alternatively, as shown in FIGS. 13 to 15, gutters 56, 56 are formed along the longitudinal direction of the body fluid retainable absorbent member 53A in the front and back portions with respect to the body fluid permeable absorbent member 52 or in the both side portions with respect to the absorbent member 52. In each of these embodiments, after the body fluid is diffused through the body fluid permeable absorbent member 52, the gutters 56, 56 prevent the body fluid from diffusing across them toward the both side edges of the body fluid retainable absorbent member 53A. Such configuration of the article facilitates the protection against the leakage at the both side edges. Additionally, according to these configurations, the body fluid can be diffused quickly in the longitudinal direction.

Figure 16:
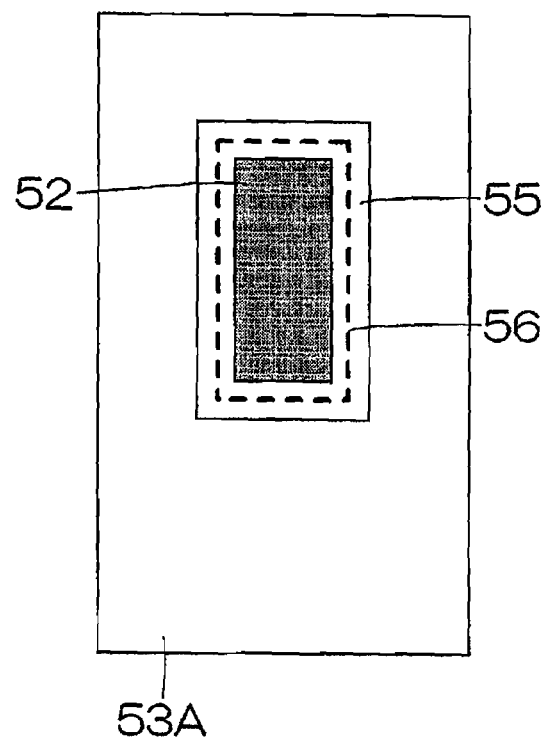
FIG. 16 is a plan view of a body fluid absorbent structure according to another embodiment.
Figure 17:
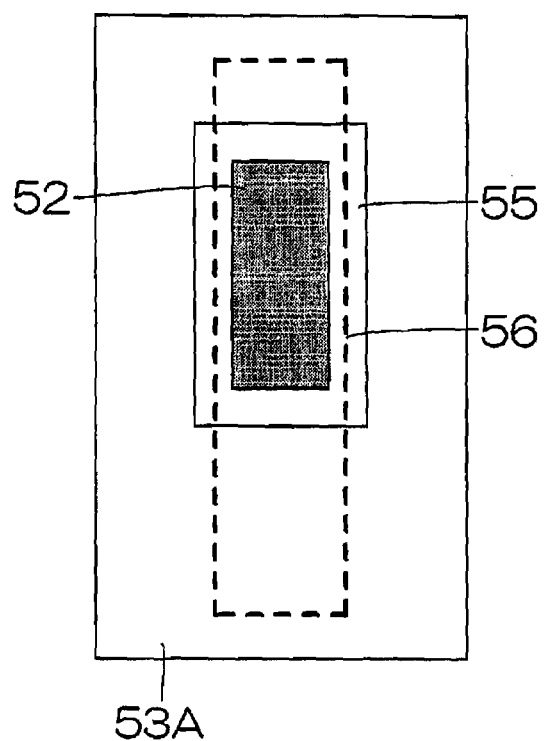
FIG. 17 is a plan view of a body fluid absorbent structure according to another embodiment.

In the above embodiments, the gutters 56, 56 are formed straight in the width direction or longitudinal direction. However, it is needless to say that the gutters 56, 56 should not be formed straight. For example, as shown in FIG. 15, the gutters 56, 56 can be formed so that their back parts 56A, 56A bend outwardly in the width direction. Actually, a gutter 56 may be formed so as to extend along the direction in which the body fluid is required to diffuse while another gutter 56 is formed so as to extend across the direction in which the body fluid is required not to diffuse. The gutters 56, 56 are formed so as to extend along the single direction such as only the width direction, only the longitudinal direction or the like. However, this is not requisite condition. For example, as shown in FIGS. 16 and 17, the gutters 56, 56 may be formed so as to surround the body fluid permeable absorbent member 52. In this situation, if the absorbent sheet 55 is disposed over the absorbent member 52 as the second sheet, as shown in FIG. 16, all of the gutters 56 may be disposed within the absorbent sheet 55, or as shown in FIG. 17, the back and front parts of the gutters 56 may be away from the absorbent sheet 55.

Although these gutters 56 can be formed in various embodiments, as shown in the drawings, the gutters 56 are preferably formed so as not to cross over the body fluid permeable absorbent member 52 for the following reason. In the present invention, since the absorbent member 52 includes the assembly of fibers in tows, such assembly tends to lose its stiffness in course of the absorption of the body fluid. Accordingly, if the gutters 56 are formed on the body fluid permeable absorbent member 52, the absorbent member 52 will sink due to the absorption of the body fluid, which will eliminates the effect of the gutters 56, because there is no enough difference in the depth between the absorbing member 52 and the gutters 56. Further, if the constituent fiber of the assembly of fibers in tows is acetate cellulose, since its melting point is as high as 230° C., it is difficult that pressing e.g., embossing cannot be carried out so deeply on the body fluid permeable absorbent member 52. In this case, forming the gutters so as not to cross the body fluid permeable member 52 is more necessary for the resultant shallow gutters 56.

[Examples of Body Fluid Absorbent Article and Examples of the Producing Method Thereof]

Now, body fluid absorbent articles as the applications of the above body fluid absorbent structures and producing methods thereof will be explained.

The First Example

Figure 18:
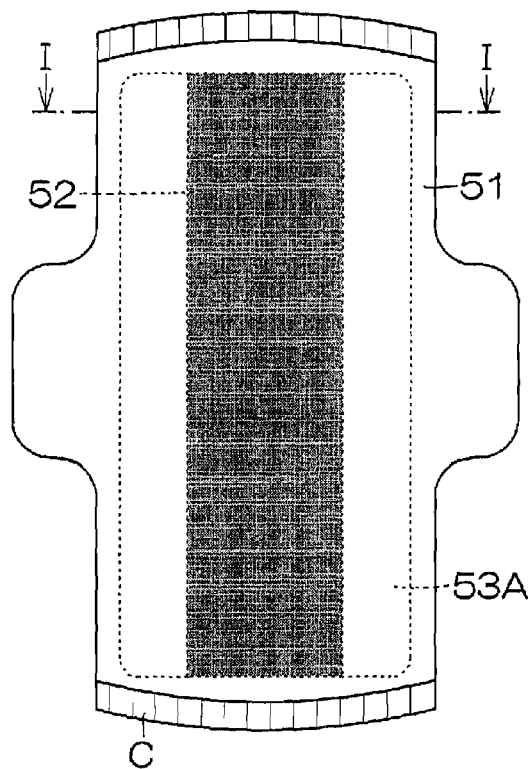
FIG. 18 is a plan view of a body fluid absorbent article according to the first example.
Figure 19:
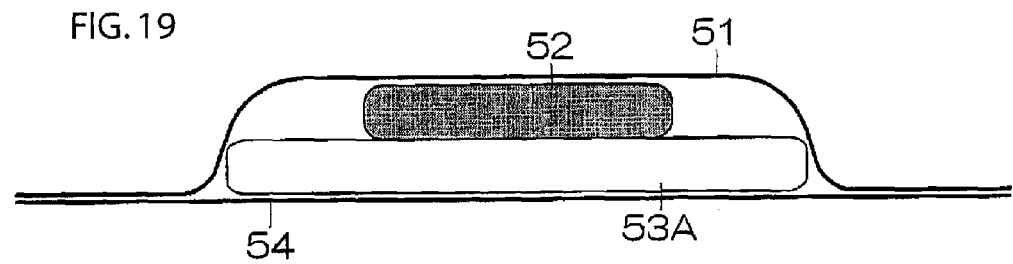
FIG. 19 is a cross section taken on line I-I of FIG. 18.

As shown in the plan view of FIG. 18 and the cross section of FIG. 19 taken on line I-I of FIG. 18, this body fluid absorbent article comprises a rectangular shaped body fluid retainable absorbent member 53A, which is interposed between the face sheet 51 and the back sheet 54. Further, the body fluid permeable absorbent member 52, which includes an assembly of fibers in tows, is interposed between the body fluid retainable absorbent member 53A and the face sheet 1. In each of some body fluid absorbent articles, pressed portions (high density portions) may be formed on the body fluid retainable absorbent member 53A. However, such configuration is not illustrated in the drawings. This is to be repeated in the following.

The shape of the face sheet 51 and that of the back sheet 54 define the outline of this article on the plan view. Then, the both side portions of the face sheet 51 and those of the back sheet 54 are extended beyond the both side edges of the body fluid retainable absorbent member 53A. These extended portions are specifically broadened outboard in the width direction at their intermediate portions. Then, these broadened portions turn to be e.g., folded flaps, which are folded and wrapped around the side edges of the wearer's garment such as a woman's underwear or the like so as to cover its external surface in use. The face sheet 51 and the back sheet 54 are joined at least at their front end C and their back end C by e.g., hot melt adhesive, ultrasonic sealing, heat seal (thermal fusion), heat press (thermocompression bonding), or the combination of these methods, in this example, by heat seal.

The body fluid permeable absorbent member 52 is disposed on only the middle portion of the body fluid retainable absorbent member 53A in its width direction with the front end and the back end being extended to reach the front end and the back end of the body fluid retainable absorbent member 53A.

Figure 20:
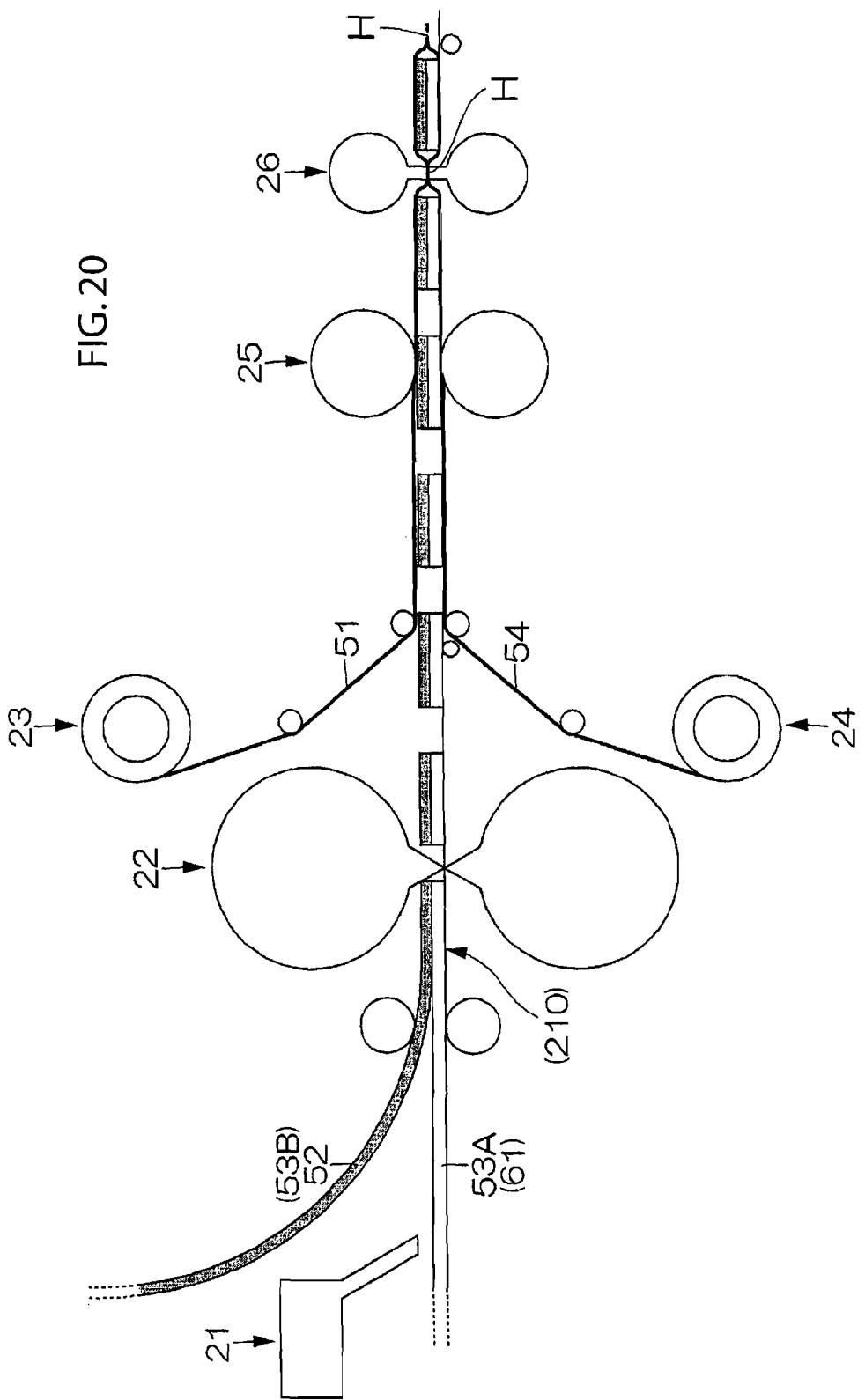
FIG. 20 is a schematic illustration showing a producing flow for the body fluid absorbent article according to the first example.

This absorbent article is produced, for example, by the following method. First, as shown in FIG. 20, adhesive such as hot melt adhesive or the like is coated, with the applicator 21, on the surface of the belt-shaped body fluid retainable absorbent member 53A, which is fed with transporting means such as a belt conveyor or the like. Next, the body fluid permeable absorbent member 52 is put on the coated retainable absorbent member 53A for jointing these absorbent members 52, 53A with adhesion of the adhesive.

Then, these joined absorbent members 52, 53A are fed to the cutter 22, where they are cut to the absorbent members 52 and 53A each having the length of each article. That is to say, cutting points of the absorbent members 52, 53A correspond to front ends and back ends of absorbent members 52, 53A each having the length of each article. In this way, as stated before, the front end and the back end of the body fluid permeable absorbent member 52 are extended to reach the front end and the back end of the body fluid retainable absorbent member 53A.

Further, while these cut absorbent members 52 and 53A are fed, the face sheet 51 unwound from the reel 23 and the back sheet 54 unwound from the reel 24 are affixed to the wearer-side surface of the absorbent member 52 and to the under surface of the absorbent member 53A, respectively.

Moreover, the absorbent members 52 and 53A, to which the face sheet 51 and the back sheet 54 are affixed, may be, for example, fed to the embosser 25 where embossing is carried out on these absorbent members 52 and 53A (However, in FIGS. 18 and 19, embossed state is not illustrated). Such embossing can be performed, for example, in the longitudinal direction of the article on the both side portions of the body fluid permeable absorbent member 52 (See FIG. 14).

After treatment such as embossing or the like, the absorbent members 52 and 53A are fed to the heat sealer 26 where the face sheet 51 and the back sheet 54 are jointed with heat seal. This heat sealing is performed at the substantially intermediate between the absorbent members 52 and 53A and the preceding absorbent members 52 and 53A and between the absorbent members 52 and 53A and the following absorbent members 52 and 53A. That is to say, the heat sealing is performed at places where the absorbent members 52 and 53A are not disposed. Consequently, heat sealing defines the front end and the back end of each absorbent article.

The Second Example

As shown in plan view, FIG. 21, sectional view, FIG. 19 taken on line I-I of FIG. 21 (Since this sectional view is the same as that of the first example, the drawing used for explaining the first example is used again) and sectional view, FIG. 22 taken on line II-II of FIG. 21, this body fluid absorbent article is configured similarly to that of the first example.

In this absorbent article, like the first example, the body fluid permeable absorbent member 52 is disposed on only the middle portion in the width direction of the body fluid retainable absorbent member 53A, but the front end 52a and the back end 52a of the absorbent member 52 are extended to reach the front ends and the back ends of the face sheet 51 and the back sheet 54, respectively (See FIG. 22). On the other hand, in the first example, the front end and the back end of the absorbent member 52 are extended to the front end and the back end of the body fluid retainable absorbent member 53A and not extended longer, respectively. Thus, the first example is more preferable than the second example from the viewpoint of protection against the front leakage and the back leakage of the body fluid as well as from the viewpoint of the ensured joint of the front end and the back end of the face sheet 51 and the front end and the back end of the back sheet 54, respectively. However, the second example can be applied from another viewpoint such as necessity for easy producing or the like.

Figure 23:
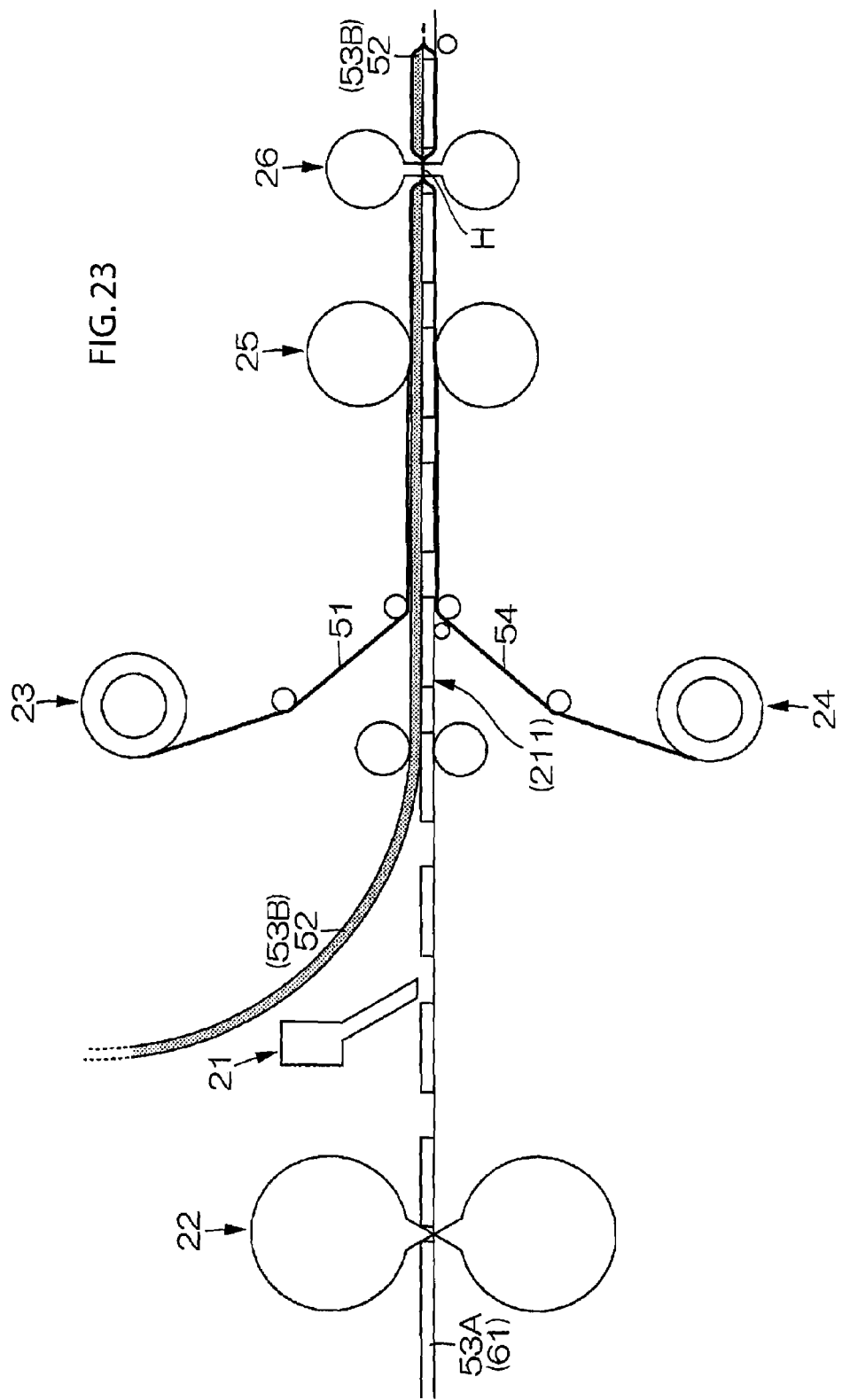
FIG. 23 is a schematic illustration showing a producing flow for the body fluid absorbent article according to the second example.

This absorbent article is produced, for example, by the following method. First, as shown in FIG. 23, the belt-shaped body fluid retainable absorbent member 53A, which is fed with transporting means such as a belt conveyor or the like, is cut solely to absorbent members 53A each having the length of each article. After that, the cut body fluid retainable absorbent member 53A is jointed with the body fluid permeable absorbent member 52. On the other hand, in the first example, as stated above, the absorbent member 52 and the absorbent member 53A are jointed before cutting. In this case, the absorbent members 52, 53A might not be cut precisely and surely when the property such as bulky nature, softness or the like is different between the body fluid retainable absorbent member 53A and the body fluid permeable absorbent member 52. However, such problem is not caused in this second example, because the absorbent member 53A is cut solely before jointing with the absorbent member 52.

Next, in this second producing example, adhesive such as hot melt adhesive or the like is coated with the applicator 21 on the surface of each cut absorbent member 53A. Then, the body fluid permeable absorbent member 52 is put on each cut and coated absorbent member for jointing these absorbent members with adhesion of the adhesive.

After that, the affixing of the face sheet 51 and the back sheet 54, embossing and heat sealing are performed like the first producing example.

In this second producing example, the heat sealing is performed while the body fluid permeable absorbent member 52 is not cut yet. Accordingly, the heat sealing is performed at places where the absorbent member 52 is disposed. This means that in the absorbent article obtained by this producing example, the body fluid permeable absorbent member 52 is extended to the front ends and the back ends of the face sheet 51 and the back sheet 54 (the front end and the back end of the article), respectively.

The Third Example

Figure 24:
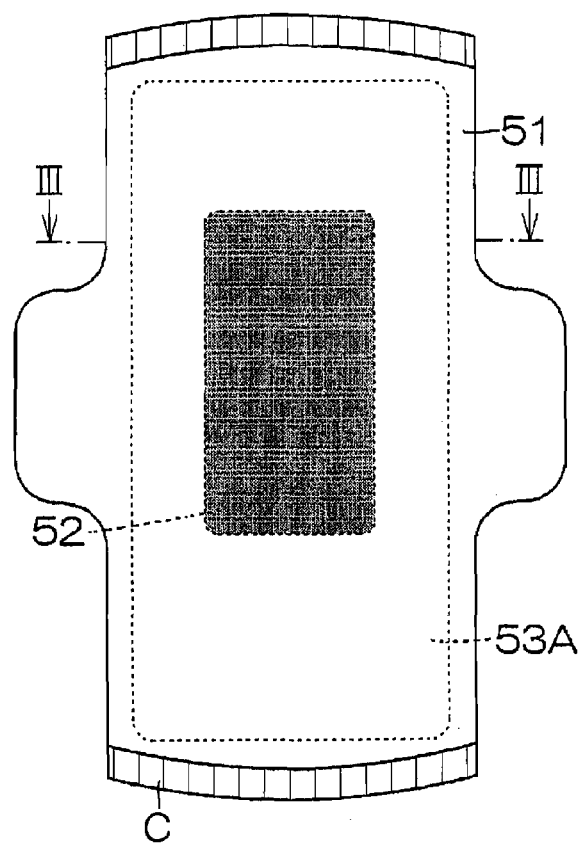
FIG. 24 is a plan view of a body fluid absorbent article according to the third example.
Figure 25:
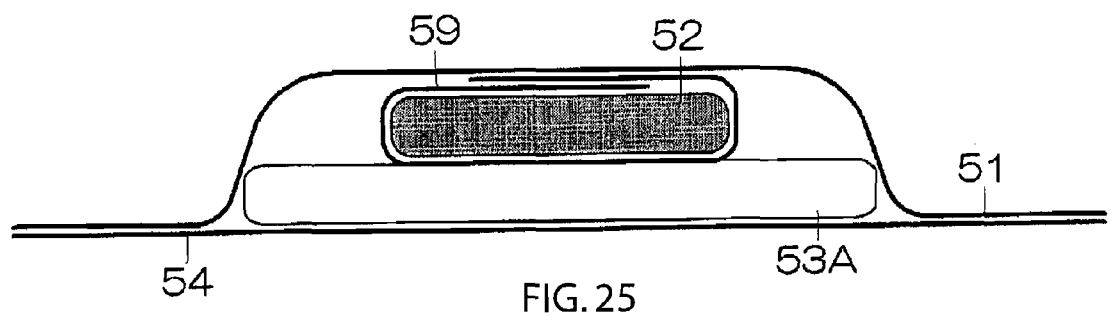
FIG. 25 is a cross section taken on line of FIG. 24.

As shown in plan view, FIG. 24 and sectional view, FIG. 25 taken on line III-III of FIG. 24, this body fluid absorbent article is configured similarly to that of the first example and that of the second example.

However, in this absorbent article, the body fluid permeable absorbent member 52 is disposed only at the zone, which is the middle portion in the width direction and at the same time the intermediated portion in the longitudinal direction of the body fluid retainable absorbent member 53A. Additionally, the absorbent member 52 is wrapped with the crepe paper 59. In this example, the body fluid permeable absorbent member 52 is disposed, in the longitudinal direction, only at the intermediated portion. As explained before, this configuration decreases the thickness of the article when folded for example, when folded into three, resulting in a preferable article for the market (See FIG. 12). However, such configuration may cause distortion of the shape, leading to the fear of eliminating the effects offered by the body fluid permeable absorbent member 52. In this regard, in this third example, such fear is lessened, because the absorbent member 52 is wrapped with the crepe paper.

The method for wrapping the absorbent member 52 with the crepe paper is not specifically limited but the method shown in FIG. 26 will be explained as one example.

In this method, first, adhesive such as hot melt adhesive or the like is coated with the applicator 21 on the surface of the crepe paper 59, which is fed with transporting means such as a belt conveyor or the like. In this producing method, the crepe paper 59 is adapted to be belt-shaped and have the width being larger than that of the body fluid permeable absorbent member 52.

After the coating of the adhesive on the surface of the crepe paper 59, the body fluid permeable absorbent member 52 is put on the coated crepe paper for jointing them with adhesion of the adhesive. Next, while the crepe paper 59 and the absorbent member 52 are fed by transporting means, the both side portions of the crepe paper 59 are, with a folding member 27, folded so as to wrap around the both side edges of the absorbent member 52 and cover its external surface. By doing so, the shape distortion of the absorbent member 52 in the width direction is suppressed by the crepe paper 59 due to its containment for the absorbent member 52, while the longitudinal shape distortion of the absorbent member 52 is suppressed by the crepe paper 59 due to its jointing with the absorbent member 52.

After that, the body fluid permeable absorbent member 52 covered with the crepe paper is fed to the cutter 22 where the absorbent member is cut to the absorbent members each having the length of each article.

The Fourth Example

In each of the stated articles according to the first to third examples, between the face sheet 51 and the body fluid retainable absorbent member 53A, the single body fluid permeable absorbent member 52 is disposed. However, it is not intended that the number of the absorbent member 52 is limited to one.

Figure 27:
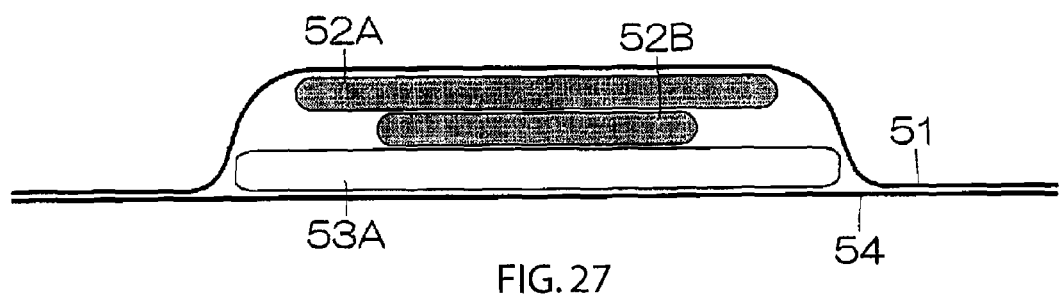
FIG. 27 is a cross section of a body fluid absorbent article according to the fourth example.
Figure 28:
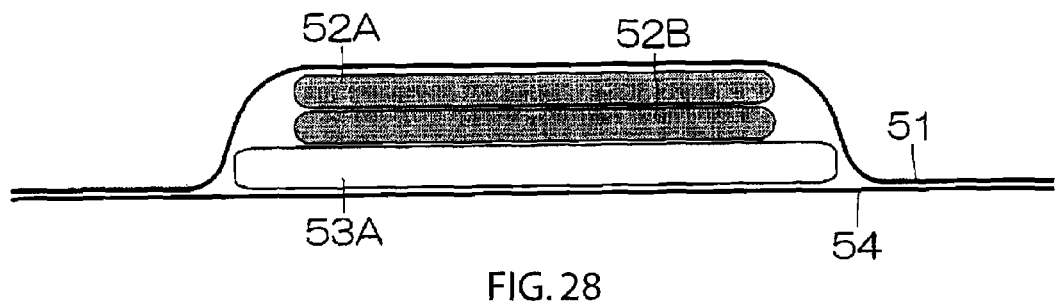
FIG. 28 is a cross section of a body fluid absorbent article according to the fourth example.
Figure 29:
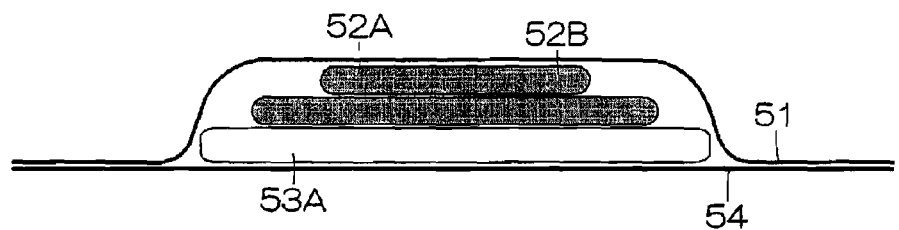
FIG. 29 is a cross section of a body fluid absorbent article according to the fourth example.
Figure 31:
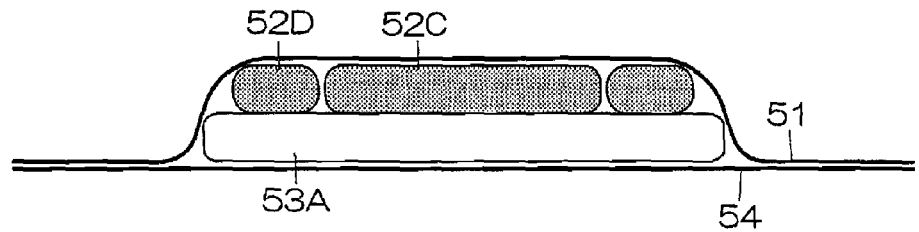
FIG. 31 is a cross section of a body fluid absorbent article according to the fourth example.

Laminated plural number; two, three, four or more absorbent members 52 can be disposed, for example, as shown in FIGS. 27 to 29, the two absorbent members 52 (the upper absorbent member 52A and the lower absorbent member 52B) are disposed while they are laminated each other. Further, plural number; two, three, four or more absorbent members 52 can be disposed side by side in the width direction, for example, as shown in FIG. 31, the single absorbent member 52C is disposed at the middle portion and the two absorbent members 52D; 52D are disposed at the both sides.

Figure 30:
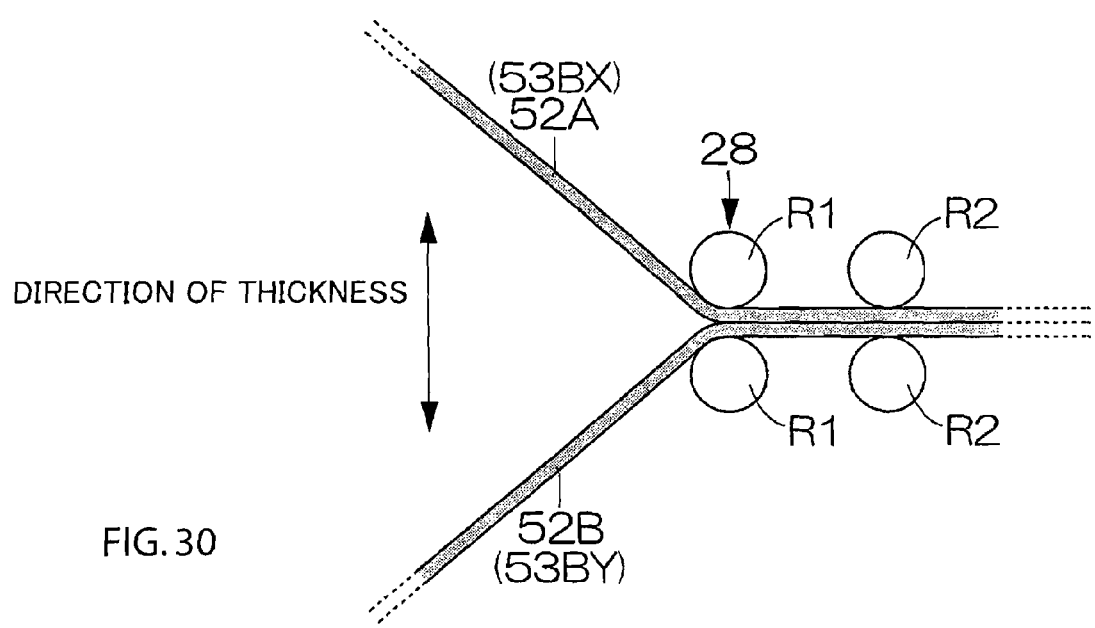
FIG. 30 is a schematic illustration showing a producing flow for the body fluid absorbent article according to the fourth example.

The method for disposing the body fluid permeable absorbent members 52 in the laminated fashion or in the width direction is not specifically limited. For example, in the laminated fashion, as shown in FIG. 30, the upper absorbent member 52A and the lower absorbent member 52B are fed down at an angle and fed up at an angle, in the direction of the thickness of the article and inserted between the roll R1-roll R1 of the pair of positioning and adjusting means 28 so that the absorbent member and the absorbent member can be laminated. In this case, the width of the upper absorbent member 52A and the width of the lower absorbent member 52B are desirably designed so that the absorbent articles shown in FIGS. 27 to 29 can be produced. In the absorbent article shown in FIG. 27, the lower absorbent member 52B is smaller than the upper absorbent member 52A in the width. Then, in the absorbent article shown in FIG. 28, the lower absorbent member 52B is the same as the upper absorbent member 52A in the width. Finally, the absorbent article shown in FIG. 29, the upper absorbent member 52A is smaller than the lower absorbent member 52B in the width.

Figure 32:
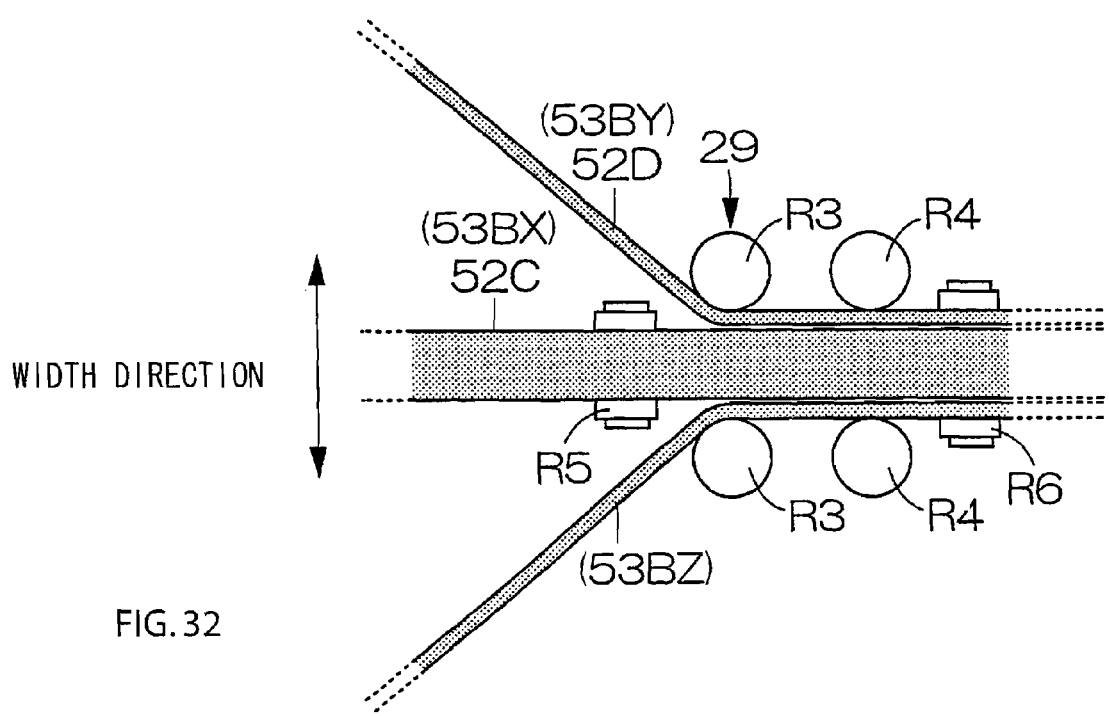
FIG. 32 is a schematic illustration showing a producing flow for the body fluid absorbent article according to the fourth example.

On the other hand, in case the absorbent members 52 are disposed side by side, as shown in FIG. 32, the single absorbent member 52C to be positioned at the middle portion is fed straightly and the two absorbent members 52D; 52D to be positioned at the both side portions are fed down at angle and fed up at an angle in the width direction. Then, these absorbent members 52D, 52C, 52D are inserted between the roll R3-roll R3 of the pair of positioning and adjusting means 29, respectively so that they can be disposed side by side.

[Addition of Binder to Assembly of Fibers in Tows]

The assembly of fibers in tows can be used as the good absorbent member, which retains the body fluid with high capacity due to its porosity. However, such assembly tends to lose its stiffness when it retains the body fluid. That is to say, the porosity of the assembly is decreased. Thus, the retaining capacity of the assembly for the body fluid is remarkably decreased. Now, embodiments adapted particularly to keep the stiffness will be explained.

Each of the absorbent structures 200 shown in FIGS. 33 to 42 comprises the absorbent member 53B, which includes the assembly of fibers in tows and absorbent polymer. Then, binder is added to the assembly of fibers in tows. In each drawing, $53B_1$, $53B_2$ designate zones which are different each other in their added amount of binder. In this case, $53B_1$, $53B_2$ are arranged according to the order of the added amount of binder ($53B_1 > 53B_2$).

In this absorbent structure 200, the absorbent member 53B can be individually wrapped with crepe paper and the like, and besides, as shown in FIGS. 43 to 53, the absorbent member 61 made of airformed pulp or the like is laminated on the under surface of the body fluid retainable absorbent member 52B. This absorbent structure 200 can be used in a body fluid absorbent article as its suitable component and has desired thickness and the flat shape of a square, an hourglass, an elliptical and so forth in the plan view seen from the wearer-side.

FIGS. 33 to 37 are plan views of the absorbent structure 200 seen from the wearer-side.

Figure 33:
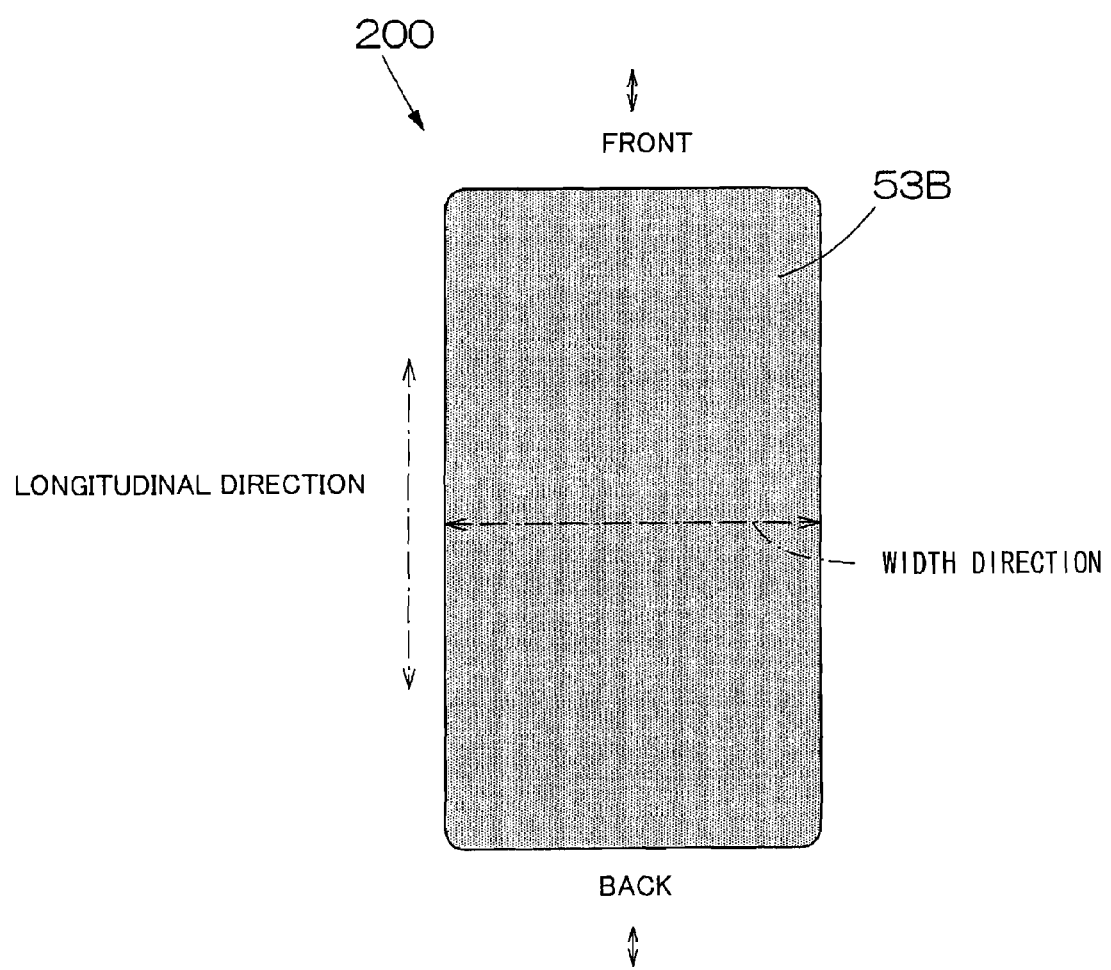
FIG. 33 is a plan view schematically showing the embodiment of a binder added absorbent member.

In the embodiment shown in FIG. 33, the binder is added to the whole of the assembly of fibers in tows. Precisely, the binder is added uniformly to the whole of the assembly of fibers, the wearer-side surface, under surface, inside and outside of the assembly so that the adhesion degree or fusion degree of the fibers is reinforced in the contacting portions of the fibers in the form of at least one of line and dot. In this embodiment, the stiffness can be kept well and the body fluid permeability is improved.

Figure 34:
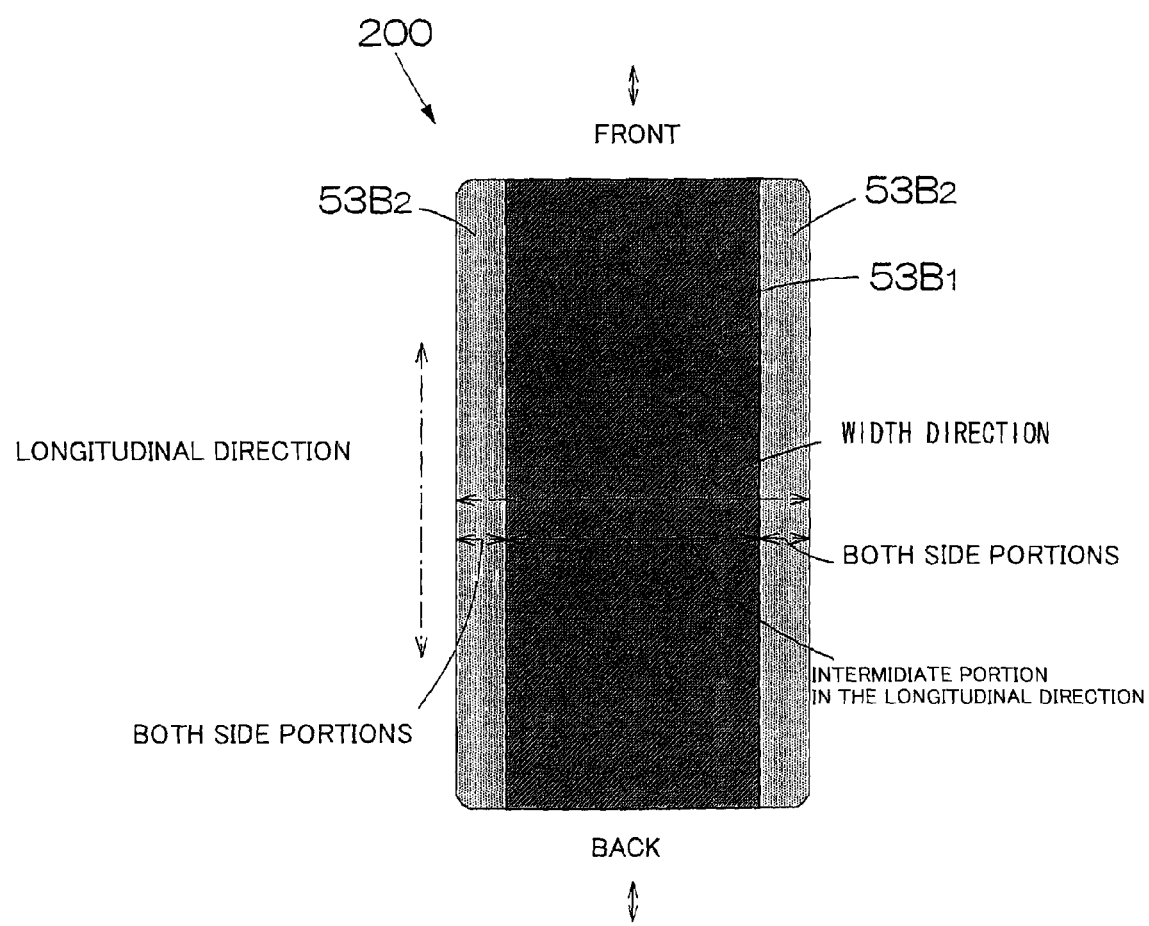
FIG. 34 is a plan view schematically showing the embodiment of a binder added absorbent member.

In the embodiment shown in FIG. 34, the adhesion degree or fusion degree of the fibers at the middle portion ($53B_1$) in the width direction is stronger than those at the both side portions ($53B_2$, $53B_2$) in the width direction by adjusting the added amount of binder to the middle portion ($53B_1$) so as to be larger than the added amount of binder to the both side portions ($53B_2$, $53B_2$). In this absorbent structure 200, for example, the absorbent member 53B is incorporated into a body fluid absorbent article such as a sanitary napkin or the like so that the longitudinal direction of the absorbent member 53B corresponds to the longitudinal direction of the absorbent article. Thus, in this absorbent article, the body fluid is absorbed quickly at the zone near the wearer's excretory organ, for example, at the zone into which discharged menstrual blood is absorbed. Additionally, this absorbent article offers the stiffness at the both side portions as well as protection against the side leakage.

Figure 35:
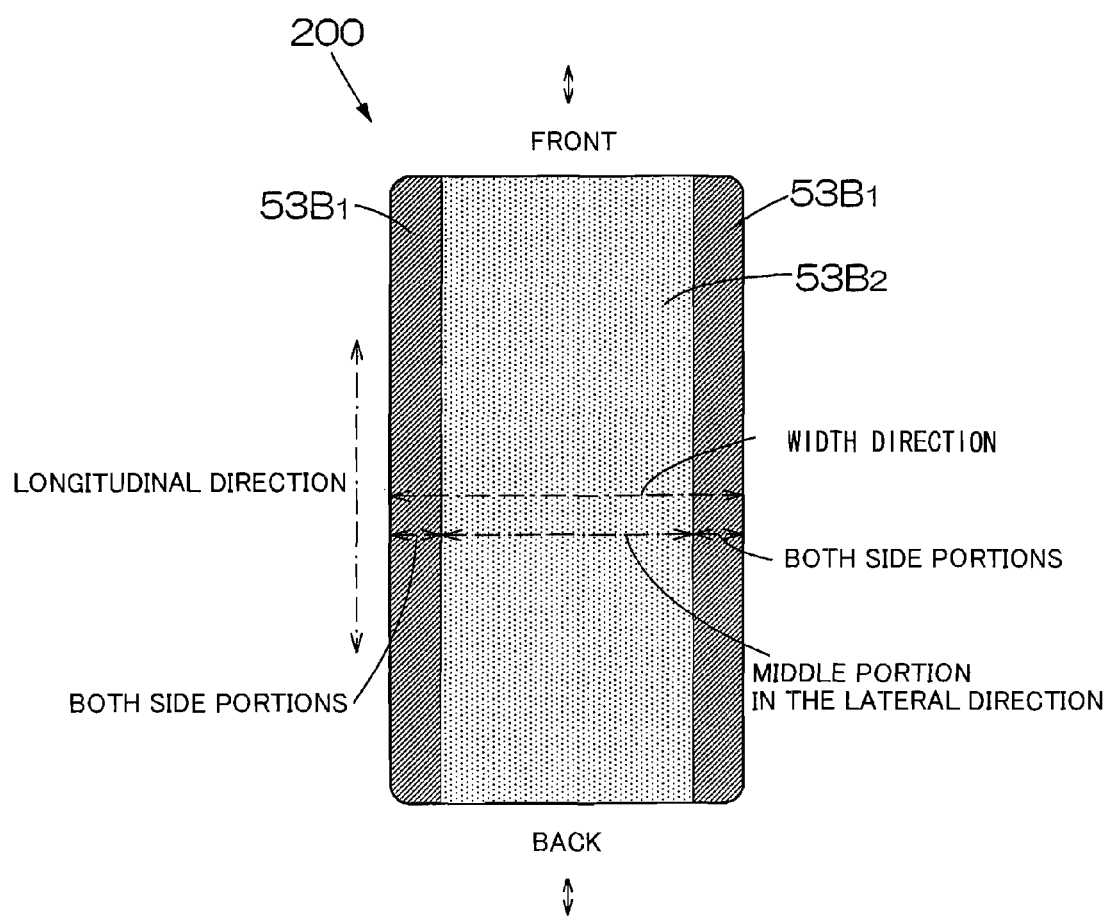
FIG. 35 is a plan view schematically showing the embodiment of a binder added absorbent member.

In the embodiment shown in FIG. 35, the adhesion degrees or fusion degrees of the fibers at the both side portions ($53B_1$, $53B_1$) in the width direction are stronger than that at the middle portion ($53B_2$) in the width direction by adjusting the added amount of binder to the both side portions ($53B_1$, $53B_1$) so as to be larger than the added amount of binder to the middle portion ($53B_2$).

Figure 36:
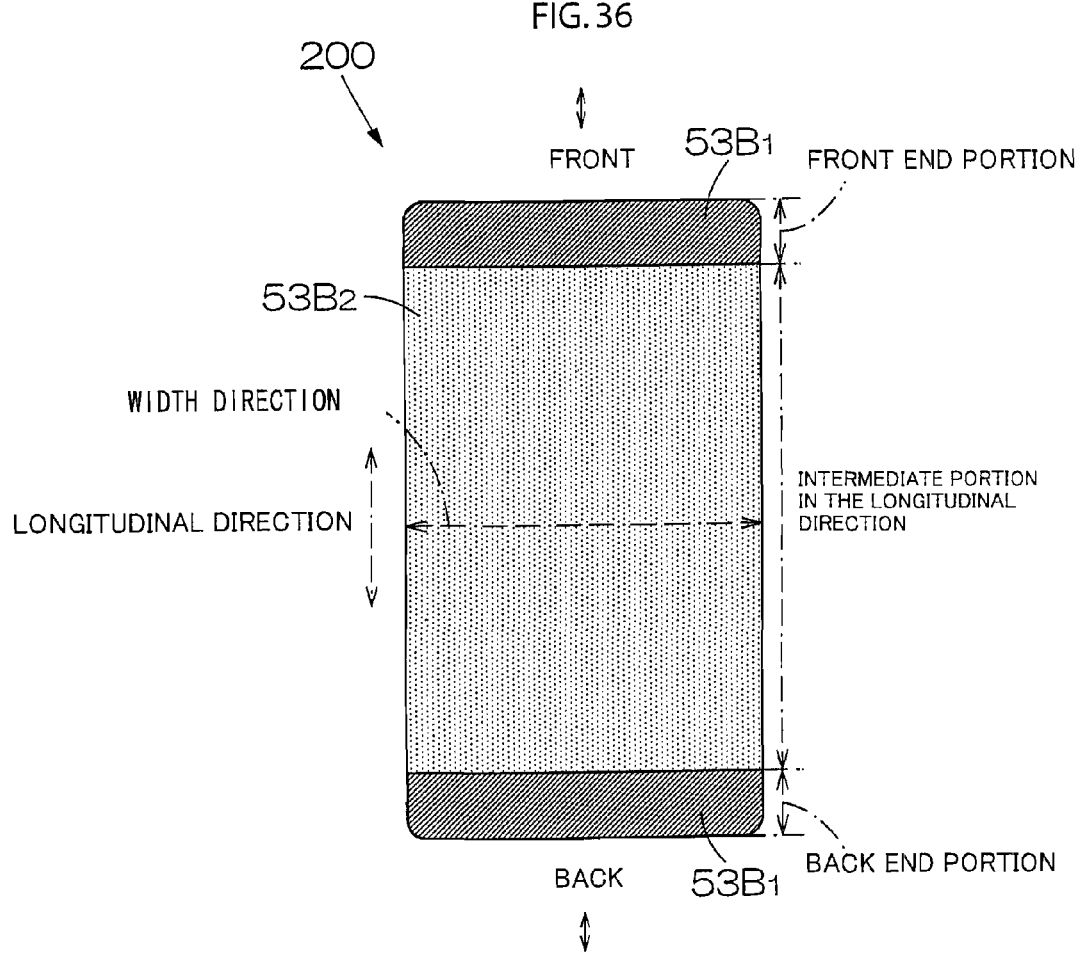
FIG. 36 is a plan view schematically showing the embodiment of a binder added absorbent member.

In the embodiment shown in FIG. 36, the adhesion degrees or fusion degrees of the fibers at the front end portion and the back end portion ($53B_1$, $53B_1$) in the longitudinal direction of the assembly of fibers are stronger than that at the intermediate portion ($53B_2$) in the longitudinal direction by adjusting the added amount of binder to the front end portion and to the back end portion ($53B_1$, $53B_1$) so as to be larger than the added amount of binder to the intermediate portion ($53B_2$). In this absorbent structure 200, for example, the absorbent member 53B is incorporated into a body fluid absorbent article such as a sanitary napkin or the like so that the longitudinal direction of the absorbent member 53B corresponds to the longitudinal direction of the absorbent article. Thus, in this absorbent article, the body fluid is absorbed quickly at the zone near the wearer's excretory organ, for example, at the zone into which discharged menstrual blood is absorbed. Additionally, this absorbent article offers the stiffness at the front and back end portions as well as protection against the front and back leakage.

Figure 37:
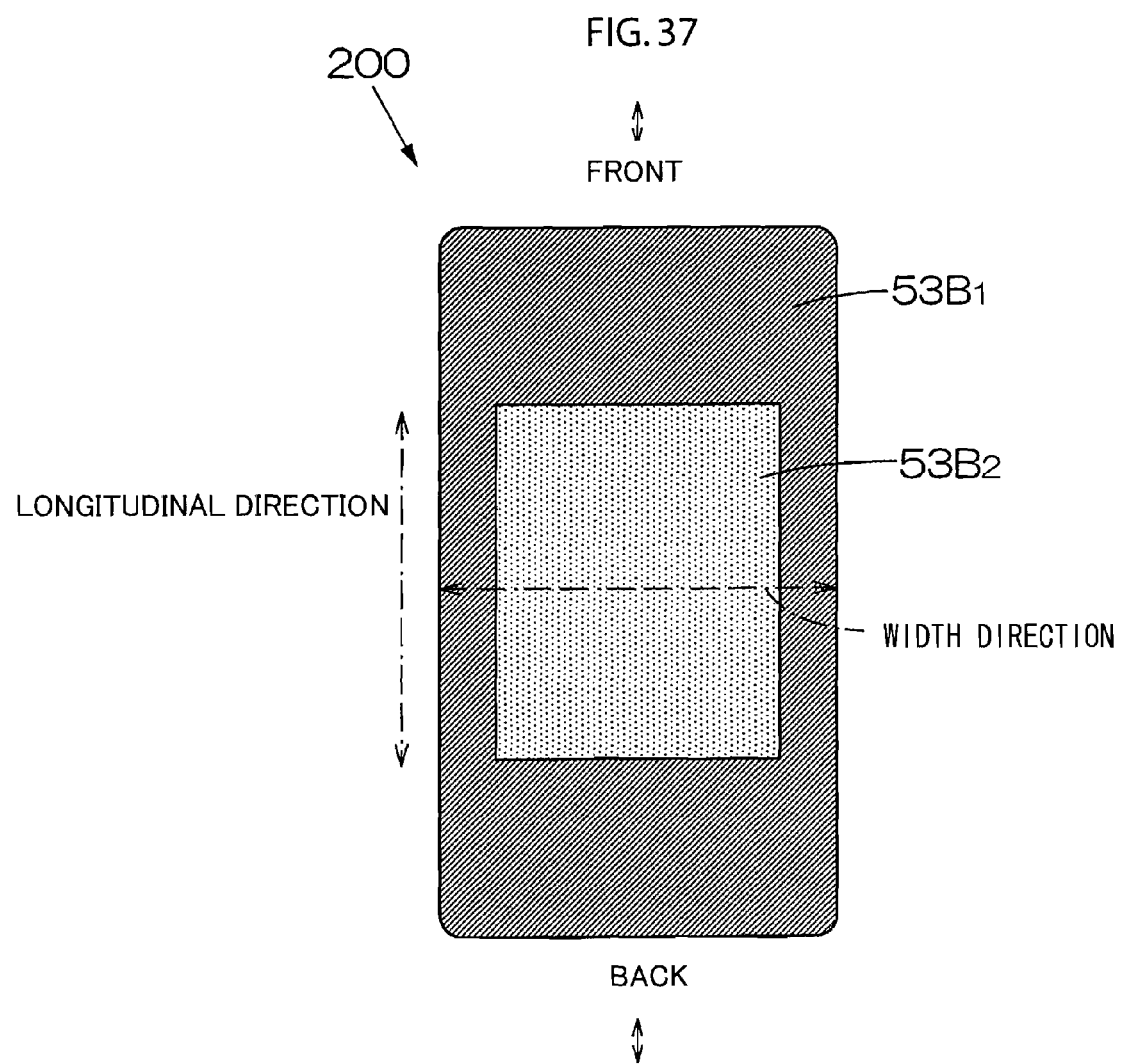
FIG. 37 is a plan view schematically showing the embodiment of a binder added absorbent member.

In the embodiment shown in FIG. 37, the adhesion degree or fusion degree of the fibers at the surrounding portion ($53B_1$) of the assembly of fibers is stronger than that at the surrounded portion ($53B_2$) by adjusting the added amount of binder to the surrounding portion ($53B_1$) so as to be larger than the added amount of binder to the surrounded portion ($53B_2$). In other words, the added amount of binder is decreased only to the center portion ($53B_2$) of the assembly of fibers. In this absorbent structure 200, for example, the absorbent member 53B is incorporated into a body fluid absorbent article such as a sanitary napkin or the like so that the longitudinal direction of the absorbent member 53B corresponds to the longitudinal direction of the absorbent article. Thus, in this absorbent article, the body fluid is absorbed quickly at the zone near the wearer's excretory organ, for example, at the zone into which discharged menstrual blood is absorbed, besides, the article offers stiffness at this zone. Additionally, this absorbent article offers the more reliable stiffness at the surrounding portion as well as protection against the front, back and side leakage.

FIGS. 38 to 42 are the cross sections in the width direction of the absorbent structure 200.

Figure 38:
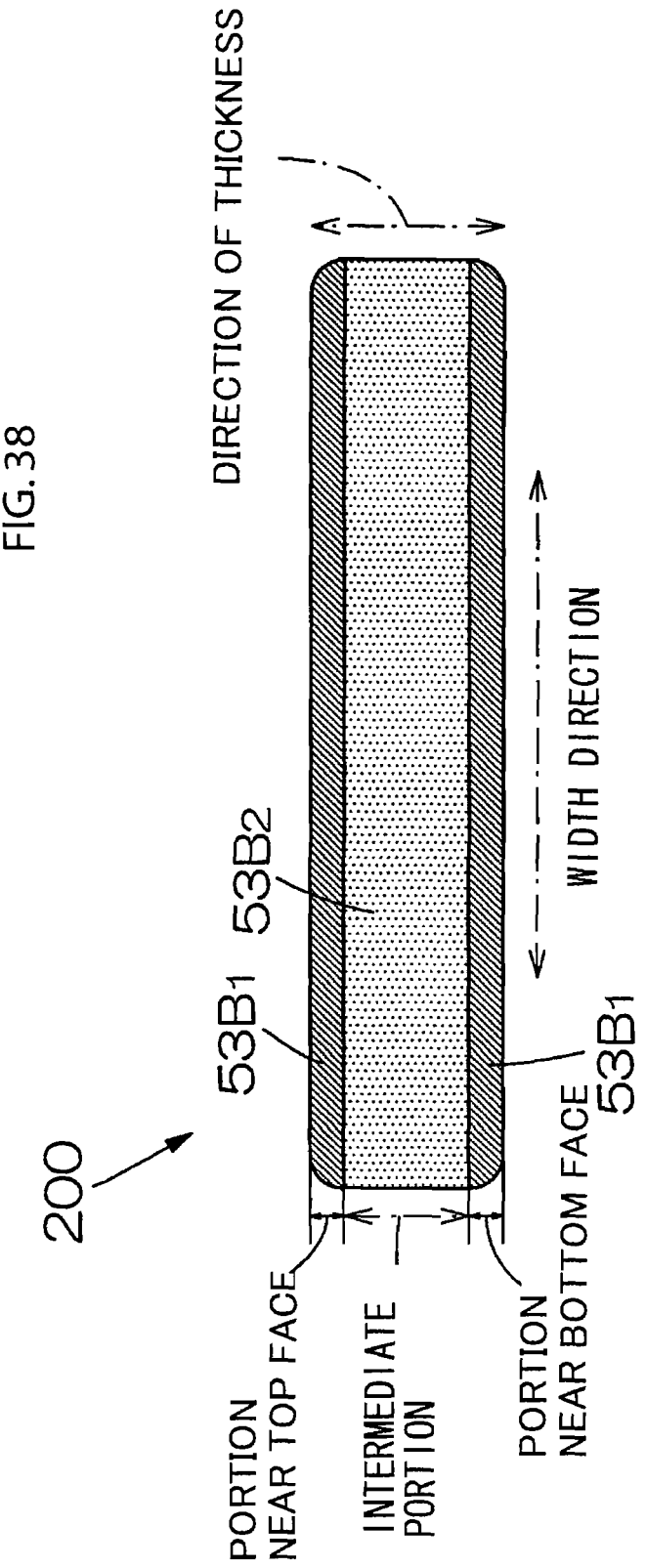
FIG. 38 is a cross section schematically showing the embodiment of a binder added absorbent member.

In the embodiment shown in FIG. 38, the adhesion degrees or fusion degrees of the fibers at the portion ($53B_1$) near the top face and at the portion ($53B_1$) near the bottom face are stronger than that at the intermediate portion ($53B_2$) between the top face and the bottom face by adjusting the added amount of binder to the portion ($53B_1$) near the top face and to the portion ($53B_1$) near the bottom face so as to be larger than the added amount of binder to the intermediate portion ($53B_2$). This absorbent structure 200 offers stiffness at the portion ($53B_1$) near the top face, the portion ($53B_1$) near the bottom face and the intermediate portion ($53B_2$), specifically more reliable stiffness at the portion ($53B_1$) near the top face and the portion ($53B_1$) near the bottom face. Then, the body fluid can be absorbed quickly into this absorbent structure 200, and besides, the body fluid is hardly remained at the portion ($53B_1$) near the top face and the portion ($53B_1$) near the bottom face. In this way, this absorbent structure 200 forms an absorbent article, which gives an impression of cleanliness.

Figure 39:
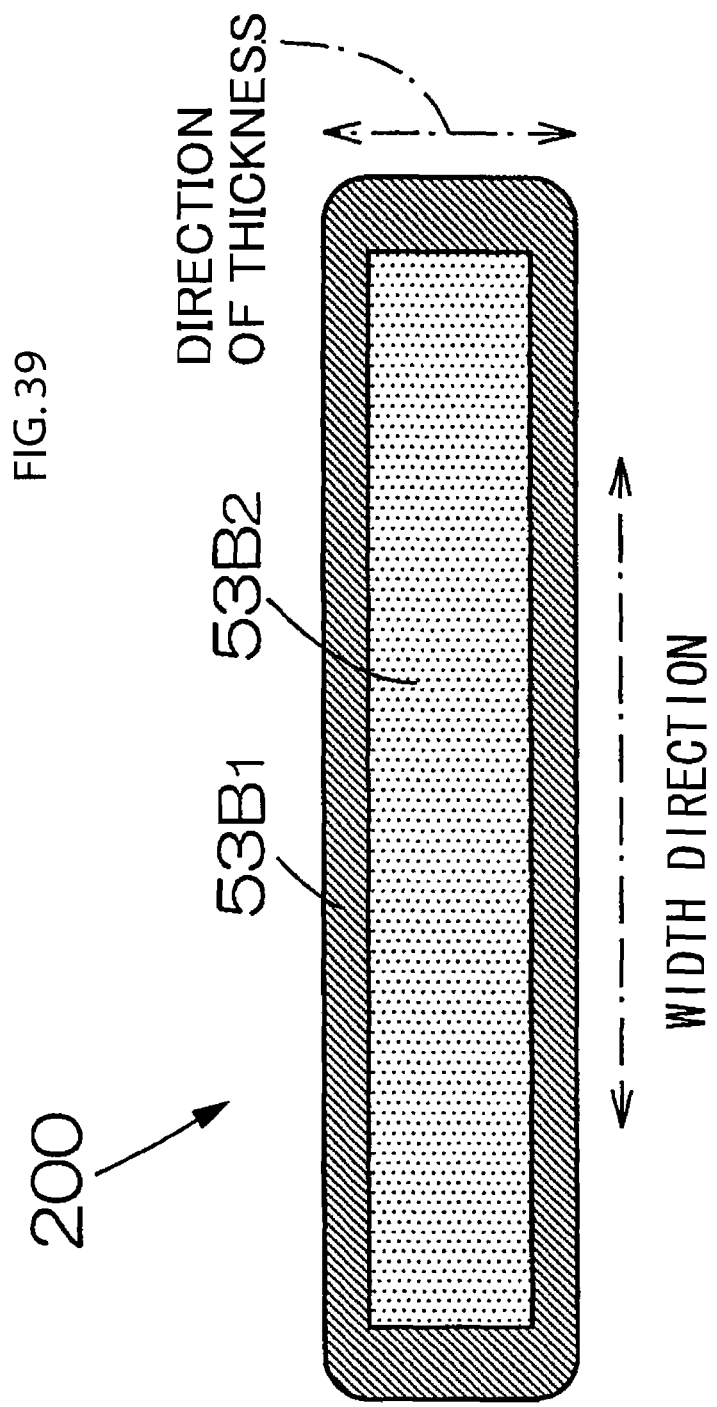
FIG. 39 is a cross section schematically showing the embodiment of a binder added absorbent member.

In the embodiment shown in FIG. 39, the adhesion degrees or fusion degrees of the fibers at the portion ($53B_1$) near the top face, at the portion ($53B_1$) near the bottom face, and at the side end portions ($53B_1$, $53B_1$) on the cross section in the width direction are stronger than that at the central portion ($53B_2$) on the cross section in the width direction by adjusting the added amount of binder to the portion ($53B_1$) near the top face, to the portion ($53B_1$) near the bottom face and to the side end portions ($53B_1$, $53B_1$) so as to be larger than the added amount of binder to the central portion ($53B_2$). This embodiment offers, addition to the advantages given by the embodiment shown in FIG. 38, the stiffness at the side end portions ($53B_1$, $53B_1$) on the cross section in the width direction. Further, the body fluid can be absorbed quickly also at the side end portions.

Figure 40:
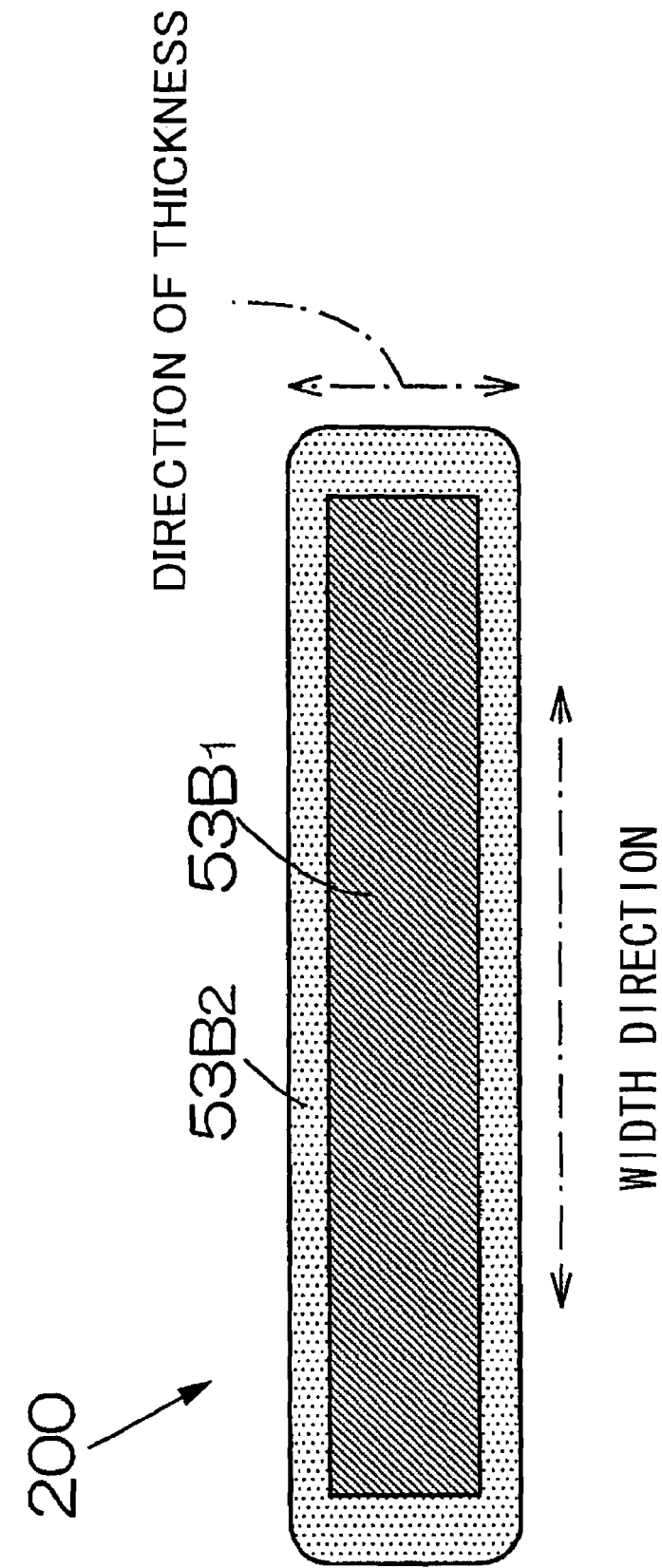
FIG. 40 is a cross section schematically showing the embodiment of a binder added absorbent member.

In the embodiment shown in FIG. 40, the adhesion degree or fusion degree of the fibers at the central portion ($53B_1$) on the cross section in the width direction is stronger than that at the portion ($53B_2$) near the top face, at the portion ($53B_2$) near the bottom face, and at the side end portions ($53B_2$, $53B_2$) on the cross section in the width direction by adjusting the added amount of binder to the central portion ($53B_1$) so as to be larger than the added amount of the binder to the portion ($53B_2$) near the top face, to the portion ($53B_2$) near the bottom face and to the side end portions ($53B_2$, $53B_2$).

Figure 41:
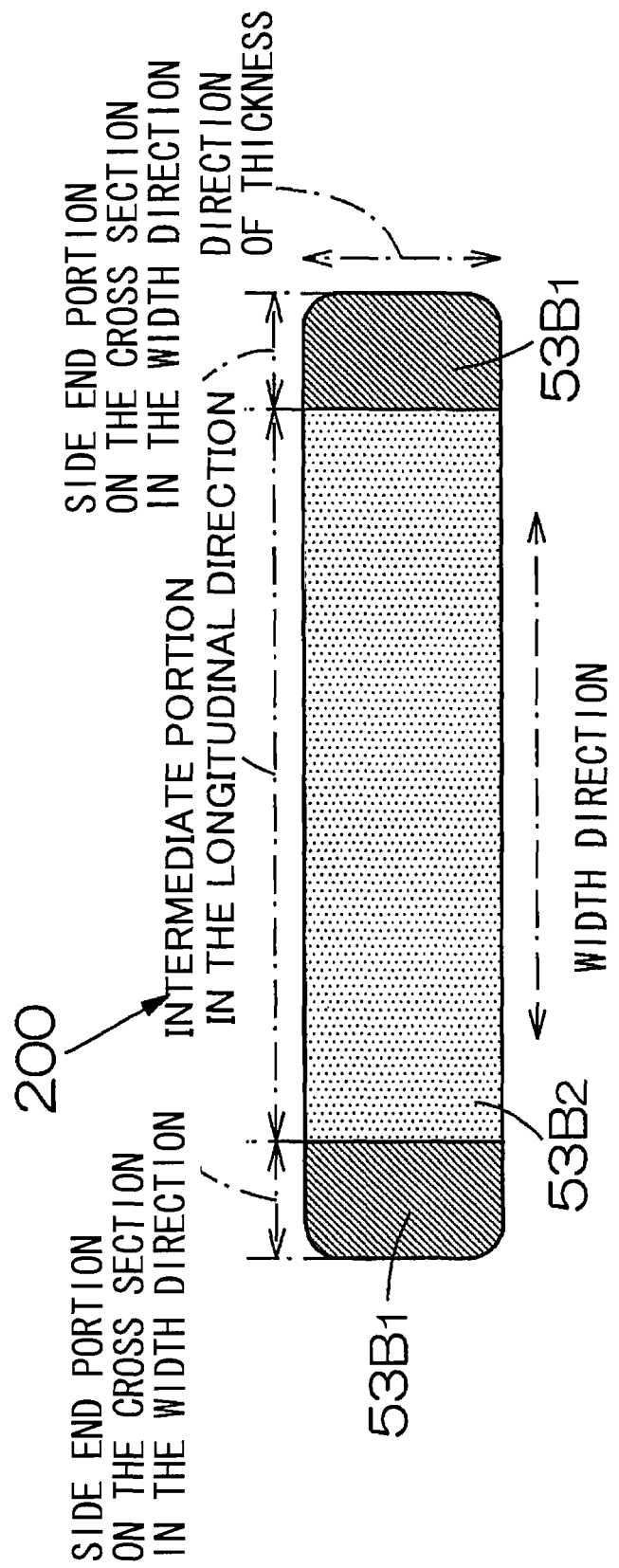
FIG. 41 is a cross section schematically showing the embodiment of a binder added absorbent member.

In the embodiment shown in FIG. 41, the adhesion degrees or fusion degrees of the fibers at the side end portions ($53B_1$, $53B_1$) on the cross section in the width direction are stronger than that at the midway portion ($53B_2$) on the cross section in the width direction by adjusting the added amount of binder to the side end portions ($53B_1$, $53B_1$) so as to be larger than the added amount of the binder to the midway portion ($53B_2$). This embodiment offers the stiffness at the side end portions ($53B_1$, $53B_1$) on the cross section in the width direction.

Figure 42:
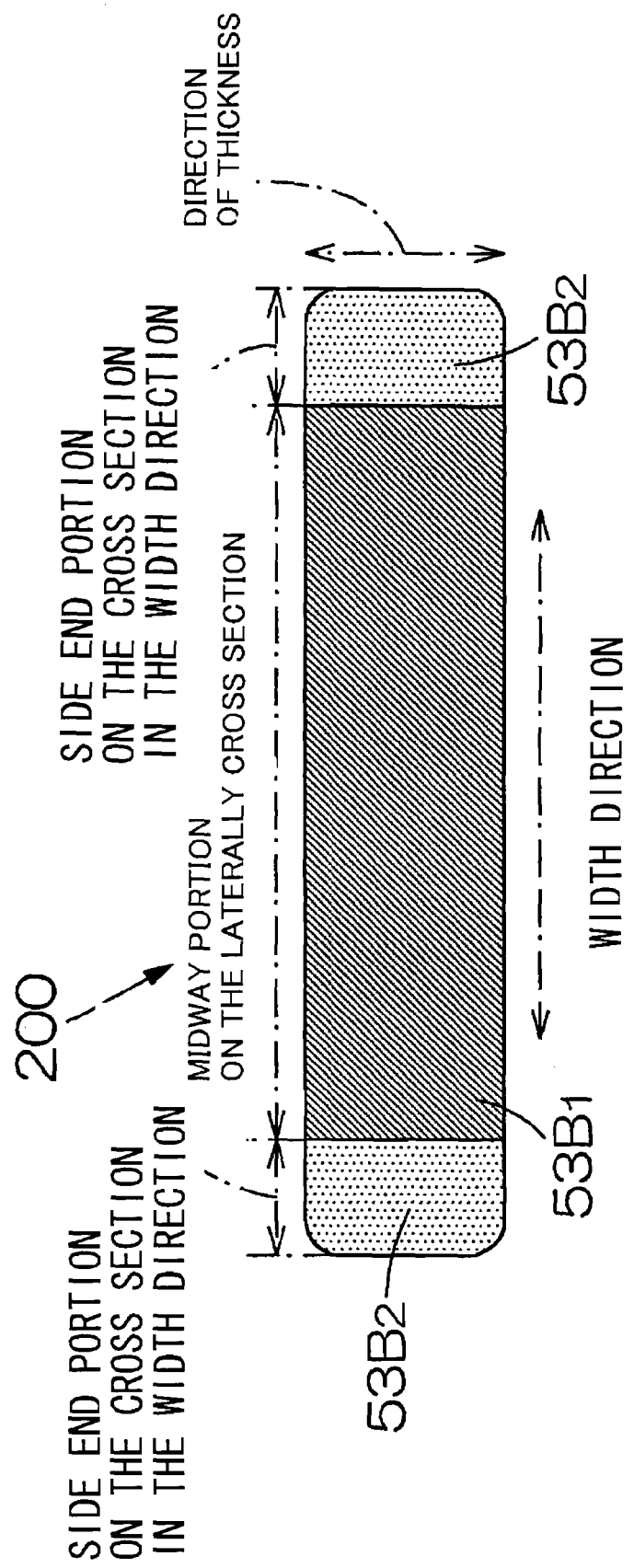
FIG. 42 is a cross section schematically showing the embodiment of a binder added absorbent member.
Figure 43:
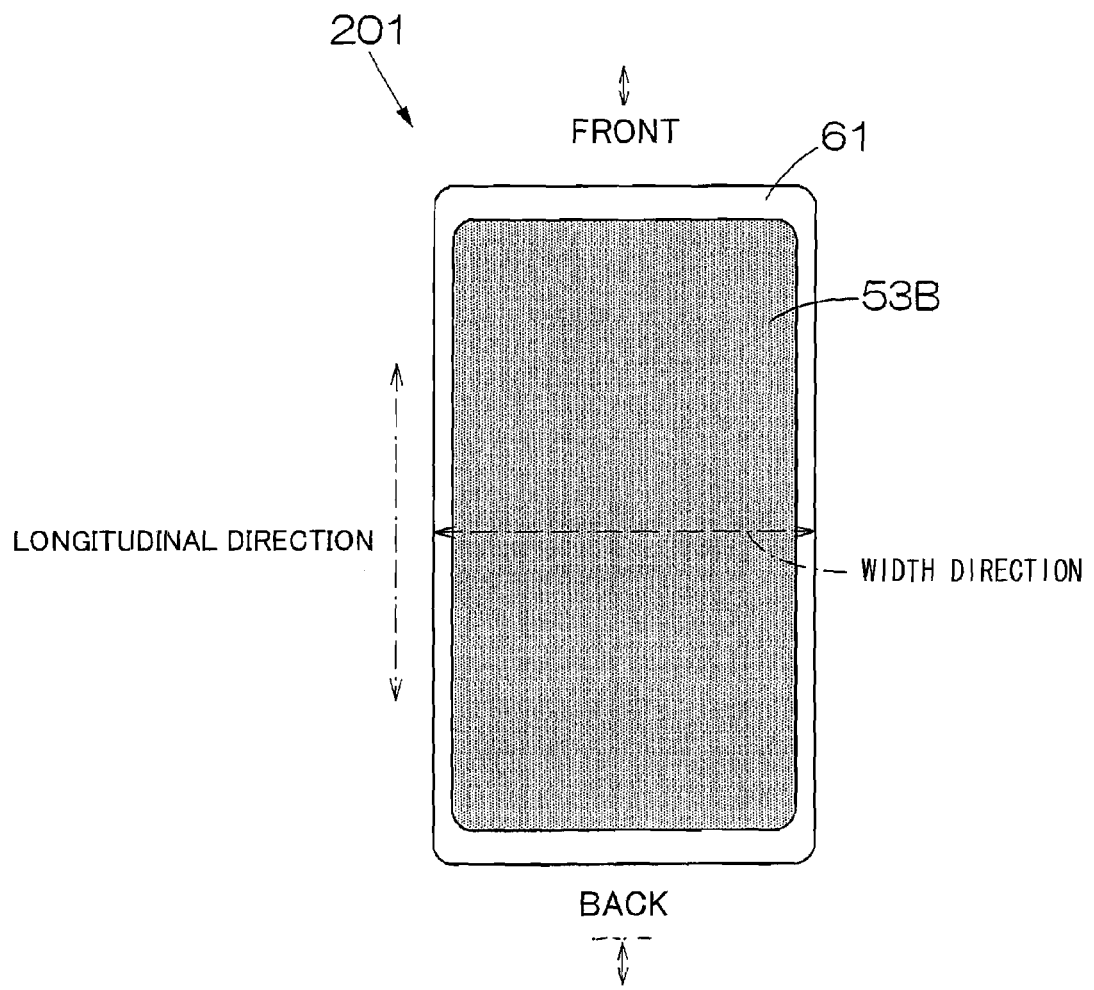
FIG. 43 is a plan view schematically showing the embodiment of a binder added absorbent member, on which another absorbent member is laminated.

In the embodiment shown in FIG. 42, the adhesion degree or fusion degree of the fibers at the midway portion ($53B_1$) on the cross section in the width direction is stronger than that at the side end portions ($53B_2$, $53B_2$) on the cross section in the width direction by adjusting the added amount of binder to the midway portion ($53B_1$) so as to be larger than the side end portions ($53B_2$, $53B_2$).

The relation between the embodiments shown in the plan views and those shown in the cross sections is not exclusive. That is to say, the conditions of the both embodiments can be put together within the permitted limits. For example, when the absorbent structure 200 has the embodiment shown in FIG. 34 on the plan view seen from the wearer-side, and at the same time it has the embodiment shown in FIG. 41 on the cross section in the width direction, it is needless to say that this absorbent structure 200 is included in the present invention.

As shown in FIGS. 43 to 46, the absorbent structure 201 may comprise the absorbent member 53B, which includes an assembly of fibers in tows and absorbent polymer, and the absorbent member 61, which is made of an absorbent material other than the tow and which is laminated on the under surface of the absorbent member 53B.

In this case, for example, when the absorbent structure 201 is used for an absorbent article such as a sanitary napkin or the like, the exposed surface of the absorbent member 53B is to be the wearer-side surface. In this way, the discharged body fluid such as menstrual blood or the like can be absorbed into the absorbent member 53B quickly and moved to reach the other absorbent member 61, where the body fluid is retained and saved. As explained here, the quick absorbing and retaining of the body fluid can be ensured in the absorbent member 53B. Further, since the binder is added to cause fiber-fiber bonding, the body fluid can be absorbed into the absorbent member 53B repeatedly one after another. Hence, the body fluid is not remained on the external surface of the article, which thereby gives an impression of cleanliness. Additionally, near the wearer-side surface, since the body fluid can be absorbed at the high speed maintained well, this absorbent article offers protection against the leakage.

Figure 44:
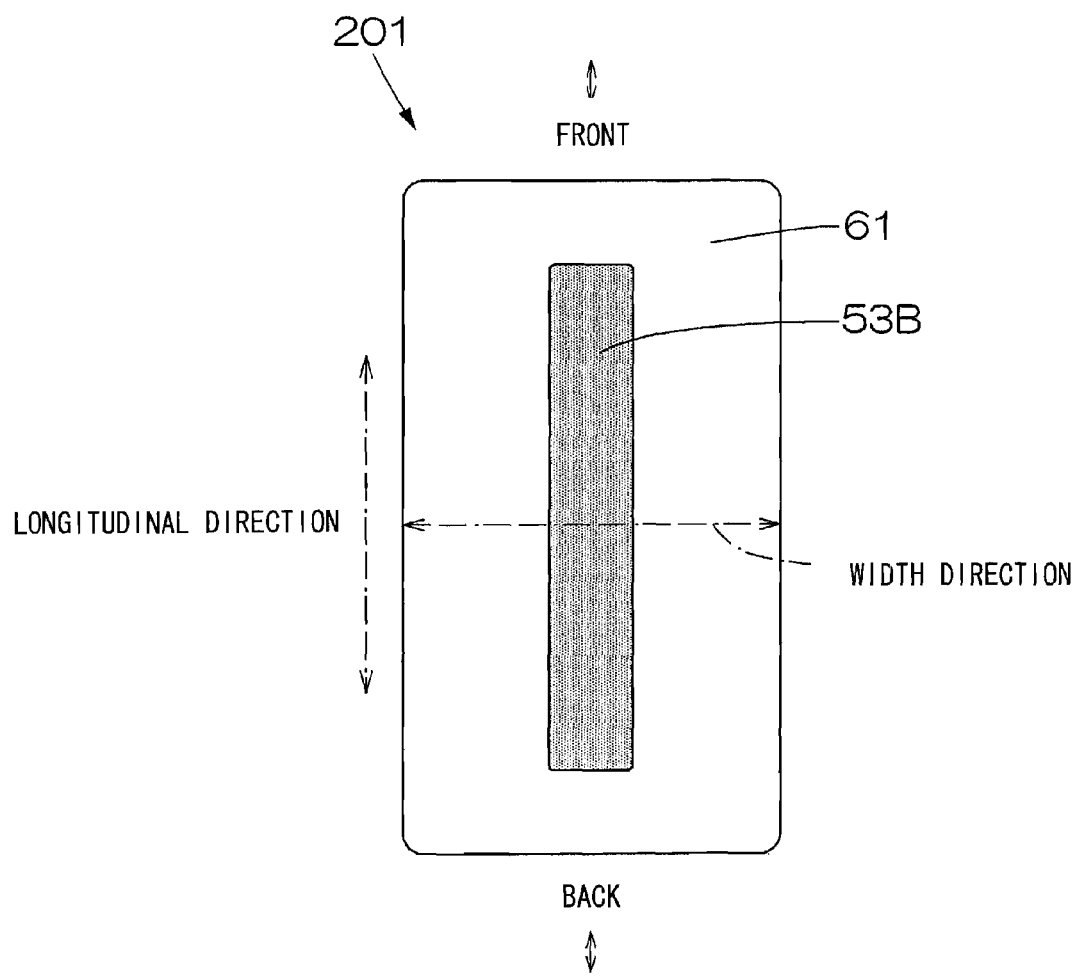
FIG. 44 is a plan view schematically showing the embodiment of a binder added absorbent member, on which another absorbent member is laminated.
Figure 45:
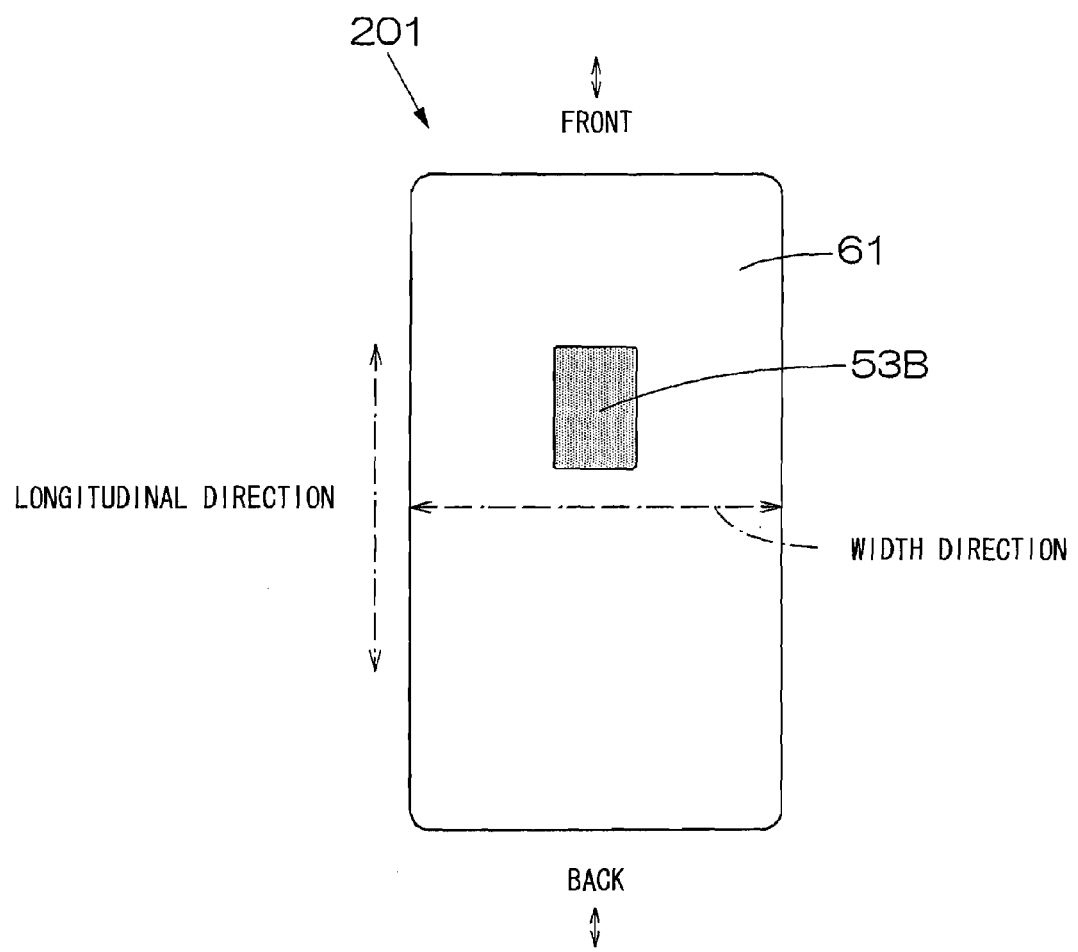
FIG. 45 is a plan view schematically showing the embodiment of a binder added absorbent member, on which another absorbent member is laminated.
Figure 46:
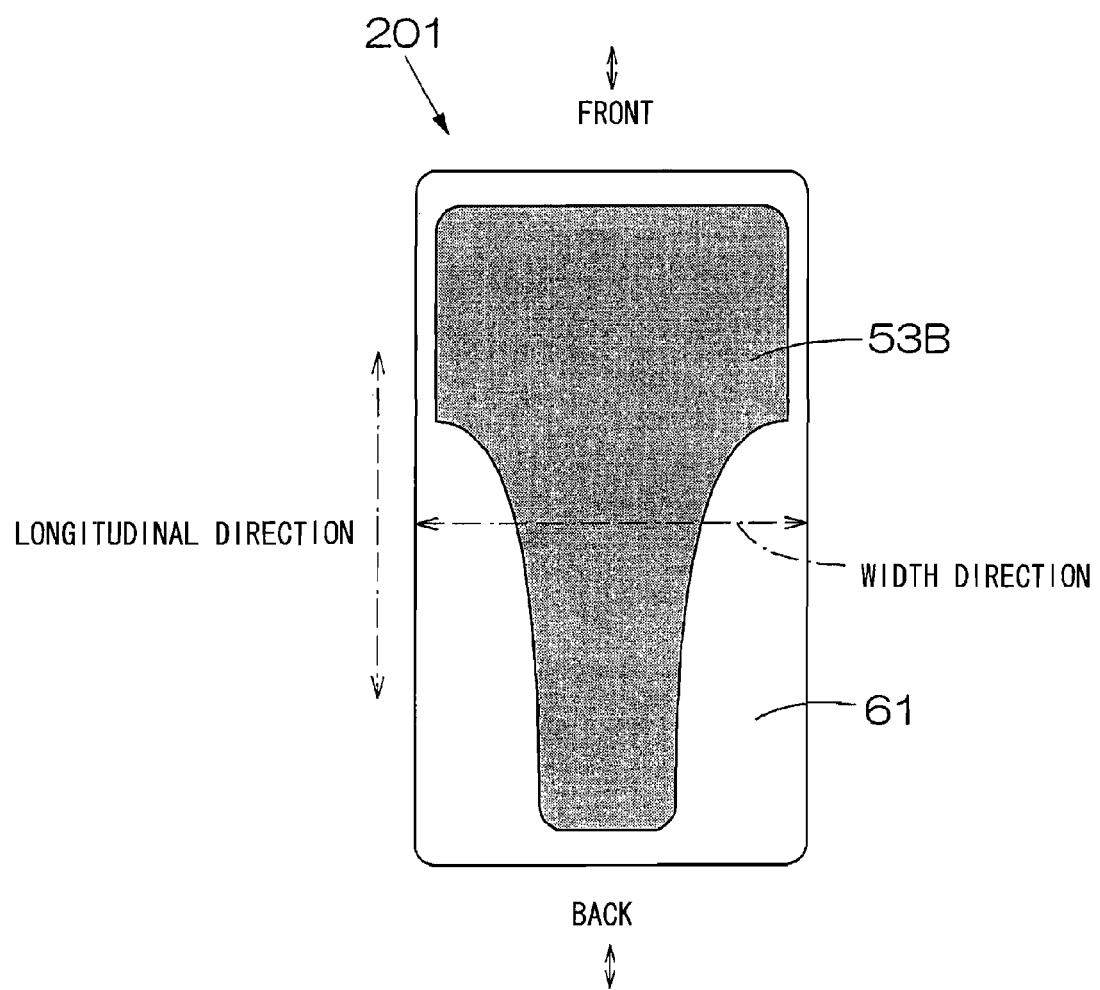
FIG. 46 is a plan view schematically showing the embodiment of a hinder added absorbent member, on which another absorbent member is laminated.

In the absorbent structure 201, the exposed area and location of the absorbent member 53B can be changed desirably in design according to the actual application. For example, it may be changed according to its configuration in the absorbent article. On the plan view seen from the wearer-side, the absorbent member 53B may be preferably configured in the following. First, as shown in FIG. 44, the absorbent member 53B is disposed at the middle portion in the width direction so as to extend along the longitudinal direction. Next, as shown in FIG. 45, the absorbent member 53B is disposed on the restricted spot zone corresponding to the wearer's excretory organ. Then, as shown in FIG. 46, the absorbent member 53B is wide at its front portion while it is narrow at its back portion. Finally, the absorbent structure 201 is incorporated into a sanitary napkin so that the longitudinal direction of the absorbent member 53B corresponds to the longitudinal direction of the sanitary napkin. In this sanitary napkin, due to such configuration, the assembly of fibers is easily adapted to locate in only the zone near the wearer's excretory organ. Accordingly, the inexpensive material can be used for the rest of the absorbent article, resulting in the low producing cost.

In the absorbent structure 202, the absorbent member 53B and the other absorbent member 61 are laminated in the above stated manner. In this case, embossing may be carried out on the absorbent structure 202 as shown in FIGS. 47 to 52.

The location of embossing is not specifically limited. However, it is preferable that emboss e is formed not on the absorbent member 53B but on the wearer-side surface of the absorbent member 61, because, if the embossing is carried out on the absorbent member 53, there is fear that the pressing decreases the capacity with which the absorbent member 53 remains the body fluid. It is more preferable that the absorbent member 61, which is disposed on the under surface of the absorbent member 53B, is formed so as to be larger than the absorbent member 53B in the width and length, and then, the embossing is carried out on the wearer-side exposed face (on which, the absorbent member 53B is not superimposed,) of the absorbent member 61.

Figure 47:
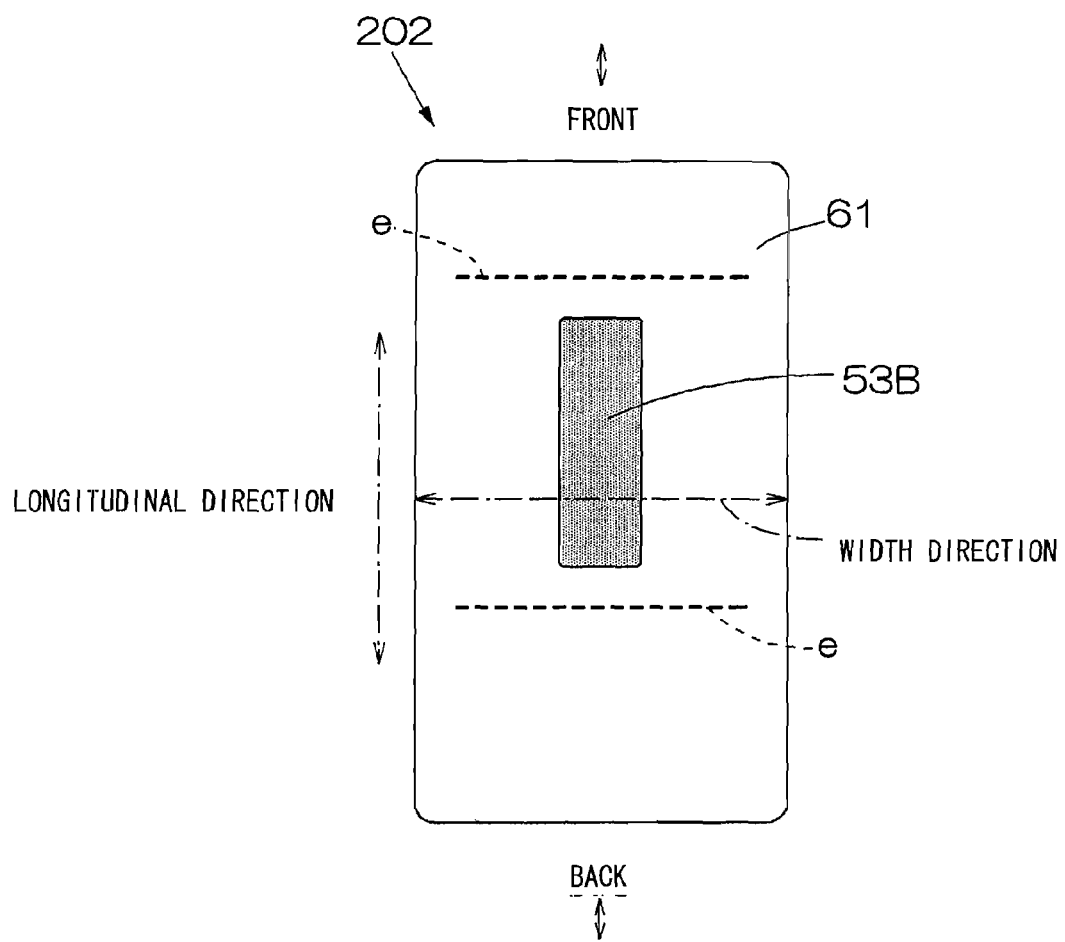
FIG. 47 is a plan view schematically showing the embodiment of a binder added absorbent member, on which another embossed absorbent member is laminated.
Figure 48:
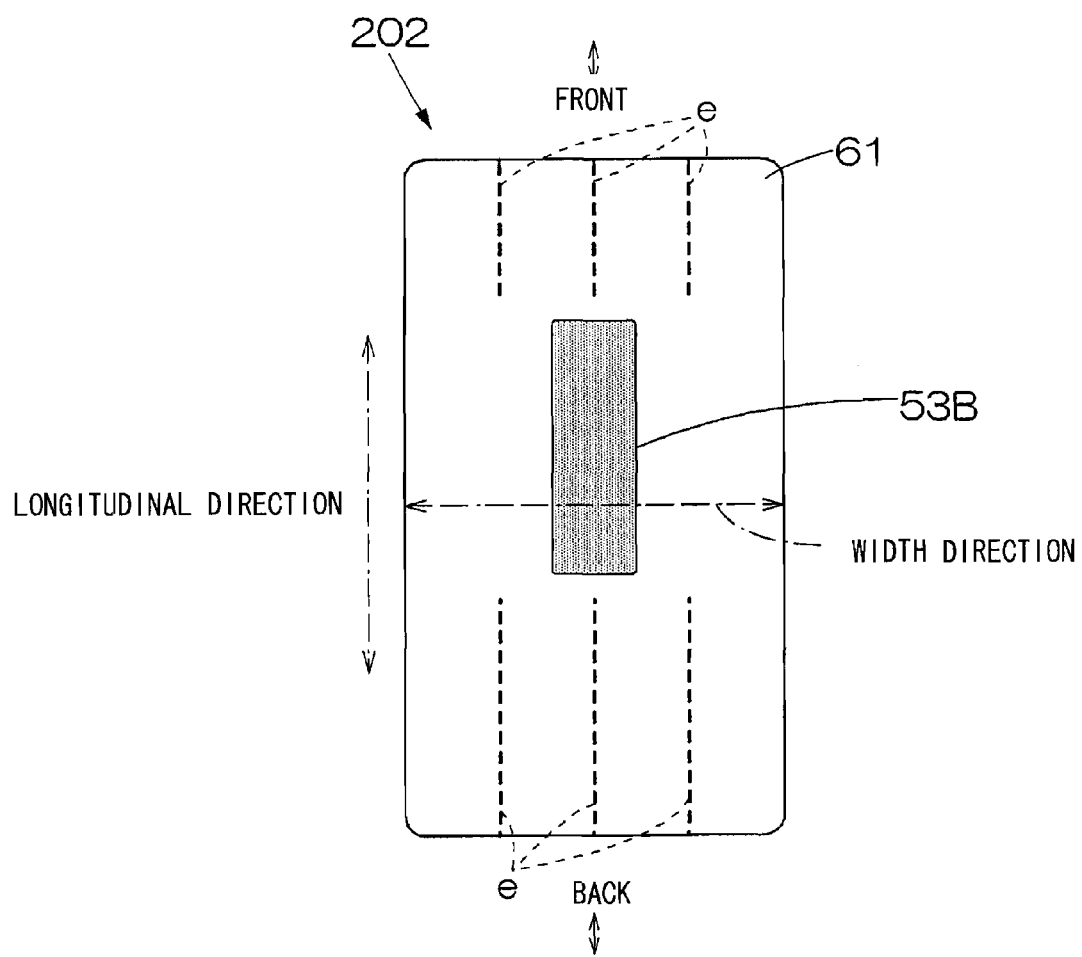
FIG. 48 is a plan view schematically showing the embodiment of a binder added absorbent member, on which another embossed absorbent member is laminated.
Figure 49:
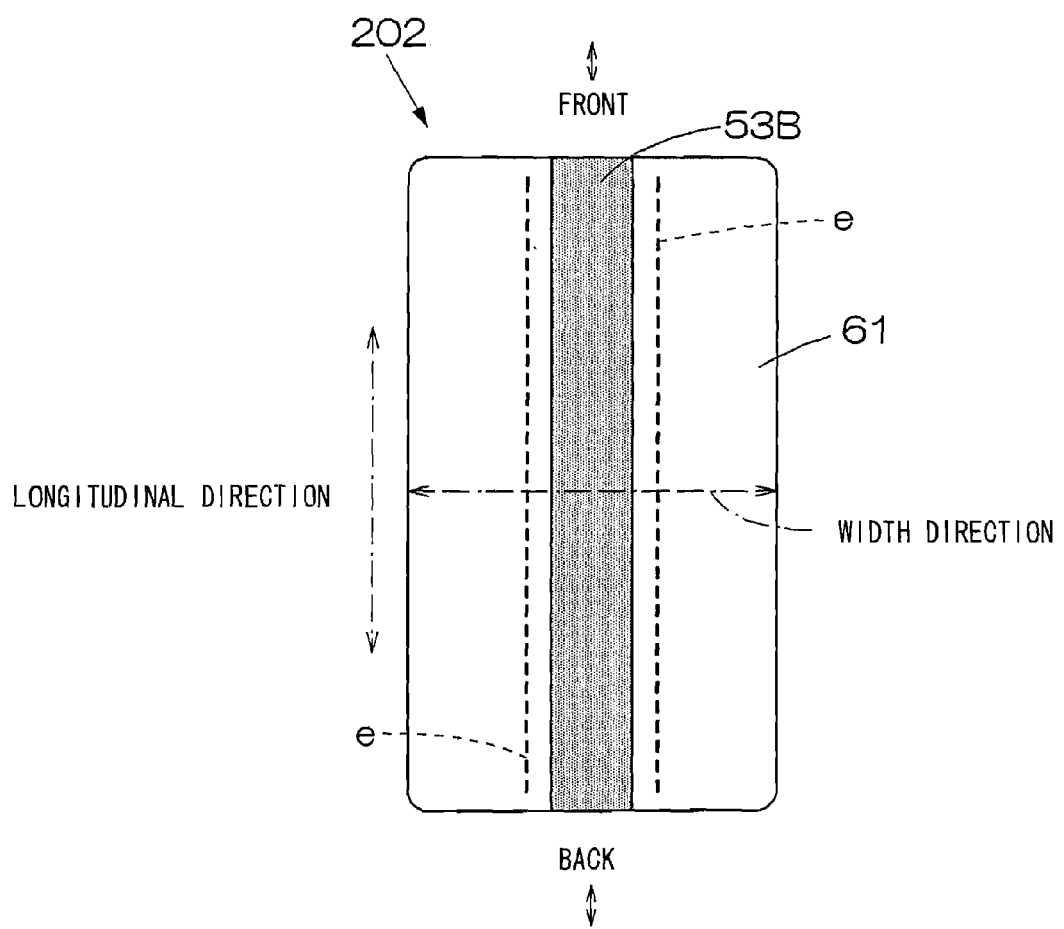
FIG. 49 is a plan view schematically showing the embodiment of a binder added absorbent member, on which another embossed absorbent member is laminated.
Figure 50:
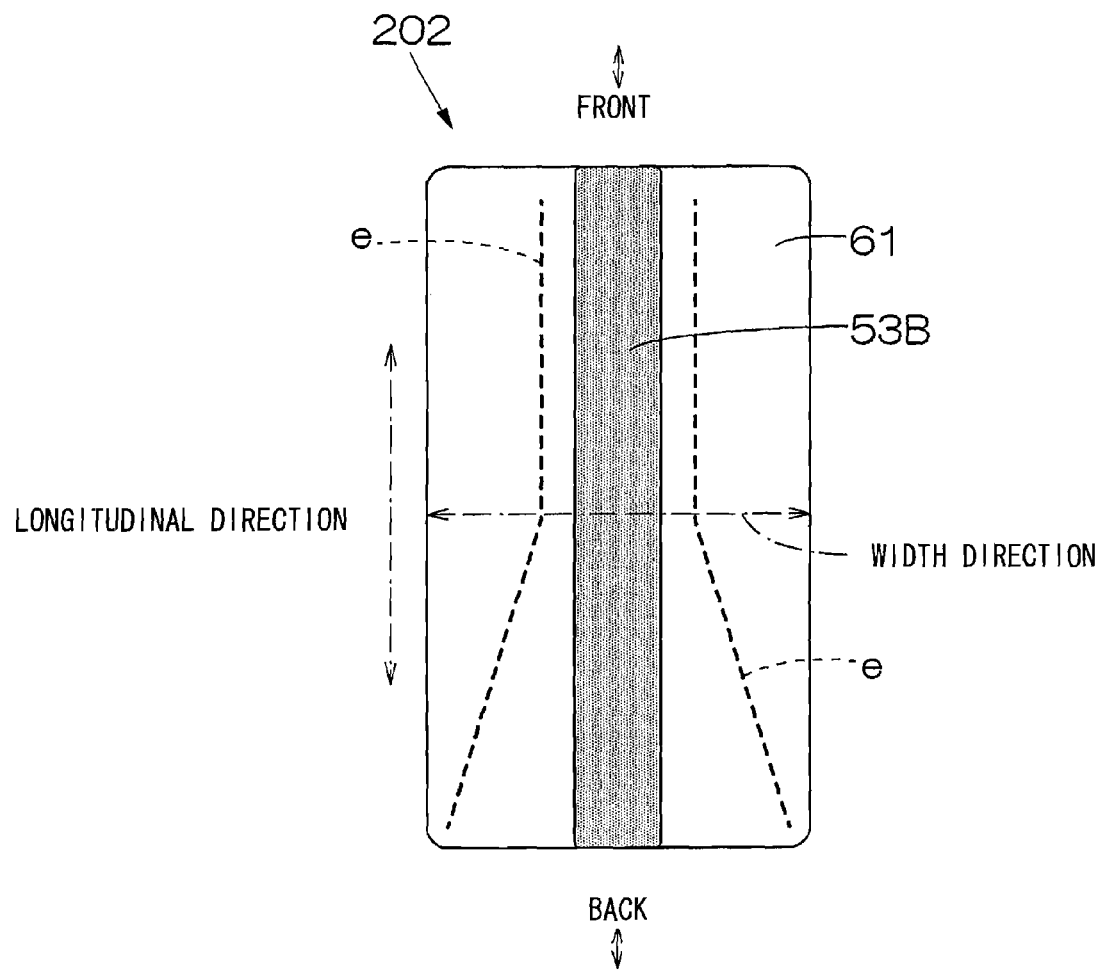
FIG. 50 is a plan view schematically showing the embodiment of a binder added absorbent member, on which another embossed absorbent member is laminated.

The preferable examples of the absorbent structure 202 on which, the embossing is carried out, will be stated in the following. First, as shown in FIG. 47, the absorbent member 53B is located on the restricted spot zone, then, embossing e is formed on the absorbent member 61 in its width direction in the form of line at the front and at the back of the absorbent member 53B. Next, as shown in FIG. 48, the absorbent member 53B is located on the restricted spot zone, then, embossing e is formed on the absorbent member 61 in its longitudinal direction in the form of plural lines at the front and at the back of the absorbent member 53B. Subsequently, as shown in FIG. 49, the absorbent member 53B is located on the middle portion in the width direction of the absorbent structure 202 so as to extend in the longitudinal direction, then, embossing e is formed on the absorbent member 61 in its longitudinal direction in the form of line at the right and at the left of the absorbent member 53B. Finally, as shown in FIG. 50, the absorbent member 53B is located on the middle portion in the width direction of the absorbent structure 202 so as to extend in the longitudinal direction, then, embossing e is formed on the absorbent member 61 in the form of line descending vertically from the front end of the absorbent structure 202 to the intermediate portion and continuously descending outwardly at the right and at the left of the absorbent member 53B.

Thus embossed absorbent structure 202 is incorporated into e.g., a sanitary napkin so that the longitudinal direction of the absorbent structure 200 corresponds to the longitudinal direction of the sanitary napkin. In this way, the absorbent member 53B can be easily located at the zone near the wearer's excretory organ, for example, the zone into which discharged menstrual blood is absorbed, and besides, the body fluid discharged to the absorbent member 53B can be diffused along the embossing e. Consequently, this absorbent article can offer protection against the side leakage.

Further, in incorporating the absorbent structure 202 into an absorbent article, a body fluid permeable sheet, so called second sheet may be interposed between the absorbent structure 202 and the body fluid permeable face sheet 51. In this case, embossing e is applied on the second sheet and the absorbent structure 202 integrally.

Figure 51:
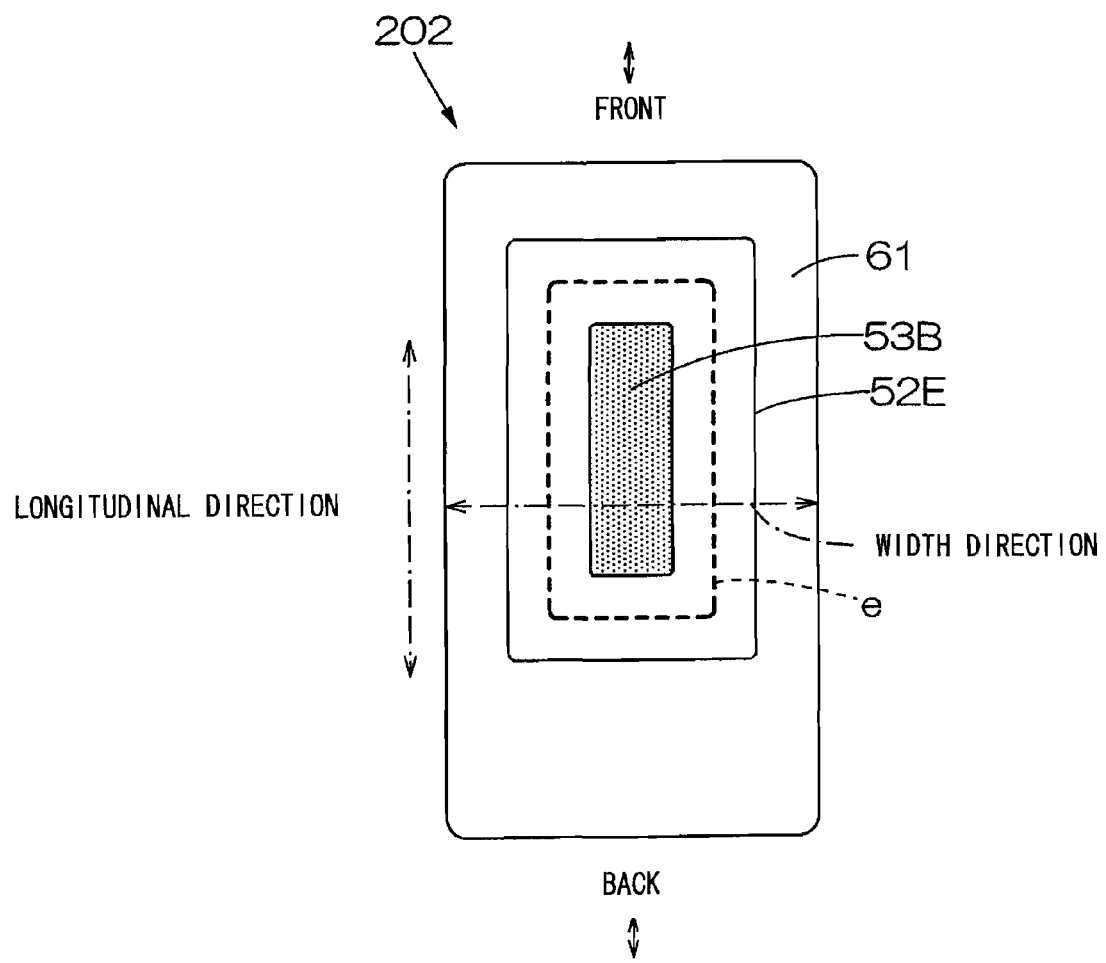
FIG. 51 is a plan view schematically showing the embodiment of a binder added absorbent member, on which another embossed absorbent member is laminated.
Figure 52:
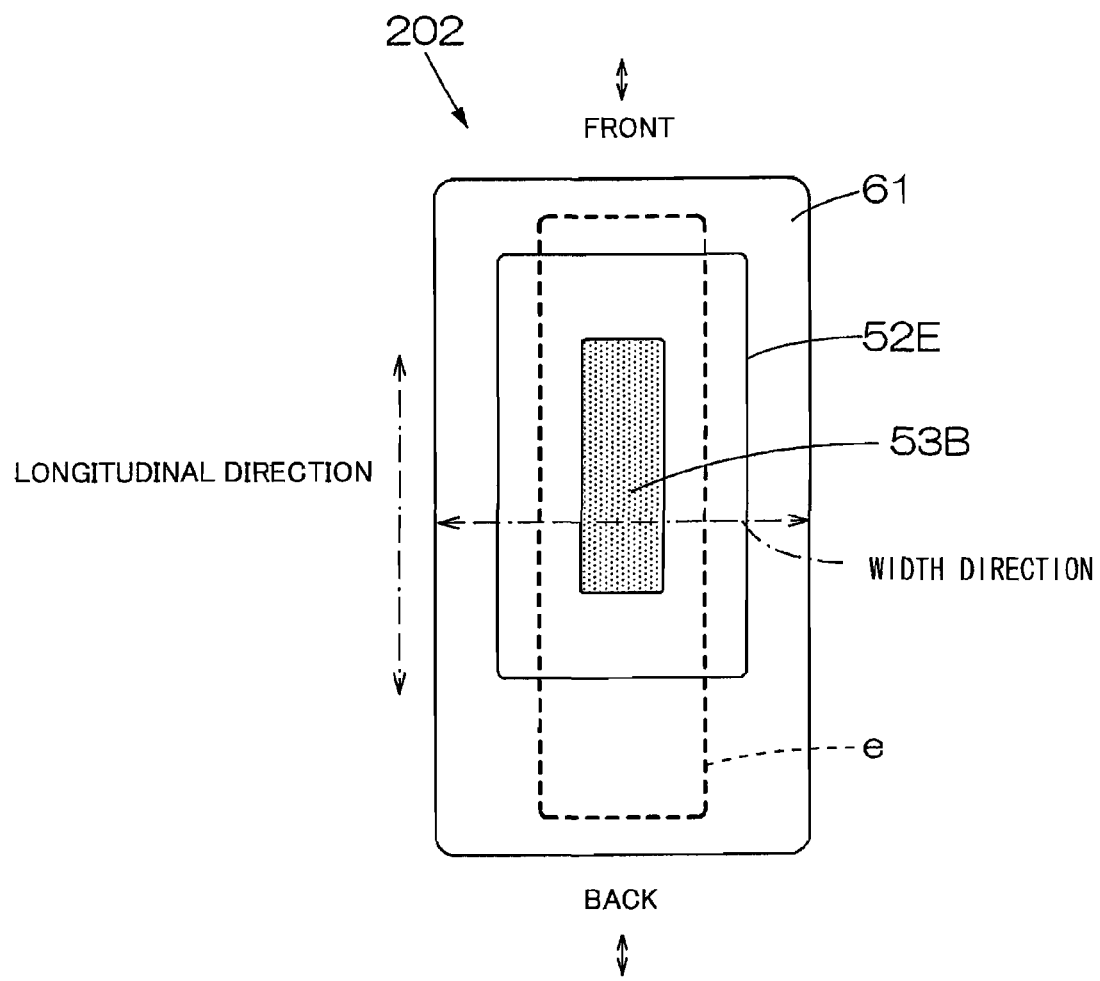
FIG. 52 is a plan view schematically showing the embodiment of a binder added absorbent member, on which another embossed absorbent member is laminated.

For example, as shown in FIGS. 51 and 52, in each embodiment, it is preferable that the wearer-side surface of the absorbent member 53B, which is located at the restricted spot zone, is covered with the second sheet 52E, and embossing is carried out on the second sheet 52E and the absorbent member 61 integrally so that the embossing e surrounds the absorbent member 53B in the form of square. In each embodiment, the second sheet 52E and the absorbent structure 202 can be integrated surely, the resultant absorbent article offers preferably protection against the side leakage on account of the embossing as well as the prevention against the reversing of the body fluid on account of the second sheet 52E.

Figure 53:
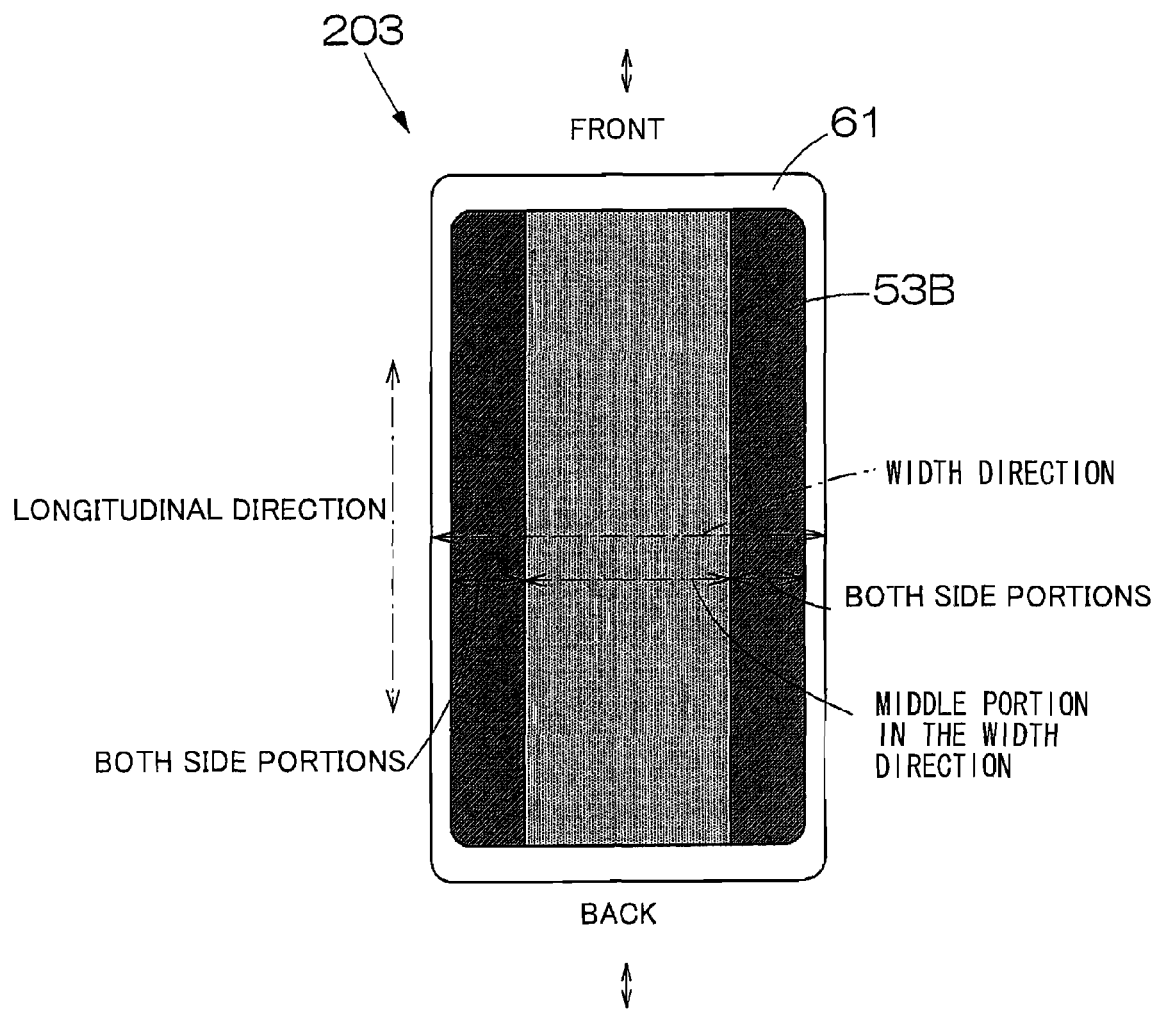
FIG. 53 is a plan view schematically showing the embodiment of a binder added absorbent member, on which another absorbent member is laminated.

In the absorbent member of the embodiments shown in the plan views of FIGS. 43 to 52 from the wearer-side, the binder is added uniformly to the whole of assembly of fibers. Then, each assembly of fibers shown in FIGS. 33 to 42 can be used also in this absorbent structure 202. For example, as shown in FIG. 53, in the absorbent structure 203, the absorbent member 61 is disposed under surface of the absorbent member 53B including the assembly of fibers. In this assembly, the adhesion degrees or fusion degrees of the fibers at the both side portions in the width direction is stronger than that at the middle portion in the width direction by adjusting the added amount of binder to the both side portions so as to be larger than the added amount of binder to the middle portion. Here, the absorbent member 61 holds the thickness of the absorbent structure 203.

As the absorbent material other than tow, there can be listed a pulp fiber, porous foam, a cotton fiber, a non-woven fabric and the like.

When the pressure is applied by e.g., the wearer to the absorbent article, the thickness of the absorbent member 53B is decreased. In this situation, the absorbent structure loses its stiffness. In the above laminated absorbent structure, the thickness of the absorbent member 61 is also decreased under and after the application of the pressure. However, by using the material for the absorbent member 61 so that the decrease in its thickness is lower than that of the absorbent member 53B, since the absorbent member 61 is laminated on the under surface of the absorbent structure, the decrease in the thickness of the absorbent member 53B can be complemented by the absorbent member 61, which offers stiffness. As a result, the absorbent structure can offer stiffness even under the pressure as well as when the body fluid is retained in the absorbent member 53B.

The dimension of decrease in thickness can be expressed by work of compression (WC). If the work of compression (WC) is low, under and after the application of pressure, the dimension of decrease in thickness is low and the stiffness is offered. On the other hand, if the work of compression (WC) is high, under and after the application of pressure, the dimension of decrease in thickness is high and the stiffness is easily lost. The work of compression (WC) can be measured, for example, with Handy-Type Compression Tester (KES-G5: KATO TECH CO., LTD.). Concretely, it can be measured with this tester, specimen size and shape: 200 mm long×50 mm wide and square, measured position: the center of the specimen of 200 mm long×50 mm wide, measuring conditions: SENS: 2, Type of Force Sensor: 1 kg, SPEED RANGE: 0.1, DEF Sensitivity: 20, Pressurization Area: 2 $cm^2$, Sampling Rate: 0.1 (Standard), STROKE SET: 5.0, Maximum Weighting: 50 $gf/cm^2$. When this absorbent structure is used as an absorbent article, the work of compression (WC) of the absorbent member 61 is preferably 1.0 to 3.0 $gf \cdot cm/cm^2$, while the work of compression (WC) of the absorbent member 53B is preferably 4.0 to 10.0 $gf \cdot cm/cm^2$. These values can be attained easily by using the fibers in tows having the fiber density of 10 to 100 $kg/m^3$ and the other absorbent member 61 having the density of 10 to 100 $kg/m^3$.

It is possible that the plural absorbent members 53B are laminated in the absorbent structure 204. The concrete embodiments will be explained by way of cross sections FIGS. 54 to 57. In these drawings, the face sheet 51 and back sheet 54 are illustrated for convenience with the dotted lines. However, these sheets 51, 54 are not included in the absorbent structure 204.

Figure 54:
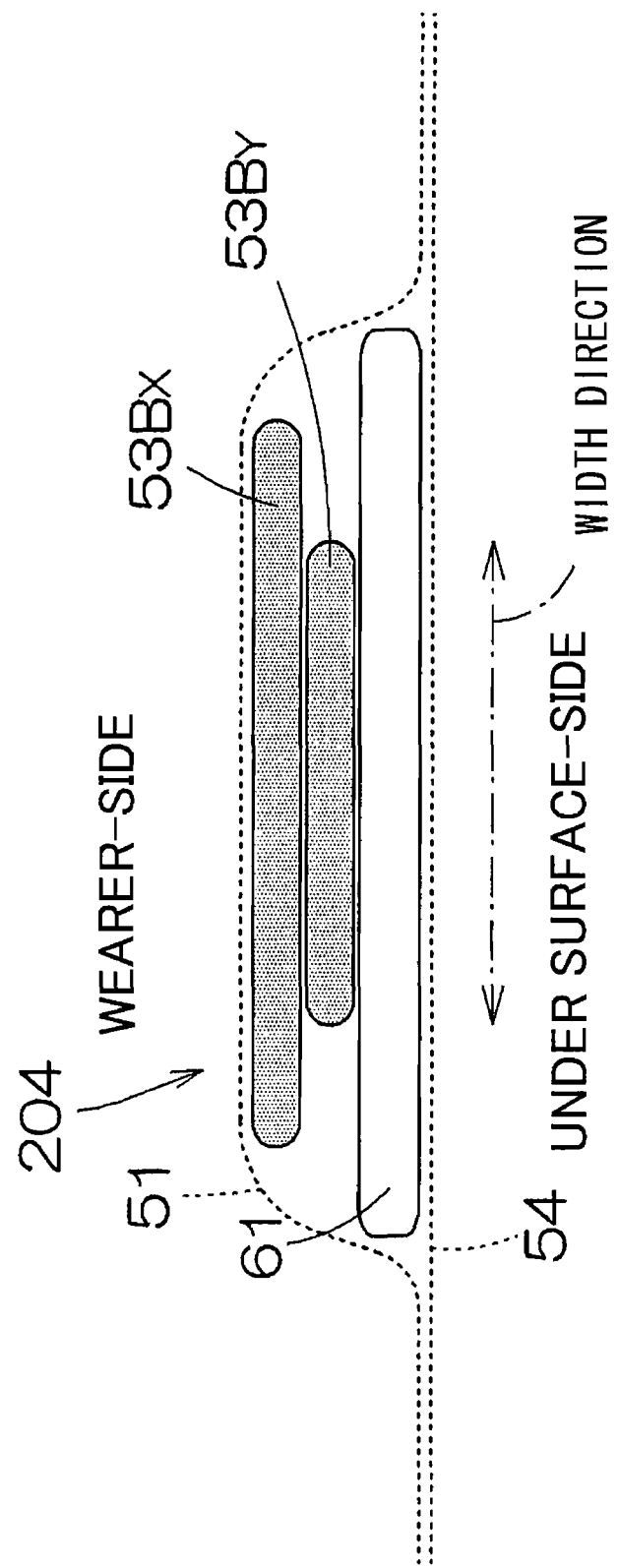
FIG. 54 is a plan view schematically showing the embodiment of binder added absorbent members.
Figure 55:
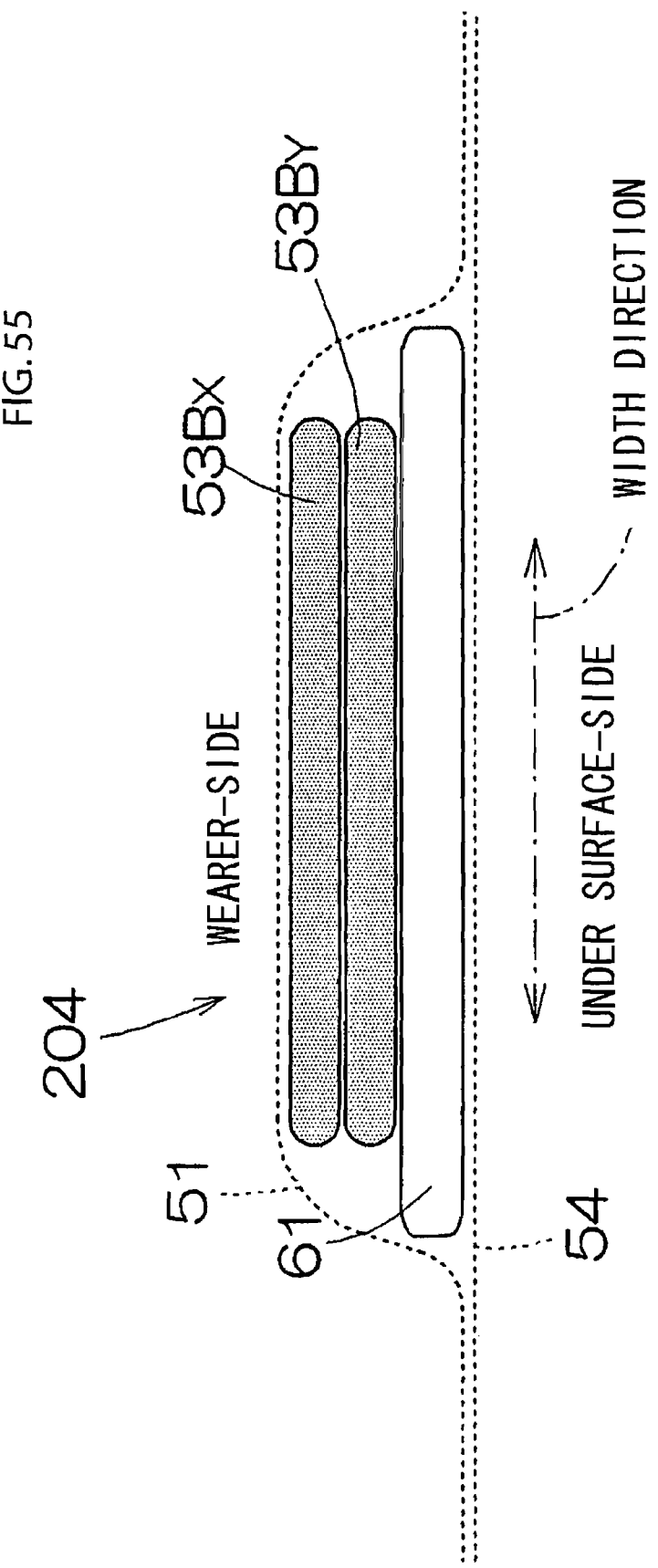
FIG. 55 is a plan view schematically showing the embodiment of binder added absorbent members.
Figure 56:
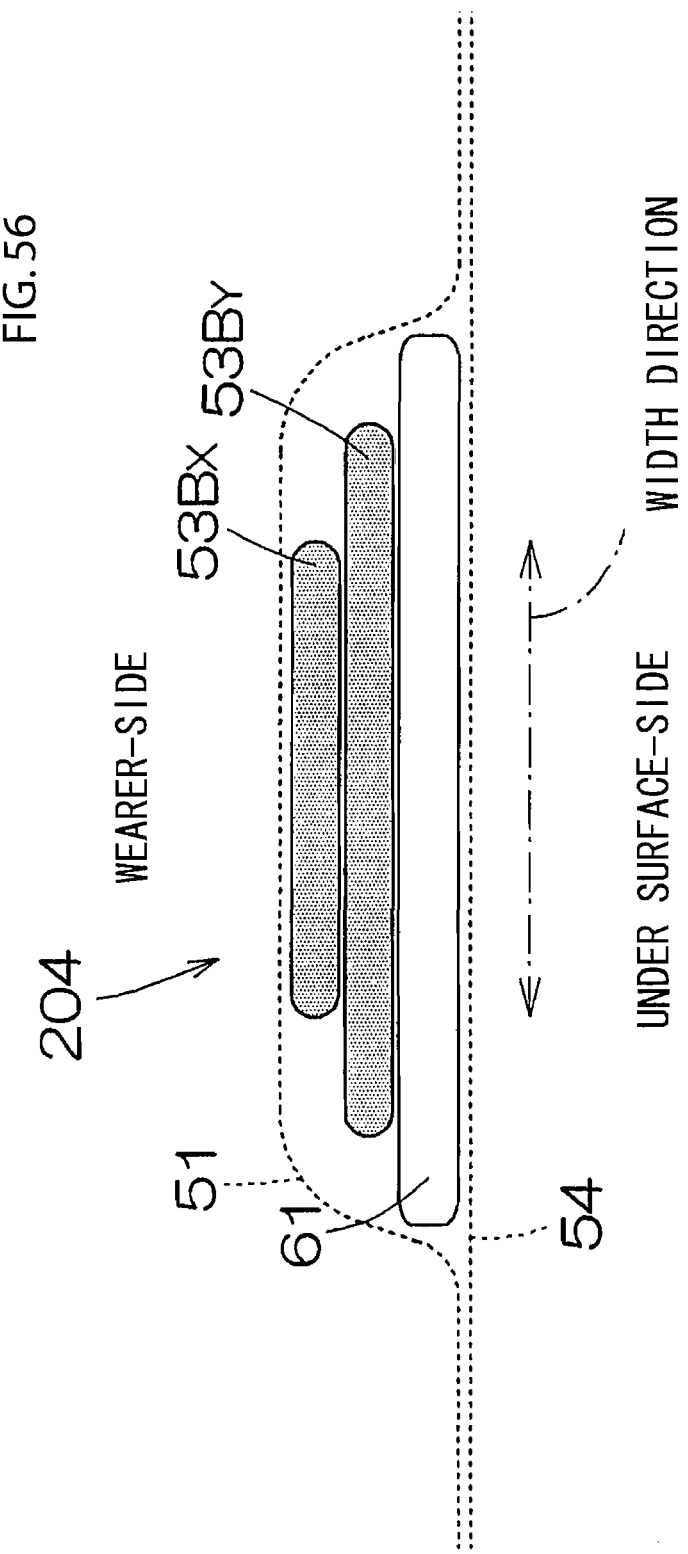
FIG. 56 is a plan view schematically showing the embodiment of binder added absorbent members.
Figure 57:
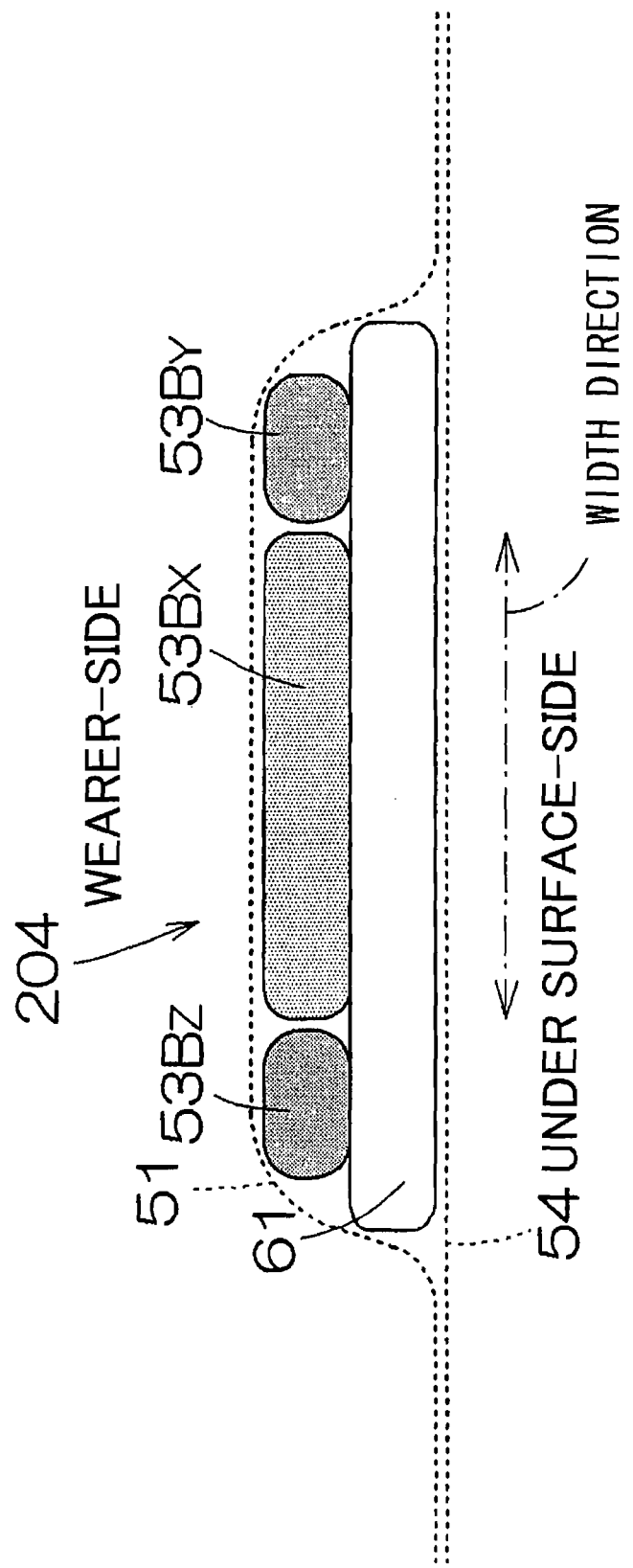
FIG. 57 is a plan view schematically showing the embodiment of binder added absorbent members.

There are some embodiments as stated below. First, as shown in FIG. 54, the absorbent member $53B_X$ disposed on the wearer-side is larger in width than the absorbent member $53B_Y$ disposed on the under surface-side. Next, as shown in FIG. 55, the absorbent member $53B_X$ disposed on the wearer-side is the same in width as the absorbent member $53B_Y$ under and after the application of pressure. Finally, as shown in FIG. 56, the absorbent member $53B_X$ disposed on the wearer-side is smaller in width than the absorbent member $53B_Y$ disposed on the under surface-side. In the absorbent structure 204 including the plural absorbent members $53B_X$, $53B_Y$, besides the width, the added amount of binder, density, bulk, width, denier of the constituent fiber and the like can be different each other if desired. Further, as shown in FIG. 57, plural absorbent members $53B_X$, $53B_Y$, $53B_Z$ can be disposed separately side by side in the width direction of the absorbent structure 204. Also in this case, the density, added amount of binder, bulk, width, denier of the constituent fiber and the like can be designed desirably so that they are different among the absorbent members $53B_X$, $53B_Y$, $53B_Z$. For example, the larger amount of binder may be added to the absorbent members $53B_Y$, $53B_Z$ located at the both side portions in the width direction for the stronger fiber bonding, while the smaller amount of binder may be added to the absorbent member $53B_X$ located at the middle portion in the width direction for the weaker fiber bonding.

In laminating the plural absorbent members $53B_X$, $53B_Y$ illustrated in FIGS. 54 to 56, as shown in FIG. 30, the belt-shaped absorbent members $53B_X$, $53B_Y$ are fed down at an angle and fed up at an angle, respectively and inserted between the roll R1-roll R1 and the roll R2-roll R2 for their laminating. After that, the laminated absorbent members 53B may be sized desirably by e.g., cutting. On the other hand, in disposing the plural absorbent members separately in the width direction illustrated in FIG. 57, as shown in FIG. 32, the belt-shaped absorbent members $53B_X$, $53B_Y$, $53B_Z$ are gathered with several rollers R3 to R6. After that, the disposed absorbent members 53B may be sized desirably by e.g., cutting.

The absorbent article comprising the stated absorbent structure and the producing method thereof will be explained by way of examples of sanitary napkins.

Figure 58:
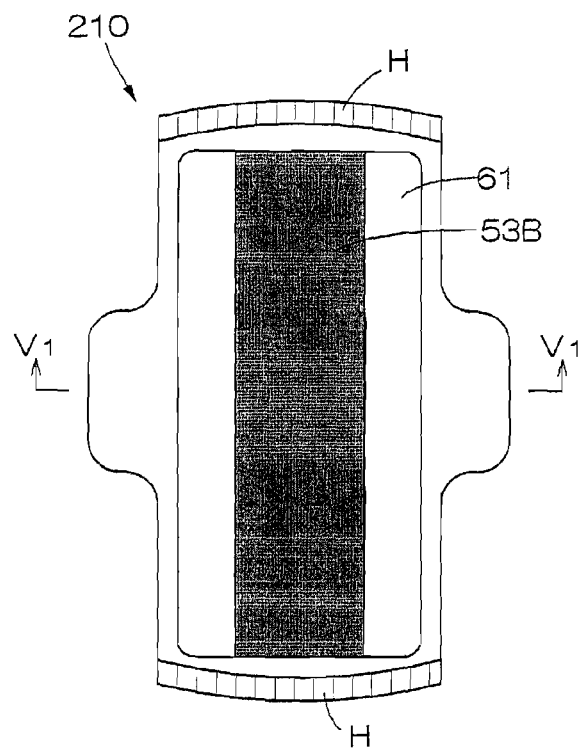
FIG. 58 is a plan view schematically showing the first embodiment of a sanitary napkin.
Figure 59:
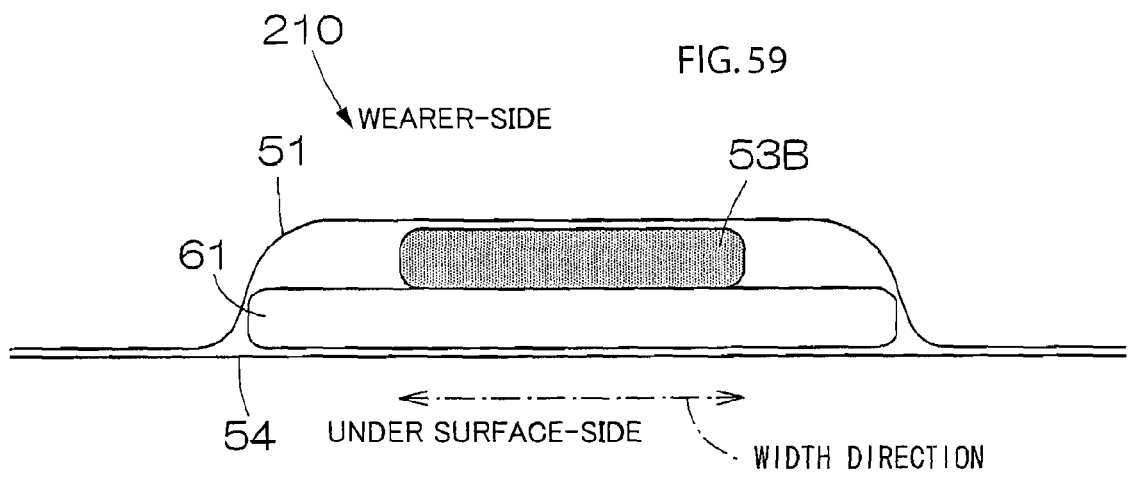
FIG. 59 is a cross section schematically showing the first embodiment of a sanitary napkin

The first embodiment of sanitary napkin 210 is shown in FIGS. 58 and 59. In the first embodiment of sanitary napkin 210, as shown in the plan view, FIG. 58 seen from the wearer-side, both the absorbent member 53B and the other absorbent member 61 are extended longitudinally without reaching the front end and the back end of the sanitary napkin 210. As shown in FIG. 59, which is the cross section of FIG. 58 taken on the line $V_1$-$V_1$, in this first example, the absorbent member 61 and the absorbent member 53B are laminated and at the same time, the absorbent member 53B is disposed on the wearer-side.

The producing method of the sanitary napkin 210 of this embodiment is shown in FIG. 20. First, adhesive is coated with the applicator 21 on the suitable portions of the wearer-side surface of the belt-shaped absorbent member 61, which is made of e.g., fiber laminating pulp and which is fed downwardly with e.g., a belt conveyor. Next, the belt-shaped absorbent member 53B, to which binder is previously added, is continuously laminated and adhered to the absorbent member 61. Then, the resultant belt-shaped and laminated absorbent structure 210 is sized desirably with the cutters 22 to be absorbent structures 210, 210 . . . , which are further fed downwardly. After that, these absorbent structures 210, 210 . . . are fed downwardly with e.g., a belt conveyor while the belt-shaped top sheet 51 is superimposed on their upper surfaces (the wearer-side surfaces) and the belt-shaped back sheet 54 is superimposed on their under surfaces. Subsequently, the belt-shaped face sheet 51 and the belt-shaped back sheet 54 are adhered with the heat sealers 26 at the adhesion points H, which are spaced desirably. Finally, these absorbent structures are cut at these adhesion points H, thus each sanitary napkin 210 can be obtained separately. Each adhesion point H defines the end of the sanitary napkin in its longitudinal direction.

Figure 60:
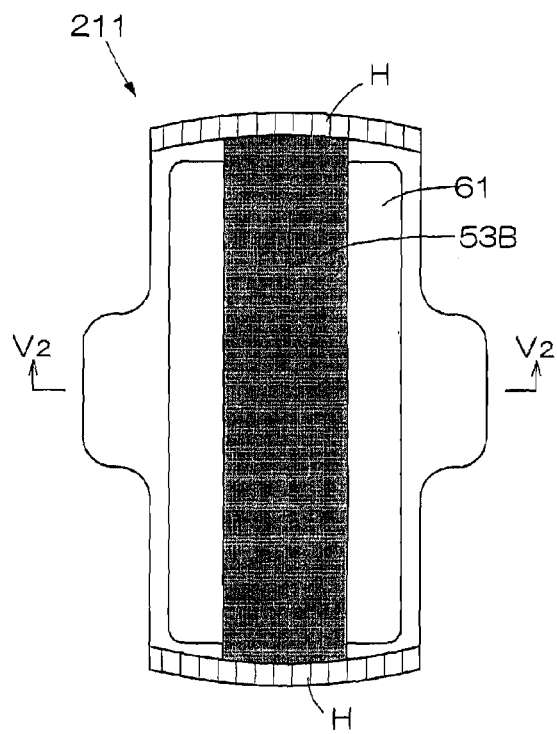
FIG. 60 is a plan view schematically showing the second embodiment of a sanitary napkin.
Figure 61:
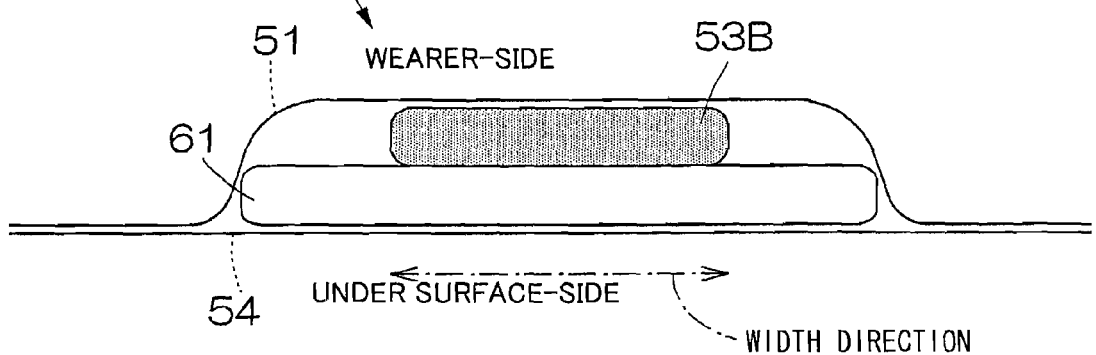
FIG. 61 is a cross section schematically showing the second embodiment of a sanitary napkin.

The second embodiment of the sanitary napkin 211 is shown in FIGS. 60 and 61. As shown in the plan view, FIG. 60 seen from the wearer-side, the absorbent member 61 is extended longitudinally without reaching the front end and the back end of the sanitary napkin of the second embodiment, while the absorbent member 53B is extended longitudinally so as to reach these both ends. As shown in FIG. 61, which is the cross section of FIG. 60 taken on the line $V_2$-$V_2$, the absorbent member 61 and the absorbent member 53B are laminated and at the same time, the absorbent member 53B is disposed on the wearer-side.

The producing method of the sanitary napkin 211 of this embodiment is shown in FIG. 23. First, the belt-shaped absorbent member 61 made of e.g., airformed pulp, which is fed downwardly with e.g., a belt conveyor, is sized desirably with the cutters 22 to be the absorbent members B, B . . . , which are further fed downwardly. Next, adhesive is coated with the applicator 21 on the suitable portions of the wearer-side surface of each absorbent member 61. Then, the belt-shaped absorbent member 53B, to which binder is previously added, is continuously laminated so as to adhere to the absorbent members 61, 61 . . . . Also during such lamination, they are further fed downwardly. After that, while the belt-shaped absorbent structure 211, which is defined by the absorbent member 61, 61 . . . laminated by the belt-shaped absorbent member 53B, is fed downwardly, the belt-shaped face sheet 51 is superimposed on the upper surface (wearer-side surface) of this absorbent structure 210 and the belt-shaped back sheet 54 is superimposed on the under surface of the absorbent structure 211. Subsequently, the belt-shaped face sheet 51 and the belt-shaped back sheet 54 are adhered with the heat sealers 26 at the adhesion points H, which are spaced desirably. Finally, these absorbent structures are cut at these adhesion points H, thus each sanitary napkin 211 can be obtained separately.

Figure 62:
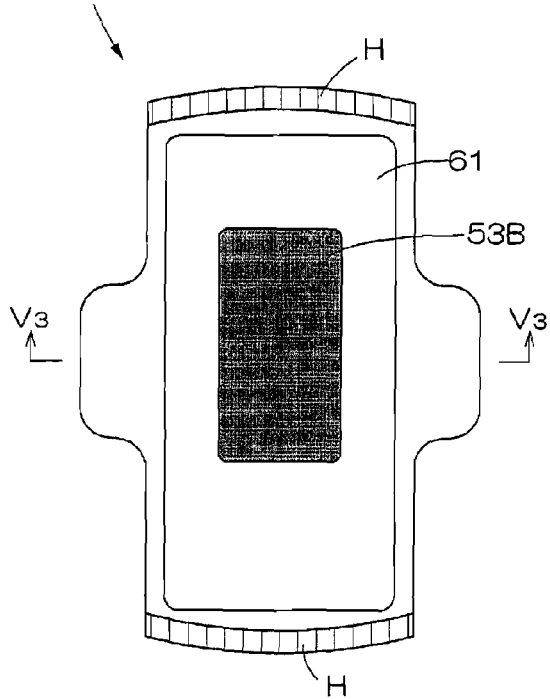
FIG. 62 is a plan view schematically showing the third embodiment of a sanitary napkin.
Figure 63:
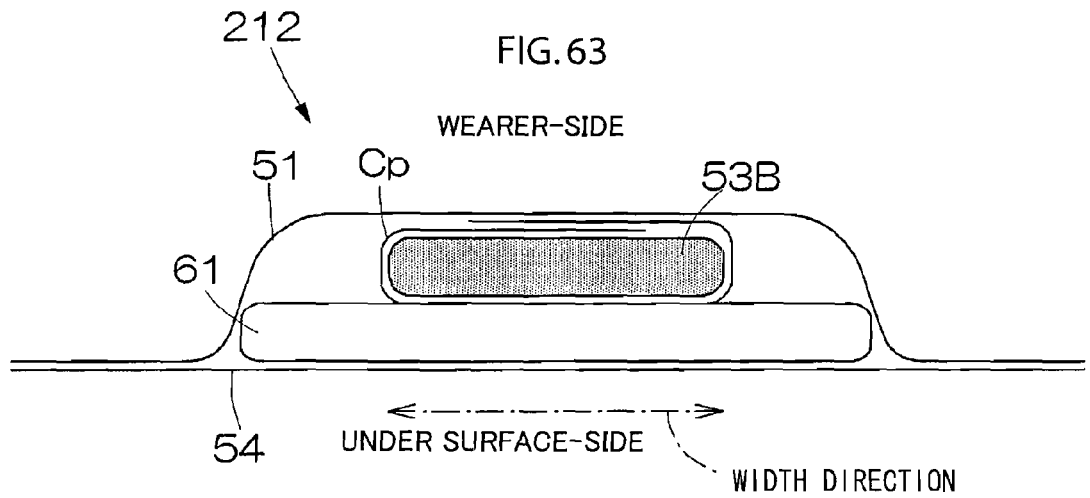
FIG. 63 is a cross section schematically showing the third embodiment of a sanitary napkin.

The third embodiment of the sanitary napkin 212 is shown in FIGS. 62 and 63. As shown in the plan view, FIG. 62 seen from the wearer-side, the absorbent member 61 is extended longitudinally without reaching the front end and the back end of the sanitary napkin 212 of the third example, while the absorbent member 53B is disposed at the restricted spot zone at the central portion of the absorbent member 61. As shown in FIG. 63, which is the cross section of FIG. 62 taken on the line $V_3$-$V_3$, in this third embodiment, the absorbent member 53B, which is wrapped with the crepe paper Cp, is laminated so as to dispose on the wearer-side surface of the absorbent structure 61.

Figure 26:
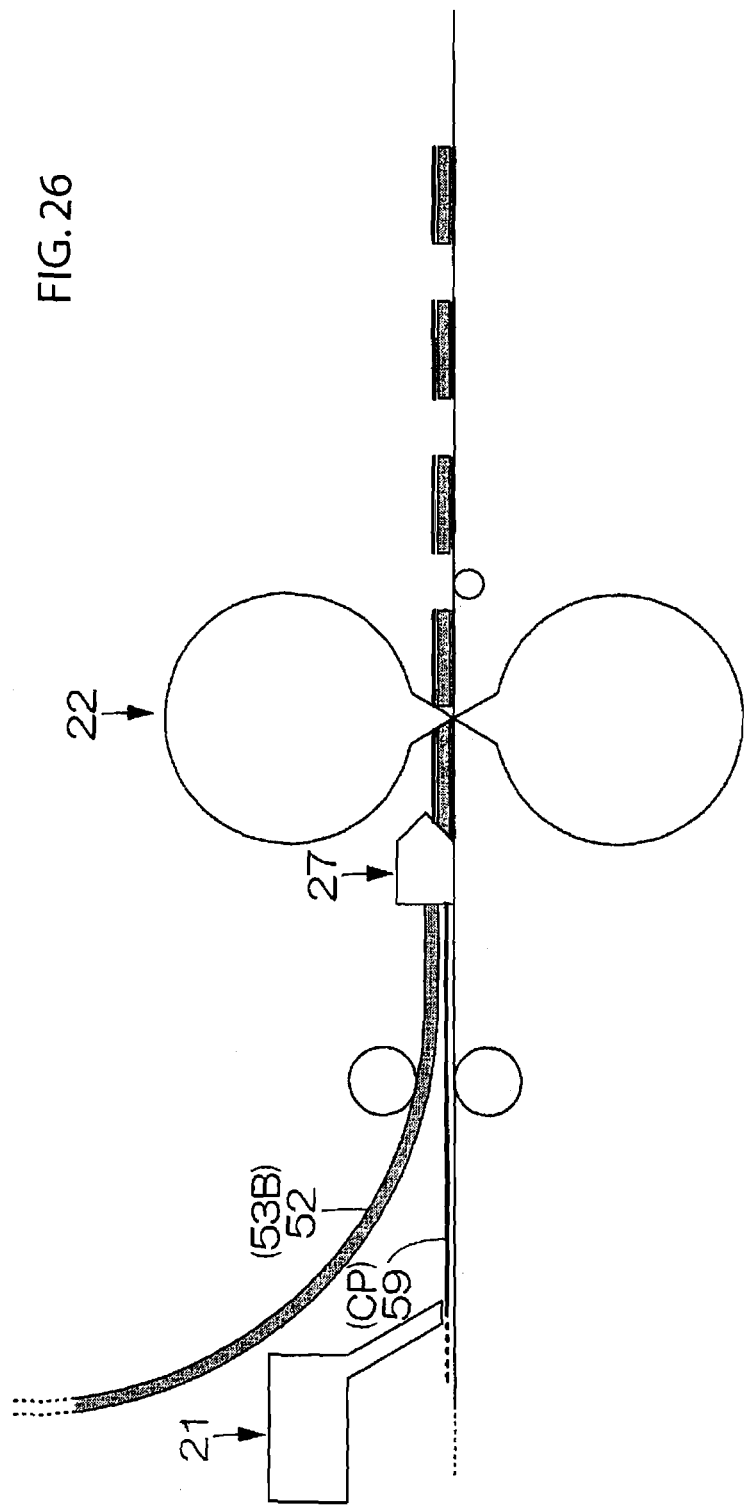
FIG. 26 is a schematic illustration showing a producing flow for covering crepe paper on an absorbent member.

The producing method of this third embodiment is partly shown in FIG. 26. First, adhesive is coated with the applicator 21 on the suitable portions of the wearer-side surface of the belt-shaped crape paper Cp, which is fed downwardly. Next, the belt-shaped absorbent member 53B, to which binder is previously added and whose width is smaller than the width of the crape paper Cp, is continuously superimposed and adhered to the crape paper. During this, the resultant absorbent member 53B adhered by the crape paper is further fed downwardly. Then, with the folding member 27, longitudinal both side portions of the crepe paper Cp are folded around the side edges of the belt-shaped absorbent member 53B so as to cover the wearer-side surface of the absorbent member 53B, resulting in the belt-shaped absorbent member 53B wrapped with the crepe paper Cp. After that, this is sized desirably with the cutter 22. Although not shown in the drawing, the resultant cut substances are disposed on the wearer-side surfaces of the absorbent members 61 having the suitable sizes. Alternatively, they are disposed on the wearer-side surfaces of the belt-shaped absorbent members 61 and after that, they are cut. Then, they are fed downwardly with a belt conveyor while the belt-shaped face sheet 51 is superimposed on the top surfaces (the wearer-side surfaces) and the belt-shaped back sheet 54 is superimposed on the under surfaces. Subsequently, the belt-shaped face sheet 51 and the belt-shaped back sheet 54 are adhered with the heat sealer at the adhesion points, which are spaced desirably. Finally, this is cut at these adhesion points H, thus each sanitary napkin 212 can be obtained individually.

[Dispersion of Super Absorbent Polymer to Assembly of Fibers in Tows]

Now, focusing the dispersion of super absorbent polymer into the assembly of fibers in tows, embodiments will be explained in the following.

FIG. 63 shows one example of the structures of pants-type disposable diapers as absorbent articles. This pants-type disposable diaper 310 comprises the outer sheet 312 disposed on the outer surface (under surface-side) and the absorbent body 320 disposed in the inner surface-side (the wearer-side) and the absorbent body 320 is fixed on the outer sheet 312. The absorbent body 320 receives, absorbs and retains body fluid such as urine, soft feces, or the like (in the case of sanitary napkin stated after, menstrual blood). The outer sheet 312 is used for putting this diaper on the wearer.

The outer sheet 312 has the shape of e.g., an hourglass as shown in the drawing with the both sides being constricted at the intermediate portion for inserting the wearer's legs. The shape of the absorbent body 320 is not specifically limited, but in the drawing, it is a rectangle.

Figure 64:
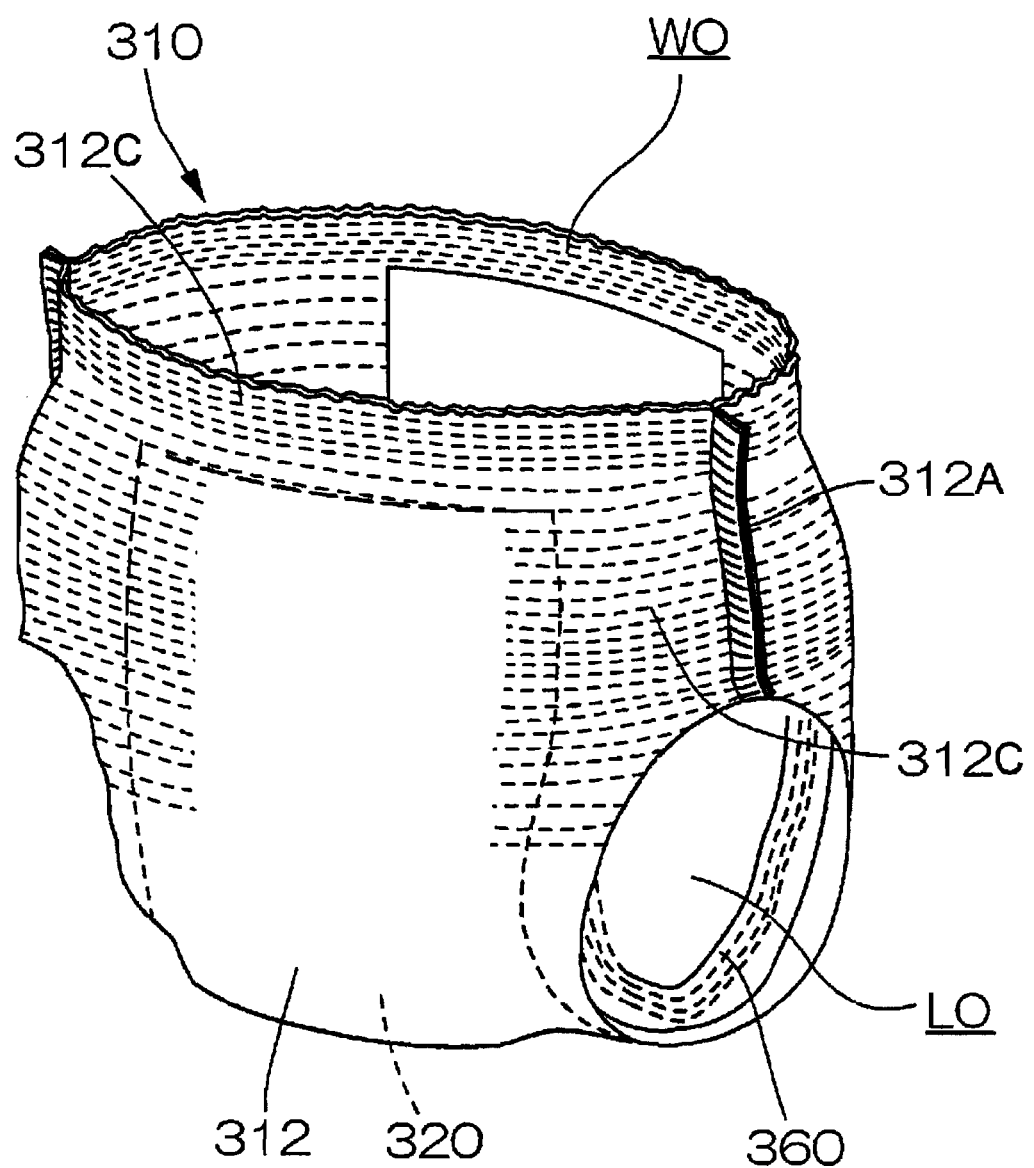
FIG. 64 is a perspective view of a pants-type disposable diaper.

As shown in FIG. 64, first, the absorbent body 320 is put on the predetermined position of the outer sheet 312 and fixed there. Next, the outer sheet 312 is folded in the longitudinal direction. Then, the joint zones 312A at the both side edges of the front body 312F and the joint zones 312A at the both side edges of the back body 312B are jointed respectively, by e.g., heat sealing. The resultant pants-type disposable diaper has the construction illustrated in FIG. 64, including the waist open WO and the pair of leg opens LO.

In the absorbent body 320 illustrated in the drawing, the middle portion, along the longitudinal direction (this longitudinal direction means the direction from the upper portion to the lower portion and also from the front portion to the back portion of the article), has the width smaller than the distance between the side edges in the constricted intermediate portion. However it is possible that the width of the middle portion can be larger than or the same as the distance in the constricted portion.

It is preferable that the outer sheet 312 comprises one pair of water repellent non-woven sheets, an elastically expansible member is disposed between these two sheets, and the contracting force of this member fits the diaper to the wearer. As the elastically expansible member, there may be rubber strand, belt-shaped elastomeric foam and so forth, and many rubber strands can be preferably used. As shown in the drawing, many lines of rubber strands 312C, 312C . . . along the width direction are continuously provided in the waist region W, are provided only at the both side portions in the under-waist region U and are not provided in the crotch region L. Since the rubber strands 312C, 312C . . . are provided so in the waist region W and the under waist region U, even if the contracting force of each rubber strand is small, the under waist region U is contacted to the wearer due to the many strands. As a result, the article is preferably fitted to the wearer.

Figure 65:
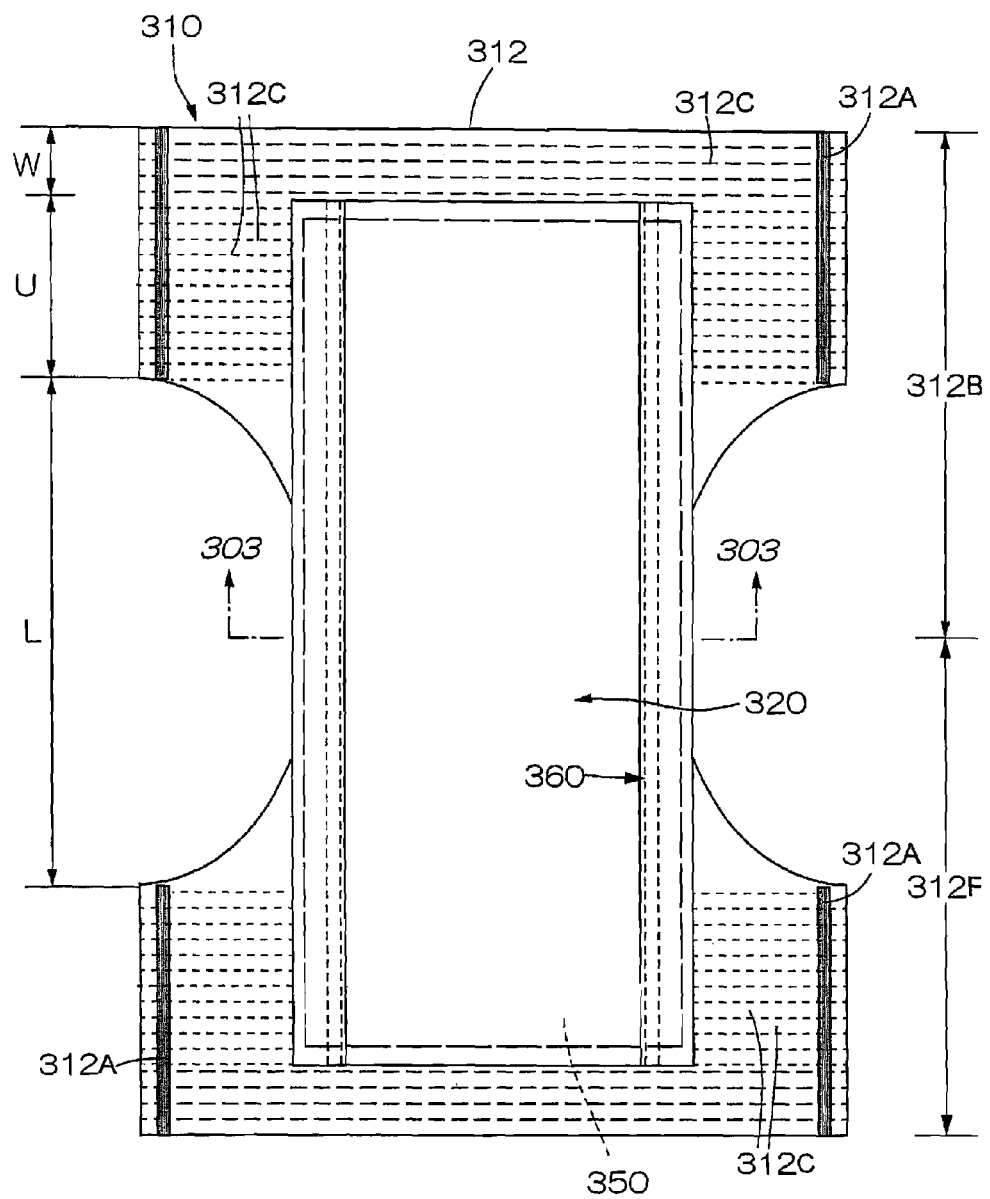
FIG. 65 is a plan view of a developed pants-type disposable diaper.

As shown in FIG. 65, the absorbent body 320 in this embodiment comprises the top sheet 330, through which the body fluid is permeable and which is made of e.g., non-woven fabric, the interposed sheet (second sheet) 340 and the absorbent element 350. Additionally, the absorbent body is provided with the barrier cuffs 360, 360 at its both sides.

The absorbent element 350 comprises the absorbent member 53B, which includes the assembly of filaments 352, 352 . . . in opened tows (It will be expressed by the assembly of fibers in tows. This is to be repeated in the following) and the super absorbent polymer particles 354, 354 . . . , and the covering sheet 358, which covers at least the under surface and the side faces of the absorbent member 53B. Additionally, the holding sheet 380 is interposed between the absorbent member 53B and under surface-side (lower) portion of the covering sheet 358.

Representatively as shown in FIG. 65, the body fluid impermeable sheet 370, which is made of e.g., a plastic sheet and called as a back sheet, is disposed in the under surface-side of the absorbent member 53B. Further, the above outer sheet 312 is disposed in the under surface-side of the body fluid impermeable sheet 370. In this embodiment, the body fluid impermeable sheet 370 is intended simply to be a sheet, which is disposed in the under surface-side of the absorbent member 53B. Then, in this embodiment shown in the drawing, between this impermeable sheet 370 and the top sheet 330, the absorbent member 53B is interposed.

The super absorbent polymer particles 354 are put into the space formed between the holding sheet 380 and the absorbent member 53B by dispersion and the like.

In dispersing and projecting the super absorbent polymer particles 354, in the subsequent steps for producing each diaper, or in the marketing channel to each consumer, it sometimes occurs that the super absorbent polymer particles 354 are passed through so as to come out from the assembly of filaments 352. In such case, the resultant assembly of filament 352 becomes externally rough due to the exited super absorbent polymer particles. This roughness brings discomfort to each consumer, when he or she touches the article in use. This is the reason why the holding sheet 380, which is made of e.g., a non-woven fabric and so on, is disposed between the absorbent member 53B and the covering sheet 358. Precisely, the toughness supplied only by the covering sheet 358, which is made of tissue paper (crepe paper) and the like, is not enough to retain the super absorbent polymer particles, hence the holding sheet 380 reinforces the toughness. As a result, the discomfort caused by this roughness when the consumer touches the diaper in use, can be reduced or eliminated by the holding sheet 380.

Figure 70:
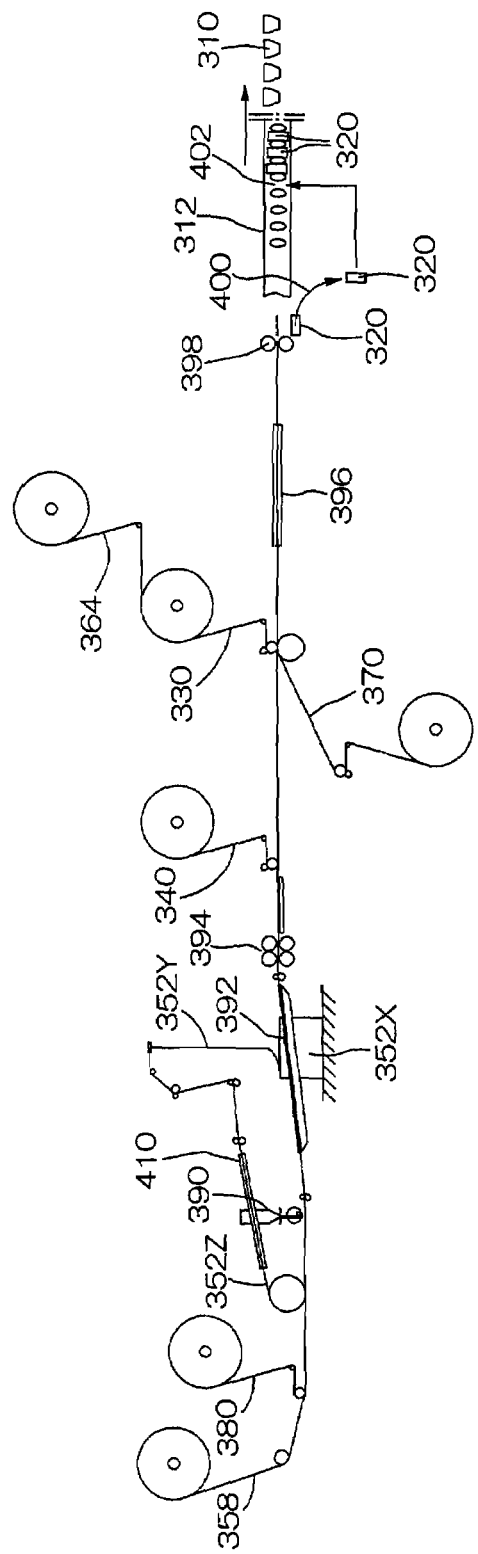
FIG. 70 is a schematic illustration showing a producing method for the pants-type disposable diaper.

Further, the existed absorbent polymer particles 354 are remained by the holding sheet 380 so that the particles do not move on the covering sheet 358. Accordingly, there is no fear to generate unevenly distribution of absorption capability. Particularly, in order to prevent the super absorbent polymer particles 354 from moving on the holding sheet 380, for example, hot melt adhesive having the adhesion can be previously coated on the holding sheet 380. FIG. 70 shows the applicator 404 for coating the adhesive. Alternatively, the upper surface (the wearer-side surface) of the holding sheet 380 may be processed into a rough face to prevent the super absorbent polymer particles 354 from moving on the holding sheet 380. As means for making surface rough or for carding for this purpose, there can be listed the use of non-et face which is a reverse face touching a net in production of non-woven fabric, a marble treatment, processing by needle punch and brushing treatment and the like.

Figure 68:
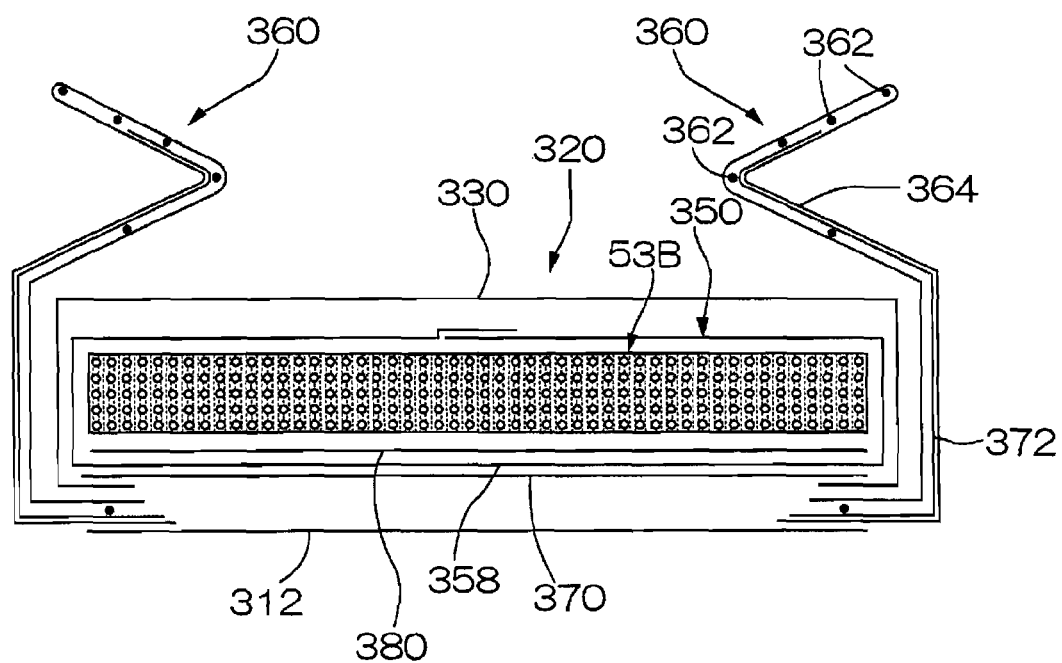
FIG. 68 is a cross section taken on line 303-303 of another embodiment.

In FIG. 68, the holding sheet 380 is disposed only below the absorbent member 53B. However, the holding sheet 380 can be extended to pass along the side faces of the absorbent member 53B and continuously along the upper surface of the absorbent member 53B. Further, plural holding sheets 380 can be used while they are piled.

In each of the above embodiments, the holding sheet 380 is interposed between the absorbent member 53B and the wearer-side of the covering sheet 358. However, the holding sheet 380 can be disposed at the under surface-side with respect to the covering sheet 358 (not shown). What is necessary is only that the holding sheet 380 is disposed at the under surface-side of the absorbent member 53B. Such configuration decreases or eliminates the discomfort feeling of the consumer when he or she touches the undersurface of the article.

If the body fluid impermeable sheet 370 is extended so as to wrap around the side surfaces to reach the upper surface in the wearer-side (not shown), the side leakage of the body fluid can be prevented. However, in this embodiment, for protecting against the side leakage, the second body fluid impermeable sheet 372 is interposed between the sheets of the double barrier sheet 364 forming each barrier cuff 360. Further, according to this embodiment, the second body fluid impermeable sheets 372 are extended so as to reach the standing portions of the barrier cuffs 360. Thus, there is supplied another advantage of the protection against the side leakage of the body fluid, which has diffused laterally on the face sheet 330, and the side leakage of the soft feces located between the barrier cuffs 360, 360.

Figure 67:
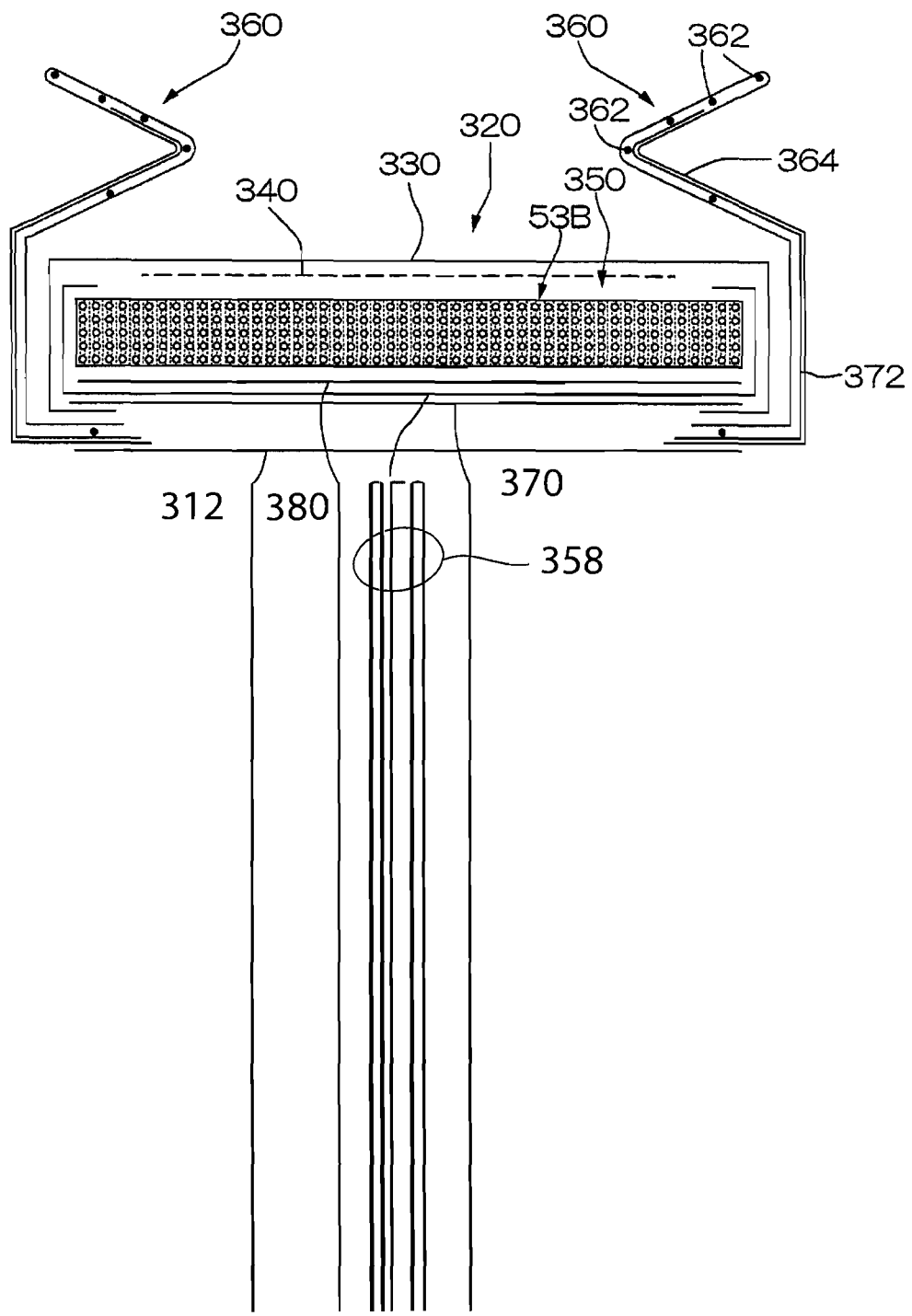
FIG. 67 is a cross section taken on line 303-303 of another embodiment.

The interposed sheet (second sheet) 340 is interposed between the top sheet 330 and the covering sheet 358. However, as shown in FIG. 67, it is possible not to provide the interposed sheet (second sheet) 340.

The body fluid is passed through the face sheet 330 and moved to the absorbent member 53B. Then, the interposed sheet (second sheet) 340 is adapted to speed up this movement. Precisely, the body fluid is passed through the interposed sheet 340 with higher speed than the speed with which the body fluid is passed through the face sheet 330. Then, the interposed sheet 340 is usually called as the second sheet. The interposed sheet 340 accelerates the moving of the body fluid to the absorbent member 53B so that the body fluid is absorbed into the absorbent member 53B with the high ability of absorption. Additionally, after the body fluid is absorbed into the absorbent member 53B, the interposed sheet 340 prevents the "reversing" of the body fluid, thus the top sheet can be externally kept dry.

The interposed sheet 340 in the drawing is disposed on the middle portion with the smaller distance than the width of the absorbent member 53B. However, the interposed sheet 340 may be disposed with the full distance in the width direction of the absorbent member 53B. Then, the interposed sheet 340 may be disposed with the same length in the longitudinal direction as that of the absorbent member. Alternatively, it may extend up and down in the longitudinal direction, from the zone for receiving the body fluid as the center, with the length being shorter than that of the absorbent member. The representative material of the interposed sheet 340 is a body fluid permeable non-woven fabric. Further, as stated above, it is possible not to provide the interposed sheet, and in this case, it is preferable that the absorbent member 52 includes the assembly of fibers in tows so that the body fluid can permeate the absorbent member.

Figure 66:
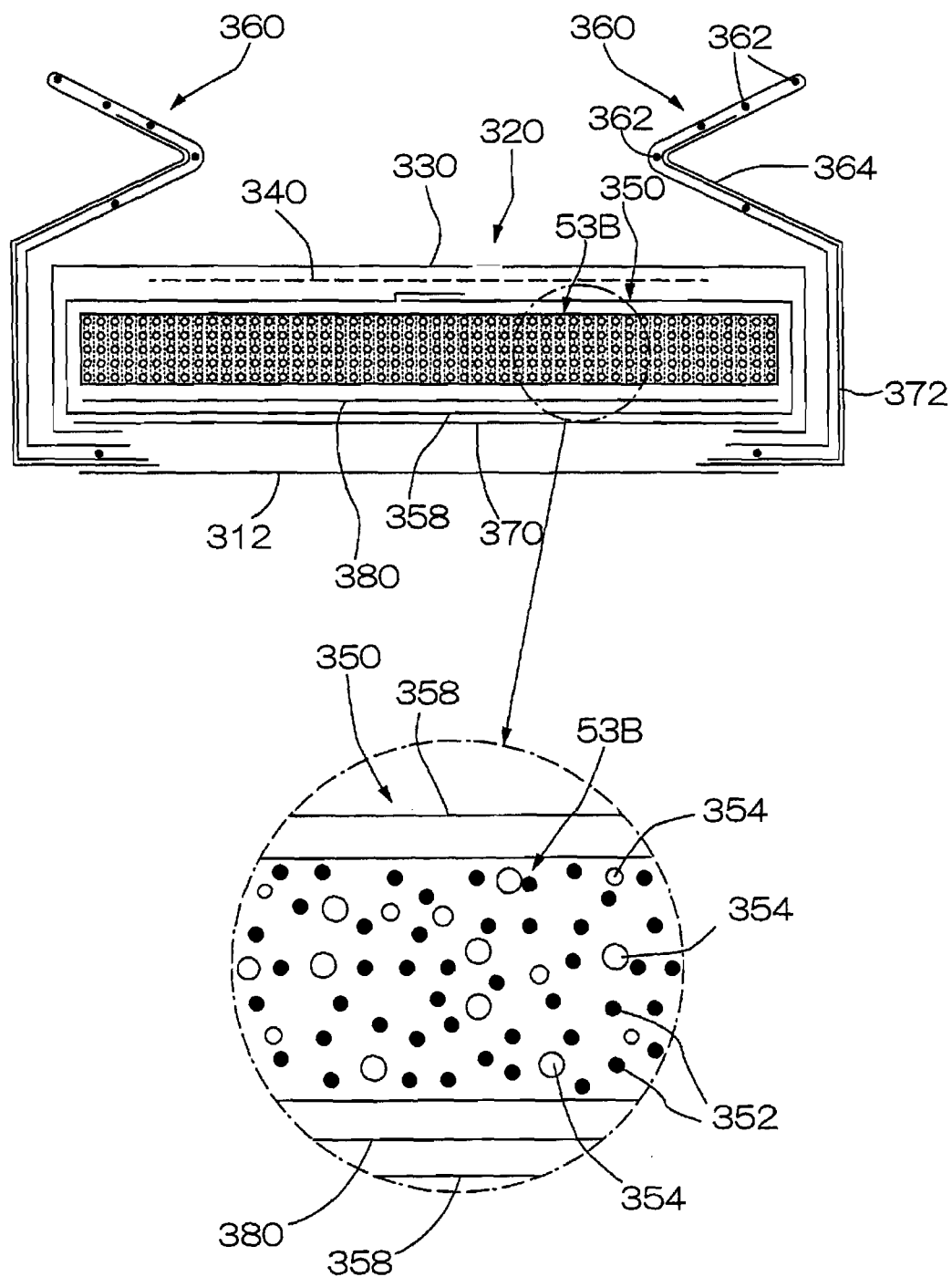
FIG. 66 is a cross section taken on line 303-303 of FIG. 64.

As the covering sheet 358, tissue paper, a non-woven fabric and the like can be used. As shown in FIG. 65, the covering sheet 358 may cover the whole of the layer including the assembly of filaments 352, 352 . . . and the super absorbent polymer particles 354, 354 . . . . Alternatively, for example, as shown in FIG. 66, the covering sheet 358 can cover only the under surface and the side faces of the layer. Further, if desired, it is possible that the covering sheet 358 is defined by an upper sheet and a lower sheet, between which a layer is interposed and it is also possible that the covering sheet 358 is disposed only at the under surface-side of the layer. However, these embodiments are not so preferable, because it is difficult to prevent the movement of the super absorbent polymer particles 354, 354 . . . .

Further, as another covering sheet 358, it may be possible that the absorbent member 53B is covered only at its top face and its side faces with crepe paper or a non-woven fabric and at its bottom face with a body fluid impermeable sheet such as a polyethylene sheet or the like. As still another covering sheet 358, it may be possible that the absorbent member 53B is covered at its top face with crepe paper or a non-woven fabric and at its side faces and its under surface with a body fluid impermeable sheet such as a polyethylene sheet or the like. (The covering sheet comprises these materials as the constituent elements.)

The holding sheet 380 is, as shown in FIG. 68, may be extended so as to wrap around the side faces of the absorbent member 53B. The conceptual drawing of FIG. 68 shows a case that the super absorbent polymer particles 354, 354 . . . are provided under the absorbent member 53B, otherwise another case that the super absorbent polymer particles 354, 354 . . . , which were originally included in the absorbent member 53B, are passed through so as to come out from the assembly of filaments 352, 352 . . . and moved to the holding sheet 380.

The barrier cuffs 360, 360 are provided for preventing the urine and soft feces from flowing laterally on the face sheet 330 and for protecting against the side leakage. However, they are additional components in the present invention.

Each barrier cuff 360, which is shown in the drawing, is made double with the water repellent non-woven sheet 364. Then, this barrier cuff 360 is extended from the under surface-side of the absorbent member 53B so as to cover the folded downwardly portion of the face sheet 330 and continuously project to the wearer-side. Particularly, in order to prevent the urine from flowing laterally on the face sheet 330, one side portion of body fluid impermeable sheet 370 is inserted between the sheets of the double non-woven sheet 364 so as to extend halfway in the barrier cuff 360.

The configuration of barrier cuff 360 can be designed desirably. For example, in the drawings, the elastically expansible members, e.g., rubber strands 362, 362 . . . are fixed in their elongated state in the barrier cuff 360 at the distal end and intermediate portion in the projecting part of the barrier cuff 360. Then, in use, the barrier cuff 360 is able to stand through the means of the application of the contracting force by the members 362, 362 . . . . In fixing the barrier cuff 360 to the front end portion and the back end portion of the face sheet 330, the rubber strands 362, 362 . . . in the intermediate portion of the cuff 360 are fixed inboard with respect to the rubber strands 362, 362 . . . in the distal end portion of the cuff 360. Due to this configuration, as shown in FIG. 65, the base portion of the cuff 360 stands at an angle inwardly, while the rest side portion of the cuff 360 stands at an angle outwardly.

Additionally, not shown in a figure, constitutional members of the absorbent body 320 are fixed each other by blanket, bead or spiral application of hot melt adhesive. This is to be repeated in the embodiments shown in FIG. 66 to 68.

In each embodiment, the absorbent element 350 includes the absorbent member 53B. This absorbent member 53B includes the assembly of filaments 352, 352 . . . in opened tows and the super absorbent polymer particles 354, 354 . . . . Then, in the absorbent member 53B, at least in the zone for receiving the body fluid, the super absorbent polymer particles (SAP particles) 354, 354 . . . are dispersed in the substantially full length of the thickness direction. This dispersion situation in the substantially full length of the thickness direction is shown conceptually in the enlarged fragmentary view in FIG. 65.

If there is little or no SAP particles 354, 354 . . . in the upper portion, lower portion and middle portion of the absorbent member 53B, such situation cannot be expressed as "dispersion situation in the substantially full length of the thickness direction". Then, as the "dispersion situation in the substantially full length of the thickness direction", the following cases can be included. First, in the assembly of filaments 352, 352 . . . , the SAP particles 354, 354 . . . are dispersed "evenly" in the full length of the thickness direction. Another included case is that although the SAP particles 354, 354 . . . are "unevenly distributed" in the upper portion, lower portion and/or middle portion, it is sure that some particles are still dispersed in the upper portion, lower portion and middle portion. Further, there are other cases not to be excluded from this dispersion situation. The one case is that some SAP particles 354, 354 . . . are not included in the assembly of filaments 352, 352 but remained on its surface. The other case is that some SAP particles 354, 354 . . . are passed through so as to come out from the assembly of filaments 352, 352 . . . and moved to the covering sheet 358. When the gel blocking is not concerned, the particles can be unevenly distributed only at the upper portion or only at the middle portion. Additionally, when the reversing is not concerned, the particles can be unevenly distributed only at the middle portion or only at the lower portion.

As for the size of absorbent member 53B, it has preferably the planar projection area of 400 cm² or more and the thickness of 1 to 10 mm, more preferably 1 to 5 mm. The absorbent member 53B having the size in this range gives the remarkable advantage in that the resilience can be improved without increase of weight, thickness and cost. Further, the absorbent member 53B is preferably configured to have the mass of 25 g or less, more preferably 10 to 20 g. The absorbent member 53B having the mass in this range gives the remarkable advantage in that there is no need of any other member for exclusive use.

It is preferable than the absorbent member 53B has the compressive resilience RC of 40 to 60%, more preferably 50 to 60%. In this way, sufficient resiliency can be obtained by the absorbent member 53B solely.

Further, it is preferable that the absorbent member 53B has the work of compression WC of 4.0 to 10.0 gf·cm/cm$^2$. In packing the article for the market, such absorbent member 53B may be compressed to be compact to the same degree or higher degree, comparing with the conventional absorbent members.

The compressive property can be adjusted by controlling the fiber density of the assembly of filaments 352 through the tow opening and the like; by selecting the type of fiber material, the type of binder e.g., plasticizer or the process level in the binder treatment, and the combination thereof.

The definition of the work of compression (WC) is the energy consumption caused by pressing the center of a specimen (the absorbent member 53B) of 200 mm long by 50 mm wide to 50 g.

This work of compression can be measured with Handy-Type Compression Tester (KES-G5 manufactured by KATO TECH CO., LTD.). The conditions in using this tester are: SENS: 2, Type of Force Sensor: 1 kg, SPEED RANGE: STD, DEF Sensitivity: 20, Pressurization Area: 2 cm$^2$, Sampling Rate: 0.1 (Standard), STROKE SET: 5.0, Maximum Weighting: 50 gf/cm$^2$.

On the other hand, the compressive resilience (RC) is a parameter regard to the resiliency of a compressed fiber. Accordingly, the higher the resiliency is, the larger the compressive resilience is. This compressive resilience can be measured with Handy-Type Compression Tester (KES-G5: KATO TECH CO., LTD.). The measuring conditions are the same as those in the above work of compression.

The basis weight of the super absorbent polymer particles can be desirably determined according to the absorption required for the application of the absorbent member. Therefore, although it cannot be assumed sweepingly, it can be 50 to 350 g/m$^2$. In the absorbent member, one effect caused by the using of the assembly of filament in tows is the lightweight effect. However, if heavy polymer is used in the absorbent member, such effect cannot be fulfilled sufficiently. Thus, the basis weight of the super absorbent polymer particles may be preferably 50 g/m$^2$ or less. More than 350 g/m$^2$ of basis weight of the super absorbent polymer particles not only brings the lightweight effect to be cancelled but also gives the above discomfort feeling due to the surplus absorbent polymer particles.

If desired, the dispersion density or dispersed amount of the super absorbent polymer particles on the plane direction of the absorbent member 53B can be adjusted. For example, the dispersed amount of the super absorbent polymer particles in the zone, into which the discharged body fluid is absorbed, can be adjusted so as to be larger than that in the rest of the upper surface of the absorbent member 53B. Further, in considering the difference between a man and a woman, for men, the dispersion density (dispersed amount) is increased at the front portion of the absorbent member 53B, while for women, the dispersion density (dispersed amount) is increased at its intermediate portion.

If desired, plural kinds of super absorbent polymer particles having different particle-size may be prepared so that they can be dispersed and projected by turn in the direction of thickness of the article. For example, plural super absorbent polymer particle dispersing means 390, which will be explained after, are placed along the line so as to be spaced one another. Then, the groups of super absorbent polymer particles having some kinds of particle sizes are fed into the plural dispersing means so that these means are arranged in the order of increasing particle size. In this way, the groups of super polymer particles can be dispersed and projected in the order of increasing particle size. Thus, in the absorbent member 53B, the smaller size particles are supplied in the lower portion while the larger size particles are supplied in the upper portion. This embodiment enables pushing more deeply the smaller size particles all the way into the assembly of filaments 352, 352 . . . .

The absorptive property depends on the proportion of the super absorbent polymer particles 354, 354 . . . with the assembly of filaments 352, 352 . . . . In the absorbent member 53B, in the plane area of 5 cm×5 cm in the zone, into which the body fluid is directly discharged, the super absorbent polymer particle mass/filament mass is preferably 1 to 14, more preferably 3 to 9.

Figure 75:
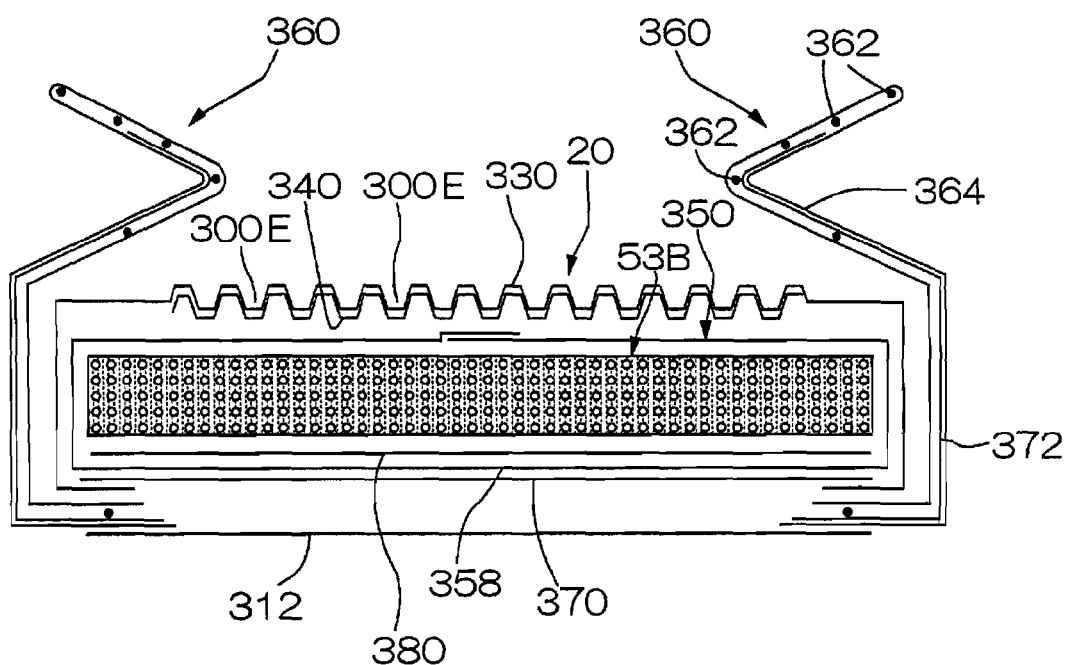
FIG. 75 is a cross section taken on line 303-303 of another embodiment.

As shown in FIG. 75, the concave grooves 300E can be formed with embossing on the wearer-side surface of the top sheet 330 so as to sink in the direction of the thickness. In forming the concave grooves 300E, there are several examples as stated below. First, the concave grooves 300E can be formed with embossing only on the top sheet 330. Second, as shown in FIG. 75, the concave grooves 300E can be formed with embossing on the top sheet 330 as well as on the interposed sheet 340. Further, the concave grooves 300E can be formed with embossing on the interposed sheet 340, or on the absorbent element 350. Then, the concave grooves 300E give the following effect. Precisely, along their extending direction, the body fluid can be introduced and diffused. The extending direction of the concave grooves 300E is preferably the longitudinal direction of the article. However, the concave grooves 300E may be extended in the width direction, or in the combination of the longitudinal direction and the width direction, i.e., in the reticular pattern.

Thus, the body fluid is diffused along the concave grooves 300E before reaching the absorbent member 53B. In this case, the larger area of the absorbent member 53B can be used for absorbing, which means that the absorbing capacity of the article is totally increased, and thereby the resultant absorbent article offers the protection against the side leakage and reversing, which would have been caused by the shortage of absorbing capacity.

When the interposed sheet 340 is provided, the concave grooves 300E may be formed with embossing on the intermediate sheet 340. The concave grooves 300E may be formed with embossing only on the interposed sheet 340 with no concave groove on the top sheet 330.

In order to form the concave grooves 300E with embossing on the both of the top sheet 330 and the interposed sheet 340, it is preferable that the interposed sheet 340 has the basis weight of 8 to 40 g/m$^2$ and the thickness of 0.2 to 1.5 mm and the top sheet has the basis weight of 15 to 80 g/m$^2$ and the thickness of 0.2 to 3.5 mm. Under such conditions, the embossing can be carried out sufficiently, without inhibiting the permeability.

Figure 69:
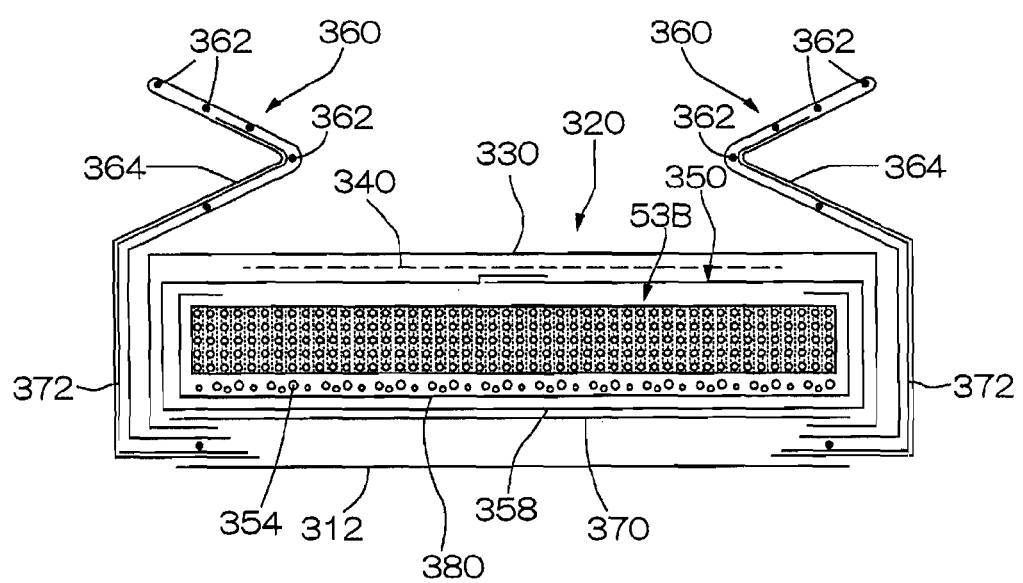
FIG. 69 is a cross section taken on line 303-303 of another embodiment.

Now, in order to clear the configuration of each absorbent article closely, the example of producing method of a disposable diaper will be explained. FIGS. 69 and 70 show the example of methods for producing the pants-type disposable diaper illustrated in FIGS. 63, 64 and 68.

The covering sheet 358 and the holding sheet 380 are fed down to the line, respectively. Next, the assembly 352Z of filaments 352, which is prepared by opening tows in a process stated closely after, is fed down. Then, with the super absorbent polymer particle dispersing means 390, the particles are dispersed on the assembly 352Z of filaments 352 so that the super absorbent polymer particles 354 can be dispersed substantially in the full length in the direction of thickness. After that, the resultant assembly 352Z is, through the folding member 392, wrapped with the covering sheet 358 to be the absorbent element 350. Then, this absorbent element 350 is divided in the direction of the line through the cutter 394 to be the individual absorbent elements 350.

Further, in this embodiment, the interposed sheet (second sheet) 340 is fed down intermittently, because the second sheet 340 is shorter, comparing with the full length of absorbent element 350.

Then, the component of the barrier cuff 360 and the top sheet 330 are fed down and the body fluid impermeable sheet 370 is fed up to the individual absorbent element 350. To the line for feeding the barrier sheet 364 as the component of the barrier cuff 360, previously, through a unit not shown, the rubber strands 362 are fixed in their elongated state between the two non-woven sheets, while the second body fluid impermeable sheet 372 is fixed also between the two non-woven sheets, thus, all of these sheets together with the top sheet 330 are supplied to the main line. The components of the barrier cuff 360, the top sheet 330 and body fluid impermeable sheet 370 are folded, through the folding member 396, as illustrated in FIG. 68.

Finally, after being cut with the cutter 398, each absorbent body 320, which has the shape of a rectangle and longitudinal direction along the main line, can be obtained at the end of the main line.

Thus obtained absorbent body 320 is rotated 90 degrees around to have longitudinal direction vertical to the main line, through the rotator 400.

On the other hand, in the line for the outer sheet 312, the rubber strands 312C are previously interposed between the two non-woven sheets (not shown in FIG. 69), which are passed as the outer sheet 312 and cut out with a cutter (not shown) to have ellipse shaped hollows into each of which the wearer's leg is inserted. Then, when the outer sheet 312 reaches the combining station 402, the above rotated absorbent body 320 is placed between each pair of adjacent two hollows on the combining station 402 so as to fix there with hot melt adhesive and the like. The absorbent body 321 is thus jointed with the outer sheet 312. After that, this is folded in its longitudinal direction with respect to the horizontal line of FIG. 69. Then, the both side edges of the front body 312F and back body 312B are jointed at their jointing zones 312A with heat seal. Finally, the folded and jointed absorbent body is divided in the direction of line so as to be individual articles 310, 310 . . . (dividing means is not shown).

The tow removed from the bale 352X is opened as illustrated in FIG. 70. The tow 352Y out from the bale 352X, is passed through the guide 420 and turned some degrees with the turning means 422. Then, this is passed through the nip of the pretension roll 424, further through the first nip 426A, the second nip 426B and the third nip 426C, by each of which each guide 420 is followed, and introduced into the second opening apparatus 410, where the last opening is performed. Thus obtained assembly 352Z of the filaments 352 is sent to the folding member 392. On the peripheral surface of the one roller of the second nip 426B, many grooves are formed so as to be continuous in the peripheral direction and spaced each other with short distance in the longitudinal direction of the roller. These grooves fulfill the effect of promoting the opening due to the many filaments buried in the grooves.

The rotation speed of each nip roll is adjusted so that the tow 352Y is tensed between the first nip 426A and the second nip 426B, while, the tow 352Y is loosen between the second nip 426B and the third nip 426C. Further, in order to introduce smoothly the tow 352Y to the first nip 426A, the pretension roll 424 is adapted to control the tension applied to the tow 352Y removed from the bale 352X.

In the first opening apparatus configured above, due to the tension applied to the tow 352Y, crimp is removed to some degree so that the separation of the filaments 352 is promoted. After that, the tow 352Y is loosened with the second nip 426B and the third nip 426C. Thus, the tow 352Y can be separated mainly in the width direction.

Figure 71:
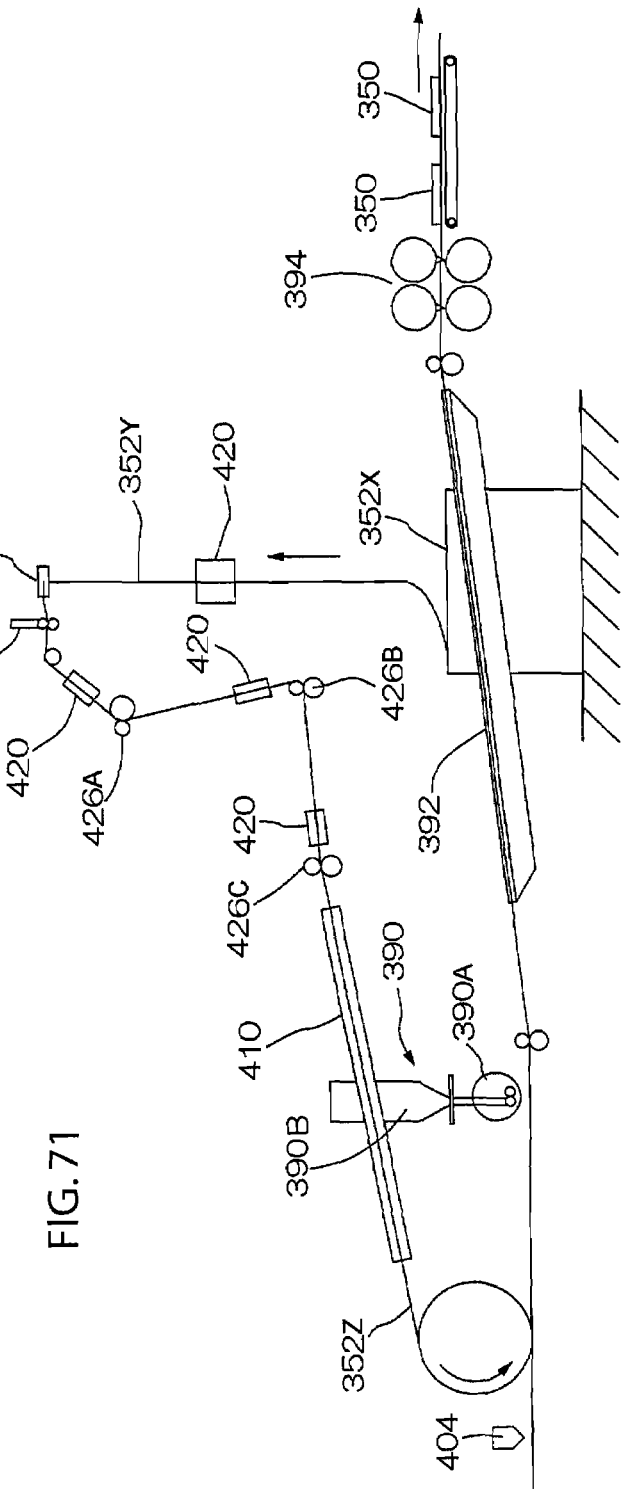
FIG. 71 is a schematic illustration showing a relevant part of FIG. 69.

Subsequently, the tow 352Y is introduced to the second opening apparatus 410, which is constructed in the same manner as disclosed in, for example, Japanese Unexamined Patent Application Publication No. 1984-500422 (WO 83/03267). As shown in FIG. 71 schematically illustrating, in the second opening apparatus 410, the venturi chamber 410*b* is formed between the inlet 410A and the outlet 410B, the air jet 410*a* for compressed air is disposed in the inlet-side and the exhaust hole 410*c* is provided in the venturi chamber 410*b*. This apparatus has the shape of a substantially rectangle in its plan view and a flat shape in the direction passing through this drawing.

When the compressed air is blown through the air jet 410*a*, the air is introduced from the inlet 410A due to the ejector effect. Thus, the tow 352Y is drawn into and advanced through the apparatus. When the tow 352Y reaches the venturi chamber 410*b*, the air is exhausted from the air exhaust holes 410*c* while the space in the venturi chamber 410*b* is increased. This causes the tow 352Y to be opened mainly in the direction of thickness. At the same time, as shown in the lower drawing of FIG. 72, the tow 352Y is separated in the direction of width.

The present inventors found that since the opening is not sufficient only by the second opening apparatus 410, it is preferable that the tow 352Y is previously opened with the first opening apparatus, which tensing and loosing the tow 352Y. Therefore, it is desirable to combine the above two kinds of opening for the performance in the process.

Figure 72:
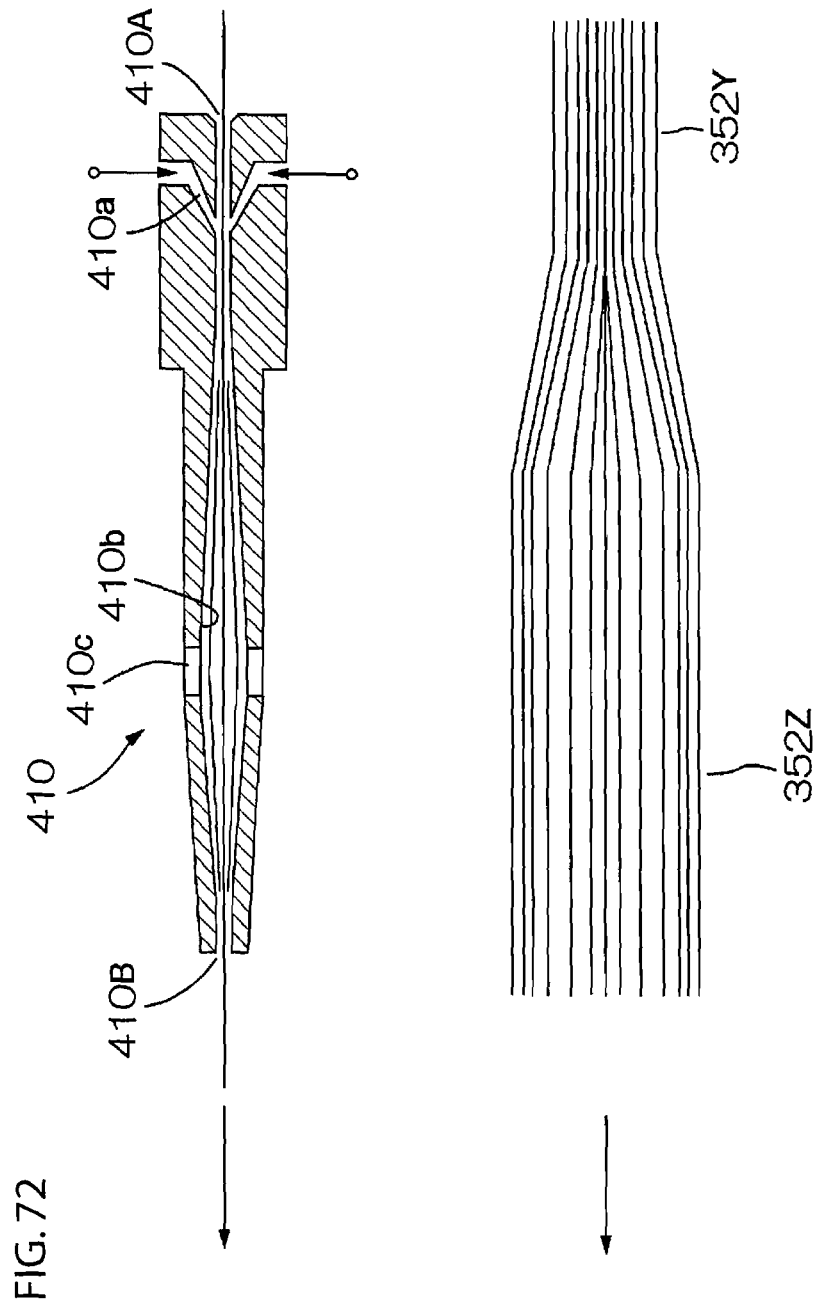
FIG. 72 is a schematic illustration showing an opening apparatus.

In the present invention, the super absorbent polymer particle dispersing means 90 disperses these particles 354 to the assembly 352Z of filaments 352 in the substantially full length of its thickness. Then, the dispersing means 90 is desirably adapted to give not only the falling power caused from the weight of each super absorbent polymer particle 354 but also the accelerating force. FIG. 72 shows one example of this means.

Precisely, the super absorbent polymer particle dispersing means 390 comprises the casing 390*a*, which is provided with the aperture at its bottom, the rotating drum 390*b*, which has projecting holes 390*d* and which is configured to rotate on the moving direction of the web (anticlockwise direction in FIG. 72), and the shutter drum 390*c*, which is put inside of the rotating drum 390*b*. The shooting unit 390A configured with these elements is connected to the hopper 390B (See FIG. 70) so as to construct the super absorbent polymer particle dispersing means 390.

The super absorbent polymer particles 354 discharged from the hopper 390B are adapted to be supplied into the rotating drum 390*b*. Previously, is performed the positioning of the aperture of the shutter drum 390c with respect to the aperture of the casing 390a. In FIG. 72, these apertures are completely superimposed, indicating the full open of the dispersing means 390. The projecting holes 390d are provided on the peripheral surface of the rotating drum 390b so as to form several groups, in this drawing, the four groups. That is to say, in the embodiment of this drawing, during one rotation of rotating drum 390b, the super absorbent polymer particles 354 are dispersed and projected on the four disposable diapers one by one.

The positioning of the shutter drum 390c is performed, after that, while the casing 390a and the shutter drum 390c are not rotated but in stationary state, the rotating drum 390b is rotated. In this situation, the super absorbent polymer particles 354 are fallen through the projecting holes 390d, at the same time, due to the rotation of rotating drum 390b, component of centrifugal force is applied to the super absorbent polymer particles 354 in radius direction. Accordingly, to the super absorbent polymer particles 354, the accelerating force beyond the free fall is applied so that the super absorbent polymer particles 354 are dispersed and projected at the high speed on the assembly 352Z of filaments 352. As a result, the super absorbent polymer particles 354 can be pushed all the way into the spaces between filament-filament 352. In dispersing and projecting the super absorbent polymer particles 354, if their free falling is used solely, the super absorbent polymer particles 354 are distributed limitedly, in mainly upper portion of the assembly 352Z of filaments 352, that is, it would be difficult for the super absorbent polymer particles 354 to disperse evenly into the assembly 352Z in the direction of its thickness.

The super absorbent polymer particles 354 may be continuously dispersed and projected on the assembly 352Z of filaments 352. However, such continuous operation has the following problem. Precisely, as shown in FIG. 69, when the absorbent element 350 is divided in the direction of the line through the cutter 394 to be the individual absorbent elements 350, due to the super absorbent polymer particles in the assembly, the blade of the cutter 394 will be worn in a short period. Therefore, the super absorbent polymer particles 354 should not be continuously dispersed and shot. It is preferable that the particles 354 are dispersed and shot intermittently only to the zones 300Z as seen from FIG. 72.

In order to attain this, as stated before, the projecting holes 390d provided on the peripheral surface of the rotating drum 390b form several groups, in this drawing, the four groups on the peripheral direction. Thus, the super absorbent polymer particles 354 are intermittently dispersed and projected on only the four zones 300Z one by one. In this way, since the assembly may be cut at each position between the zone 300Z and the next zone 300Z with the cutter 394, the blade of the cutter 394 is inhibited from wearing.

The dispersed amount of the super absorbent polymer particles 354 can be adjusted mainly by adjusting the size of projecting hole 390d and by positioning of the aperture of the shutter drum 390c with respect to the aperture of the casing 390a, and the position of the above each aperture may be adjusted so as to correspond to the process line speed. Further, the dispersed pattern of the super absorbent particles 354 can be adjusted by arranging the groups of the shooting holes 390d.

Alternatively, the super absorbent polymer particles 354 may be, as desired, together with compressive air, dispersed and projected on the assembly 352Z of the filaments 352 so that the polymer particles 354 can be dispersed totally in the direction of the thickness of the assembly 352Z of the filaments 352. However, according to this operation, the super absorbent polymer particles 354, which are already dispersed and projected on the assembly 352Z of the filaments 352, will be scattered by the compressive air, resulting in the fear of dispersion in the undesirable zones. Accordingly, such operation cannot be recommended.

Further, together with or instead of the operation by the super absorbent polymer particle dispersing means 390, the super absorbent polymer particles 354 dispersed on the assembly 352Z of the filaments 352 may be drown from the lower side thereof.

Figure 76:
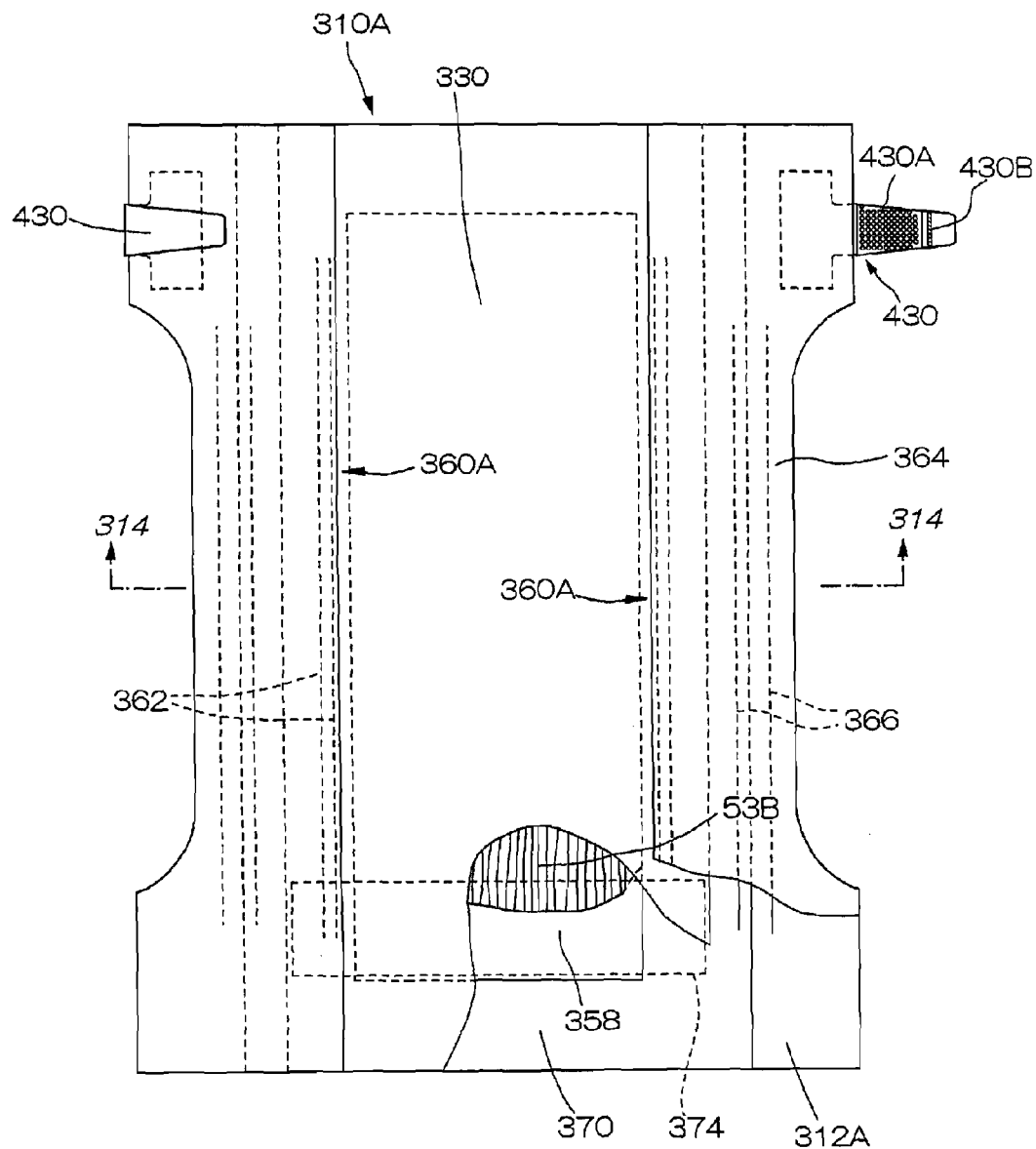
FIG. 76 is a plan view of a developed tape-type disposable diaper.

Now, the embodiment focusing the viewpoint of dispersion of super absorbent polymer particles to assembly of fibers in tows will be explained by way of another embodiment (tape-type disposable diaper), with reference to FIGS. 75 and 76. FIG. 76 is the cross section taken on line 314-314 in FIG. 75, but the absorbent body 320 is illustrated with a little bit exaggeration.

The tape-type disposable diaper 310A includes the tape fasteners 430 secured to the both side edges in the back portion of the diaper and the hook elements 430A on the securing portions of the tape fasteners 430. Then, the back sheet 312A serving as the under surface of the diaper 310A is formed with laminating non-woven fabrics. For wearing this diaper, the hook element 430A is adapted to engage to a given portion on the external surface of the back sheet 312A.

Concretely, in this diaper, the absorbent member 53B is interposed between the top sheet 330 and the impermeable sheet 370 made of e.g., polyethylene. Then, the fluid is substantially impermeable through this sheet 370. The absorbent member 53B is totally wrapped with the covering sheet 358 made of tissue paper and has the shape of a rectangle in the plan view. The holding sheet 380 is interposed between the absorbent member 53B and the covering sheet 358.

Additionally, the interposed sheet 340 is interposed between the top sheet 330 and the absorbent member 53B. The impermeable sheet 370 has the shape of a rectangle with larger width than that of the absorbent member 53B. Further, the hourglass shaped back sheet 312A made of non-woven fabric is provided externally with respect to the impermeable sheet 370.

The top sheet 330 has the shape of a rectangle with the larger width than that of the absorbent member 53B and extends outboard a little with respect to the side edge of the absorbent member 53B so as to be fixed to the impermeable sheet 370 with e.g., hot melt adhesive.

At the both side portions in the longitudinal direction of the diaper 310A, the barrier cuffs 360A are formed so as to project toward the wearer-side. The barrier cuff 360A comprises a barrier sheet 364, which is made of a non-woven fabric being substantially continuous in the width direction, and the elastically expansible member 362 such as a rubber strand member defined by one or plural elastically expansible rubber strand or strands for encircling the wearer's leg. The numeral reference 430 designates the planar fastener, tape fastener.

The inside face of the barrier sheet 364 has a fixation starting edge, from which this inside face starts to be fixed and which is spaced from the side edge of the top sheet 330. From the fixation starting edge, the inside face of the barrier sheet 364 is fixed, with e.g. hot melt adhesive, to the extended side portion of the impermeable sheet 370 outboard with respect to the fixation starting edge. Then, the under surface of the outside face of the barrier sheet 364 is fixed, with e.g. hot melt adhesive, to the back sheet 312A. Further, the elastically expansible members 366, for example, rubber strands are provided for the barrier cuffs.

The fixation starting edge of the inside face of the barrier sheet 364 defines also the standing base line of the barrier cuff 360A. The barrier cuff, inboard with respect to this standing base line, is not fixed to the article but free. This free portion can stand due to the contracting force of the rubber strands 362.

In this embodiment, since the planar fastener is used as the tape fastener 430, the fastener can be secured mechanically to the back sheet 312A. Accordingly, so-called target tape can be omitted, and at the same time, the securing position of the tape fastener 430 can be selected freely.

In the tape fastener 430, the fastening substrate, which is made of plastic, polyethylene laminate non-woven fabric, paper and the like, is jointed, at its base portion, to the back sheet 312A with e.g., adhesive. Further, the tape fastener 430 has the hook element 430A at its fore end-side. The hook element 430A is jointed to the fastening substrate with adhesive. Then, the hook element 430A has many engaging protrusions on its wearer-side surface. Additionally, the tape fastener 430 has the temporary adhesive joint 430B, which is adjacent outboard to the hook element 430A. In the last stage of assembling process of the article, the temporary adhesive joint 430B is jointed to the barrier sheet 364. Thus the fore end-side of the tape fastener 430 is prevented from tearing. In use, against such adhesion, the fore end-side portion of the tape fastener 430 is torn from the barrier sheet 364 and brought to the front body-side. In the tip end of the tape fastener 430, the portion outboard with respect to the temporary adhesive joint 430B is a pick tab, in which the fastening substrate is exposed.

In the front body, along the waist open, the target print sheet 374 is provided on the under surface of the back sheet 312A. On the target sheet 374, there is target print, which is designed so as to show a mark for the securing position of the hook elements 430A of each tape fastener 430. In this way, the target print can be seen through the back sheet 312A from the outside of the diaper.

During the diaper 310A is worn, the diaper 310A forms a boat shaped position against the body of the wearer and the contracting force is supplied by the rubber strand 362. Thus, the barrier cuff 360A stands around the wearer's leg due to such contracting force caused by the rubber strand 362.

The standing portions of the barrier cuffs form a pocket space, which encloses urine or soft feces. When the urine is discharged into the pocket space, the urine is passed through the top sheet 330 into the absorbent member 53B, where the urine is absorbed. On the other hand, the solid component of the soft feces is prevented from overflowing beyond the standing portion of the barrier cuffs 360A, which serves as a barrier. If the urine should overflow beyond the distal side edge of the standing portion, the surface contacting portion of the barrier cuff functions to stop such overflowing, thus side leakage can be protected.

In this example, the barrier sheet 364 forming each standing cuff is preferably not fluid permeable but substantially fluid impermeable (fluid semipermeable is possible). The face sheet (laminating non-woven fabrics) 330 may be treated with silicone so as to have water repellent property. In any way, a gas permeable sheet having the hydraulic pressure proof of 100 mm $H_2O$ or more is preferable for both of the barrier sheet 364 and the back sheet 312A. Under such condition, the article shows gas permeable at the both side portions in the width direction, which prevents the humid discomfort to the wearer.

It is needless to say that the configuration of the absorbent member 53B or that of the absorbent body 320 can be applied to a sanitary napkin, an incontinence pad, an absorbent pad cooperatively piled on disposable diaper and the like. In these applications, the configurations can be easily speculated by those skilled in the art, thus, their explanations will be omitted.

[Material and the Like of Each Part]
(Assembly of Fibers in Tows (Assembly of Filaments))

An assembly of fibers in tows (the assembly is produced from the tows as the raw material) means tows (fiber bundles), each fiber of which is treated as substantially continuous single fiber. As the constituent fiber of the tow, there are for example, polysaccharide or the derivatives thereof (cellulose, cellulose ester, chitin, chitosan or the like), synthetic polymer (polyethylene, polypropylene, polyamide, polyester, poly lactamide, polyvinyl acetate or the like), and the like can be used. Above all the cellulose ester and cellulose are preferable.

Further, as the cellulose, cellulose derived from plant such as cotton, linter, wood pulp or the like as well as bacterial cellulose may be used. Regenerated cellulose such as rayon may be also used, and closely as the regenerated cellulose, a spun regenerated cellulosic fiber may be used. The shape and size of the cellulose can be selected from the wide range, from substantially infinite length of the continuous single fiber to the length of about few millimeters to few centimeters (for example, 1 mm to 5 cm) in the major axis of fiber and to the particle size of about few micron (for example, 1 to 100 μm) of fine powder. The cellulose may be fibrillated such as beaten pulp or the like.

On the other hand, as the cellulose ester, there can be listed esters of organic acids such as cellulose acetate, cellulose butyrate, cellulose propionate or the like; esters of mix acids such as cellulose acetate propionate, cellulose acetate butyrate, cellulose acetate phthalate, cellulose acetate nitrate or the like; and the derivatives of the cellulose ester such as polycaprolactone grafted cellulose ester or the like. The cellulose esters can be used alone or in two or more kinds thereof. The viscosity average degree of polymerization of the cellulose ester is for example, about 50 to 900 and preferably about 200 to 800. Then the average degree of substitution of cellulose ester is for example, about 1.5 to 3.0 (for example, 2 to 3).

The average degree of polymerization of the cellulose esters may be for example, about 10 to 1000, preferably about 50 to 900 and more preferably about 200 to 800. Then, the average degree of substitution of cellulose ester may be for example, about 1 to 3, preferably about 1 to 2.15, more preferably about 1.1 to 2.0. The average degree of substitution of cellulose ester can be determined from the viewpoint of improving the biodegradability.

As the cellulose ester, esters of organic acids (for example, the ester with organic acid having the carbon number of about 2 to 4) are preferable and cellulose acetate is particularly preferable. This is because the cellulose acetate is specifically suitable for increasing the absorbed volume of body fluid due to its increased porosity. Concretely, in the case of body fluid permeable absorbent member 52, its porosity (the space volume/the absorbent member volume) can be preferably 60 to 85%, more preferably 75 to 85%.

The acetylation degree of the cellulose acetate is, in many cases, 43 to 62%. Particularly, it is more preferably 30 to 50%, because this range causes high biodegradability. It is specifically preferable that cellulose ester is cellulose diacetate.

To the fibers in tows, several kinds of addition agents may be added, such as heat stabilizer, colorant, oil solution, yield improving agent, whiteness improving agent or the like.

The fineness of each fiber may be for example, 1 to 16 denier, preferably 1 to 10 denier, more preferably 2 to 8 denier. The fiber may be uncrimped, but the fiber is preferably crimped. The degree of crimp of the crimped fiber may be for example, 5 to 75, preferably 10 to 50, more preferably 15 to 50 pieces of crimp per 1 inch (2.54 cm). In many cases, uniformly crimped fibers are used. By using the crimped fibers, bulky and lightweight absorbent member can be produced, as well as high integrity of the tows can be produced easily due to the tangle of the fibers. The cross sectional shape of the fiber is not specifically limited and may be selected from the group including circle, ellipse, irregular shape (e.g., Y-shaped, X-shaped, 1-shaped, R-shaped or the like) and the like, further, the hollow type fiber may be possible. The fibers can be used in the tows (fiber bundles), each of which is formed by bundling for example, about 3,000 to 1,000,000, preferably about 5,000 to 1,000,000, single fibers. It is preferable that about 3,000 to 1,000,000 continuous single fibers are gathered to the fiber bundle.

When the body fluid is repeatedly absorbed into the assembly of fibers in tows, since the tangle of the fibers is weak, the spaces between the fibers should be treated so as not to collapse (so as not to loose the stiffness). Therefore, the binder, which can adhere or fuse the fibers at their mutual contacting portions, can be used preferably. The binder is used in the same manner as stated above.

As the binder used here, there can be listed ester plasticizer such as triacetin, triethylene glycol diacetate, triethylene glycol dipropionate, dibutyl phthalate, dimethoxyethyl phthalate, triethyl ester citrate or the like as well as several kinds of resin adhesives, specifically thermoplastic resin.

When the thermoplastic resin is fused•solidified, the adhesiveness is appeared. This resin includes water-insoluble, water-hardly soluble resin and water-soluble resin. If desired, these resins can be jointly used.

As the water-insoluble or water-hardly soluble resin used here, there can be listed olefin monopolymer or olefin copolymer such as polyethylene, polypropylene, ethylene-propylene copolymer, ethylene-vinyl acetate copolymer or the like, acrylic resin such as polyvinyl acetate, polymethyl methacrylate, methyl methacrylate-acrylic ester copolymer, copolymer of (meta) acrylic monomer and styrene monomer or the like, styrene polymer such as polyvinyl chloride, vinyl acetate-vinyl chloride copolymer, polystyrene, copolymer of styrene monomer and (meta)acrylic monomer, modifiable polyester, polyamide such as, nylon 11, nylon 12, nylon 610, nylon 612 or the like, rosin derivatives (e.g., rosin ester or the like), hydrocarbon resin (e.g., terpene resin, dicyclopentadiene resin, petroleum resin or the like), hydrogenated hydrocarbon resin, and so on. These thermoplastic resins can be used alone or in two or more kinds thereof.

As the water-soluble resin used here, there can be listed various kinds of water-soluble polymer, for example, water-soluble vinyl resin such as polyvinyl alcohol, polyvinyl pyrrolidone, polyvinyl ether, copolymer of vinyl monomer and copolymerizable monomer having carboxyl group, sulfonic group or the salt thereof or the like, water-soluble acrylic resin, polyalkylene oxide, water-soluble polyester, water-soluble polyamide and the like. These water-soluble resins can be used alone or in two or more kinds thereof.

Several kinds of additives can be added to the thermoplastic resin. There are for example, stabilizing agent such as anti-oxidizing agent, ultraviolet absorber or the like, filler, plasticizer, antiseptic agent, mildewproofing agent and the like.

However, any binder, which blocks the penetration of super absorbent polymer particles into the assembly, should not be used as much as possible. It is best to avoid the use of binder, which prevents the super absorbent polymer particles from penetrating the assembly.

The assembly of fibers can be produced from the tows as the material according to the conventional processes. The bale of tows of cellulose diacetate, which can be used preferably in the present invention, is available in the market from Celanese Chemicals, Ltd., Daicel Chemical Industries Ltd., and the like. In the bale of tows of cellulose diacetate, the density is about 0.5 g/cm$^3$ and the total weight is 400 to 600 kg.

The tow removed from the bale can be opened so as to be belt-shaped with preferable size and bulk as desired. The width of opened tow can be determined arbitrarily, can be for example, about 100 to 2000 mm, preferably about 150 to 1500 mm. The opening of the tow is preferable, because opening treatment facilitates the easy movement of the absorbent polymer. Further, the opening degree of tow is adjusted so that the porosity and density of the tow can be preferably arranged.

Figure 10:
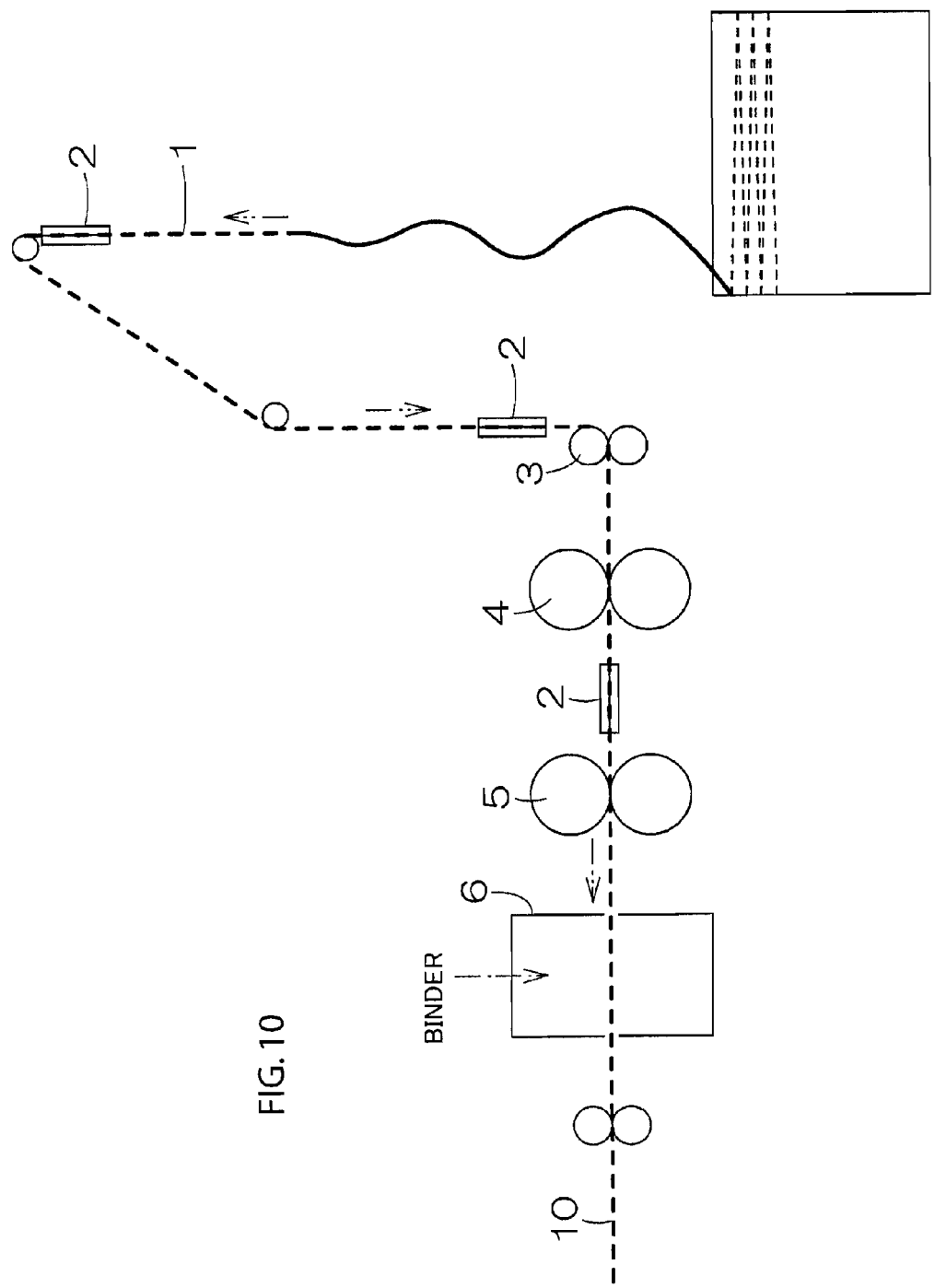
FIG. 10 is a schematic illustration showing a producing flow for an assembly of fibers.

As a method for opening the tow, there can be listed a method that a tow is applied to plural opening rolls, through which the tow is processed, and the tow is gradually widened; a method of opening tow by repeating the stretching (elongating) and relaxing (contracting) of tow; a method of widening•opening tow with compressed air and the like FIG. 10 is a schematic illustration for showing the producing flow for opening. The tow 1 as the material is taken out continuously and transported through an opening section where the widening means 2 using the compressed air is combined with the plural opening nip rolls 3, 4, and 5 each having the speed being increased as the line flows downstream. In this opening section, the tow 1 is widened and opened. After that, thus resultant tow is passed through the binder addition box 6 so that the binder is added to the tow (For attaining this, for example, the box 6 is previously filled with the mist of triacetin). Finally, the assembly 10 of fibers in tows having the preferable width and density can be formed.

For adding the binder to the tow, there can be listed some methods, for example, wick application system, brush application system and the like. In the wick application system, a piece of felt, into which triacetin is previously penetrated, is contacted with the surface of a roll so that the binder is transferred on the surface, and then, through which, the triacetin is added to the opened tow. On the other hand, in the brush application system, in a binder addition box provided with a slit, the binder exuded from the slit is sprayed in the form of mist to the opened tow by utilizing a rotating brush.

The absorbent member 53B shown in FIG. 33 can be obtained by adding uniformly the binder to the absorbent member 53B for the purpose of wide use. The absorbent member 53B shown in FIG. 34 can be obtained by adjusting the added amount of binder to the middle portion in the width direction of the absorbent member 53B so as to be larger than the added amount of binder to the both side portions in the width direction of the absorbent member 53B. The absorbent member 53B shown in FIG. 35 can be obtained by adjusting the added amount of binder to the both side portions so as to be larger than the added amount of binder to the middle portion. The absorbent member 53B shown in FIG. 36 can be obtained by leaving out the intermediate portion in the longitudinal direction of the absorbent member 53B in adding the binder to its surface. The absorbent members 53B shown in FIGS. 38, 39, 41 and 42 can be obtained by coating the binder with the brush application system and subsequently by coating the binder with the wick application system. Alternatively, the various absorbent members 53B shown in FIGS. 33 to 41 can be obtained by, in the binder addition box, in dispersing the binder on the surface of the absorbent member 53B, dispersing unevenly in its width direction, leaving out the intermediate portions, adjusting desirably the concentration of the binder to be coated and the like.

(Face (Top) Sheet 51 (330))

In this embodiment, the face sheet 51 has the character of allowing the body fluid to permeate. Accordingly, what is required for the material of the face sheet 51 is only the body fluid permeability. There can be listed as the example of the face sheet 51, a porous or non-porous non-woven fabric, a porous plastic sheet and the like. Fiber material of non-woven fabric is not particularly limited. For example, there can be exemplified synthetic fibers such as olefin like polyethylene and polypropylene, polyester and polyamide; regenerated fibers such as rayon and cupra; natural fibers such as cotton; and mixed fibers used in 2 or more kinds thereof. Additionally, the method for producing the non-woven fabric is not specifically limited. There can be exemplified conventional methods such as a spunlace method, a spunbond method, a thermalbond method, a meltblown method, a needlepunch method and the like. For example, the spunlace method is preferable for flexibility and drape characteristics, while the thermalbond method is preferable for bulky nature and softness.

The face sheet 51 may be formed with single sheet and also may be formed with laminated sheet consisting of piled plural sheets in the thickness direction. Similarly, the top sheet 51 may be, in the plane direction, formed with single sheet and also formed with plural sheets.

(Body Fluid Permeable Absorbent Member 52)

In this embodiment, the absorbent member 52 is to be, similarly to the face sheet 51, body fluid permeable. Additionally, the absorbent member 52 should include the assembly of fibers in tows, and preferably include only the assembly of fibers in tows, because such assembly is porous resulting in the high absorbing capacity for the body fluid. Then, if each fiber of the assembly has irregular cross sectional shape, the body fluid often collides with the fiber. Therefore, it is preferable that each fiber has the cross sectional shape of a circle or of an ellipse. Such cross sectional shape causes no collision between the body fluid and the fiber so that the body fluid can permeate at the higher speed.

In this embodiment, the construction of absorbent member 52 is not specifically limited. For example, the absorbent member 52 may be formed with a single sheet, may be formed with a sheet layer consisting of laminating two, three, four or more sheets and may be core like.

(Interposed (Second) Sheet 340)

As the interposed sheet 340, there can be exemplified, a similar material as that of the top sheet, a spunlace non-wood fabric, a pulp non-woven fabric, a mixed sheet of pulp and rayon, a pointbond fabric, and crepe paper. Particularly, an airthrough non-woven fabric and a spunbond non-woven fabric are preferable.

(Body Fluid Retainable Absorbent Member 53A, 53B)

In this embodiment, the characteristic for retaining the absorbed body fluid is common to the body fluid retainable absorbent member 53A and 53B. However, as for their material, the one member is not required to have the assembly of fibers in tows (the absorbent member 53A) and the other member is required to have the assembly of fibers in tows (the absorbent member 53B).

The material of the absorbent member 53A is not specifically limited. There can be listed from the conventional materials, for example, pulp as a simple substance such as flocculated pulp, synthetic pulp or the like, fluffing pulp absorbing absorbent polymer in the form of e.g., particles and so on. The material fiber of the pulp is not specifically limited. There can be exemplified cellulose fiber from wood such as mechanical pulp, chemical pulp, dissolving pulp, or the like, artificial cellulose fiber such as rayon, acetate or the like, and so on. As wood for the cellulose fiber, acicular tree is more preferable than broad leaf tree in function and cost, because the fiber length of the acicular tree is longer than that of the broad leaf tree.

On the other hand, the absorbent member 53B is formed with an absorbent member obtained by moving absorbent polymer into an assembly of fibers in tows. Now, this absorbent member will be explained closely.

Figure 11:
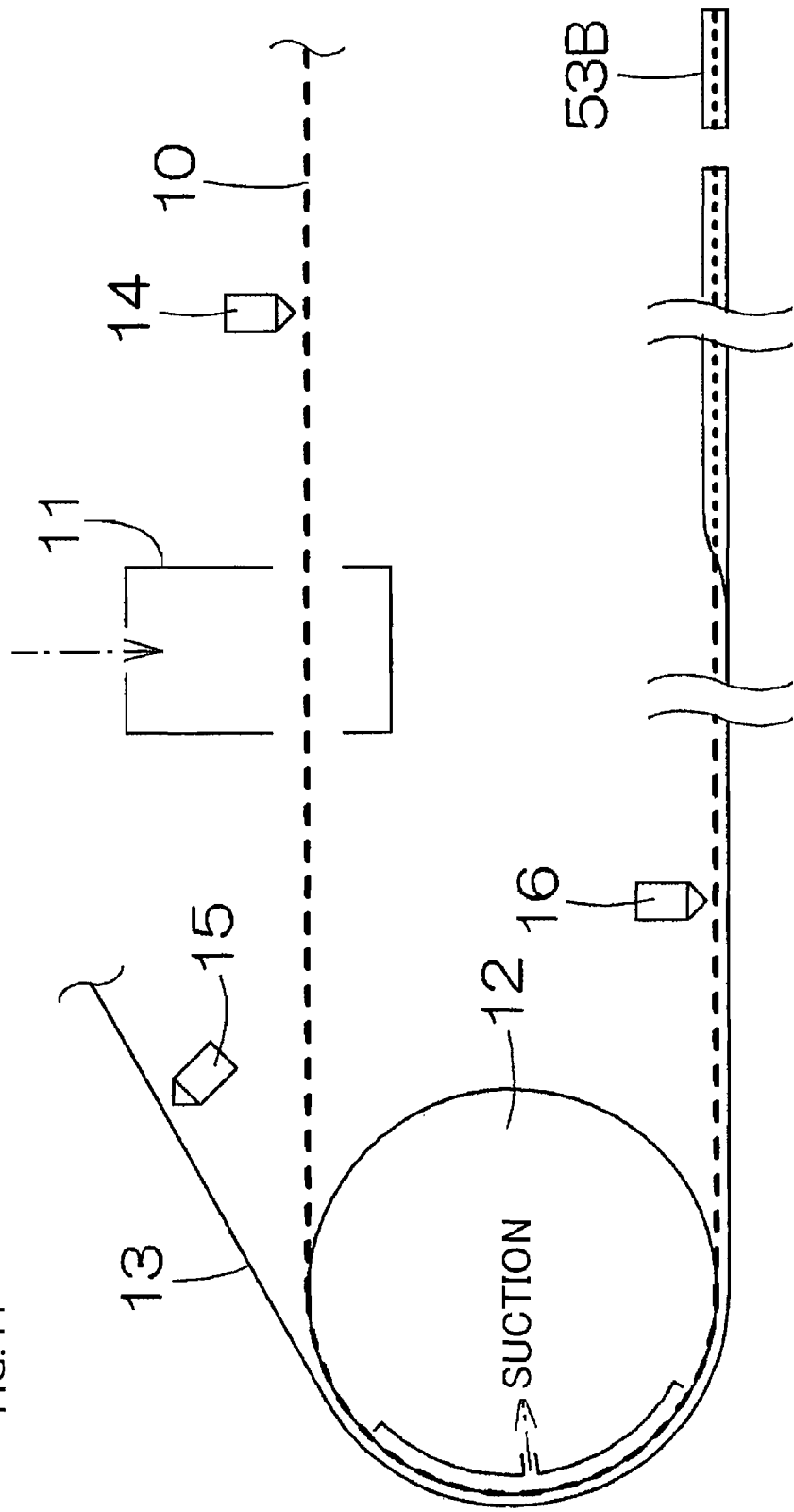
FIG. 11 is a schematic illustration showing a producing flow for an absorbent member.

FIG. 11 shows a flow for producing the absorbent member 53B. The assembly 10 of belt-shaped continuous fibers in tows having the preferable width and density is to be supplied to this producing line. Accordingly, the above producing line of assembly of fibers is connected to the producing line of the absorbent member so that the assembly 10 of the fibers can be directly introduced to the producing line of the absorbent member.

First, thus supplied assembly 10 of the fibers is fed through the polymer dispersion box 11, where the absorbent polymer, preferably super absorbent polymer is dispersed on the upper surface of the assembly 10. Next, the assembly 10 of the fibers is fed to the suction drum 12, which is adapted to suck inwardly at its predetermined peripheral range (in the drawing, substantially left half) with a suction pump (not shown) through aspiration holes provided on the periphery of the suction drum 12. Then, the super absorbent polymer dispersed assembly 10 is guided with the suction drum 12 so as to contact with the external periphery of the suction drum 12. During this, suction is performed through the aspiration holes so that atmosphere is passed from the super absorbent polymer dispersion-side through the assembly of fibers to the other side. This passing allows the super absorbent polymer to move into the assembly 10 of fibers.

The super absorbent polymer particle used herein means "powder" as well as "particle". As the super absorbent polymer particle used in this embodiment, a super absorbent polymer particle used in an absorbent article of this kind can be used as it is. Then, its particle size is 100 to 1000 μm, preferably 150 to 400 μm. The material of the super absorbent polymer is not specifically limited, but the polymer having the water absorption of 60 g/g or more is preferable.

Polymer, which is able to absorb and retain the body fluid having e.g., 10 times as large as its own weight, can be used as the absorbent polymer. For example, there can be listed starch, cellulose, synthetic polymer and the like, concretely, starch-acrylic acid (salt) graft copolymer, saponified starch-acrylonitrile copolymer, crosslinked natriumcarboxymethyl-cellulose, acrylic acid (salt) copolymer and the like. As the shape of super absorbent polymer, that of commonly used polymer particle is preferable, however also other shapes can be used.

The super absorbent polymer having the absorption speed of 40 sec or lower is used preferably. If the absorption speed is higher than 40 sec, so-called reversing (the situation where the body fluid once absorbed into the absorbent member reverses outside again) will be caused easily.

The super absorbent polymer having the gel strength of 1000 Pa or higher is used preferably. The absorbent member includes the tows and becomes bulky. Then, such absorbent member can absorb the great amount of body fluid. After such absorption, the absorbent member will be sticky due to the great amount of body fluid. In this case, if the polymer having the above gel strength is moved into the tows, the sticky feeling can be efficiently decreased.

The dispersed amount (basis weight) of the super absorbent polymer can be determined desirably according to the absorption required for the application of the absorbent member. Although it cannot be assumed sweepingly, it can be, for example 3 to 400 g/m². In the assembly of fibers, the amount distribution of the dispersed super absorbent polymer, the density distribution and the fiber density are preferably uniform for the common application. However, in order to attain specific absorbing properties, they may be uneven according to these required properties.

To disperse the super absorbent polymer in the assembly of fibers, for example, the following method can be used. First, in the assembly of fibers, these fibers are enlarged in their width and opened. Next, the super absorbent polymer is dispersed on the one surface of the assembly of fibers. After that, the opposite other surface is faced to the suction drum or the like and sucked with the desirable sucking power. Thus, the dispersed polymer is moved into the assembly. It is preferable that the dispersion of the super absorbent polymer is performed after the addition of the binder.

It is particularly preferable that, after the dispersion of the super absorbent polymer on the assembly of fibers, each assembly of fibers is packed individually with a liquid permeable sheet such as crepe paper, a non-woven fabric, a perforated sheet or the like, or a liquid impermeable sheet such as a polyethylene film or the like.

It is also preferable that adhesive is coated on the assembly of fibers before dispersing the super absorbent polymer in order to fix it on the assembly of fibers.

Further, it is also preferable that when each assembly is packed individually with the sheet, the packing sheet is previously coated with adhesive on its surface, which faces the assembly of fibers.

Further, it is particularly preferable that after the dispersion of super absorbent polymer, the assembly 10 is further covered with a sheet 13 at its polymer-dispersed surface. In this case, the assembly 10 is sucked from the opposite surface. By covering the assembly with the sheet 13 before suction, the suction pressure applied to the super absorbent polymer is increased comparing with an assembly without such cover. Thus, the super absorbent polymer can be efficiently moved into and dispersed in the assembly of fibers. As the sheet 13 used here, there can be listed a liquid permeable sheet such as crepe paper, a non-woven fabric, a perforated sheet or the like and a liquid impermeable sheet such as a polyethylene film or the like.

It is also preferable that adhesive is coated on the assembly 10 of fibers before the dispersion of the super absorbent polymer, in order to fix it on the assembly 10. For attaining this, as shown in the drawing, the adhesive applicator 14 may be provided upstream with respect to the polymer dispersion box 11.

Further, it is also preferable that when each assembly is packed individually with the sheet 13, the packing sheet 13 is previously coated with adhesive on its surface, which faces the assembly of fibers. For attaining this, as shown in the drawing, the adhesive applicator 15 is provided on the line for introducing the sheet to the suction drum. By doing so, a part of super absorbent polymer, which is exposed to the surface of the assembly 10 of fibers, is fixed on the sheet 13 with the adhesive, while the unfixed super absorbent polymer is moved into the assembly 10 of fibers by the suction later.

After the suction, that is, after the super absorbent polymer is moved to the assembly 10, it is also preferable that adhesive is applied to the assembly 10 of fibers. For attaining this, as shown in the drawing, the adhesive applicator 16 is provided downstream with respect to the suction drum 12 so as to face to the exposed surface (the opposite surface to the sheet 13, the upper surface in the drawing) of the assembly 10 of fibers. As stated above, in the suction, the part of super absorbent polymer is dispersed on the surface of the assembly 10 of fibers, while the rest of super absorbent polymer is moved to the opposite surface of the assembly 10 of fibers. In this respect, due to the above application of adhesive with the applicator 16, the rest of super absorbent polymer can be fixed on the opposite surface. Additionally, when this opposite surface is covered with another sheet, or when the opposite surface is covered with the sheet 13 by folding the both side portions of the sheet 13 around the both side edges of the opposite surface, the super absorbent polymer, which is moved on the exposed surface of the assembly 10, can be fixed on the sheet 13 with the adhesive.

In the above applications of adhesive, any application or more than any two applications can be performed. As the adhesive, thermoplastic resin (concrete examples are stated before) can be used preferably.

As explained before, the super absorbent polymer dispersed assembly 10 is covered with the other sheet, alternatively, the assembly 10 is covered with the sheet 13 by folding its both side portions around the both side edges of the assembly 10 with a folding member. Then, as shown in the drawing, the resultant assembly 10 of fibers is cut to individual absorbent members 53B each having the predetermined length.

In the assembly 10 of fibers, the amount distribution of the dispersed super absorbent polymer, the density distribution and the fiber density are preferably uniform for the common application. However, in order to attain specific absorbing properties, they may be uneven according to these required properties.

In the application performed as shown in the drawing, in the polymer dispersion box 11, the super absorbent polymer can be unevenly dispersed to the width direction of the assembly 10 of fibers. Particularly, in the body fluid absorbent article such as a disposable diaper, a sanitary napkin or the like, it is often required that the absorption should be increased in the middle portion of the absorbent member in its width direction. For attaining this, in the polymer dispersion box 11, the amount of dispersed super absorbent polymer can be adjusted so as to be larger to the above middle portion than that to the above both side portions.

Further, by adjusting the suction strength in the suction drum 12 so as to be unevenly distributed, the density of the super absorbent polymer can be unevenly distributed. Precisely, in the suction drum 12, the higher the suction strength is, the larger amount of super absorbent polymer is moved to the suction drum 12-side. On the basis of this fact, the density of the super absorbent polymer can be adjusted in the assembly 10 of fibers as stated below. The density of the super absorbent polymer in the middle portion of the assembly 10 of fibers in its width direction can be larger than that of the both side portions of the assembly 10 of fibers by adjusting the suction strength of the middle portion of the suction drum 12 in its width direction so as to be larger than the suction strength of the both side portions of the suction drum 12 (alternatively, by adjusting the suction time of the middle portion so as to be longer than the suction time of the both side portions). In this way, the absorption speed is decreased in the middle portion of the assembly 10 of fibers while the absorption speed is increased in the both side portions. Accordingly, when this assembly 10 is used for the body fluid absorbent article, the body fluid can be easily diffused in the whole of the absorbent body, that is to say, the diffusing performance is improved.

Further, in the assembly 10 of fibers in tows, liquid easily flows along the direction of continuous fiber. Accordingly, by adjusting the fiber density in the assembly 10 of fibers so as to be unevenly distributed, specific absorbing properties can be obtained. Precisely, for attaining such unevenly distribution of the fiber density, in producing the assembly 10 of fibers, the fibers are unevenly opened, alternatively, plural tows are partly used in the form of bundles, and the like. Concretely, for example, the fiber density may be adjusted so as to be higher in the middle portion of the assembly 10 of fibers in its width direction than that in the both side portions. In this way, in the middle portion of the assembly 10 in its width direction, the larger amount of fluid can flow along the direction of the continuous fiber.

In this embodiment, the construction of the absorbent member 53A and of the absorbent member 53B is not specifically limited. For example, there may be core like, a single sheet, a sheet layer consisting of laminating 2, 3, 4 or more sheets and the like.

(Covering Sheet 358)

As the covering sheet 358 used for covering the absorbent member 53B, there can be used tissue paper, particularly crepe paper, a non-woven fabric, a polyethylene laminated non-woven fabric, a perforated sheet and the like. However, it is preferable that the super absorbent polymer particle 354 can be prevented from going through the covering sheet 358. When the non-woven fabric is used instead of the crepe paper, a hydrophilic SMMS (spunbond/meltblown/meltblown/spunbond) non-woven fabric is specifically preferable. This non-woven fabric may be made of polypropylene, polyethylene/polypropylene, and the like. The basis weight of this covering sheet is preferably 8 to 20 g/m$^2$, more preferably 10 to 15 g/m$^2$.

(Absorbent Sheet 55)

In this embodiment, the absorbent sheet 55 is body fluid permeable. Accordingly, what is required for the material of the absorbent sheet 55 is only this body fluid permeability. For example, there can be exemplified the similar material as that of the face sheet 51, similar material as that of the body fluid permeable absorbent member 52, and the like.

(Body Fluid Diffusion Sheet 58)

In this embodiment, the body fluid diffusion sheet 58 is body fluid diffusible. Accordingly, what is required for the material of the body fluid diffusion sheet 58 is only the body fluid diffusibility. For example, there can be listed the similar material as that of the face sheet 51, similar material as that of the body fluid permeable absorbent member 52, and the like. Here, spunlace, a pulp non-woven fabric, a mixed sheet of pulp and rayon, pointbond, and crepe paper are particularly preferable.

(Holding Sheet 380)

The holding sheet 380 is adapted to eliminate or reduce the discomfort feeling of the roughness. Accordingly, the material of the holding sheet 380 is not specifically limited and what is required for it is holding ability for the absorbent polymer. There can be exemplified, for example, a non-woven fabric, crimped pulp, a low absorbent cotton fiber (e.g., un-degreased cotton fiber, degreased cotton fiber, treated rayon fiber with water repellant agent or hydrophobizing agent or the like), polyethylene fiber, polyester fiber, acrylic fiber, polypropylene fiber, silk, cotton, hemp, nylon, polyurethane, acetate fiber and the like.

When the non-woven fabric is used as the holding sheet 380, the non-woven fabric has preferably the work of compression of 0.01 to 10.00 gf·cm/cm$^2$, more preferably 0.01 to 1.00 gf·cm/cm$^2$ based on KES test. Then, it has preferably the compressive resilience of 10 to 100%, more preferably 70 to 100% based on KES test.

(Body Fluid Impermeable Sheet 370)

As stated before, the body fluid impermeable sheet 370 is just disposed on the under surface-side of the absorbent member 53B. Accordingly, the material of the body fluid impermeable sheet 370 is not specifically limited. Concretely, there can be exemplified, for example, olefin resin such as polyethylene resin, polypropylene resin, or the like, a laminated non-woven fabric formed by laminating a non-woven fabric on a polyethylene sheet, a substantially impermeable non-woven fabric, whose impermeability is caused by combined waterproof film (in this case, the body fluid impermeable sheet is formed with the waterproof film and the non-woven fabric) and the like. It is needless to say that other than these materials, there can be listed liquid impervious but moisture permeable material, which is often used in these days because of its resistance to stuffy feeling. As this liquid impervious but moisture permeable material, for example, a slightly porous sheet can be listed. This is produced in the following way. First, inorganic filler is kneaded with olefin resin such as polyethylene resin, polypropylene resin, or the like so as to form a sheet. Then, this sheet is subjected to uniaxial drawing or biaxial drawing so that the slightly porous sheet can be obtained.

(Back Sheet 2)

In this embodiment, the back sheet 54 is body fluid impermeable. Accordingly, what is required for the material of the back sheet 54 is this fluid impermeability. Concretely, there can be exemplified, for example, olefin resin such as polyethylene resin, polypropylene resin, or the like, a laminated non-oven fabric formed by laminating a non-woven fabric on polyethylene sheet or the like, a substantially impermeable non-woven fabric, whose impermeability is caused by combined waterproof film (in this case, the body fluid impermeable sheet 54 is formed with the waterproof film and the non-woven fabric) and the like. It is needless to say that other than these materials, there can be listed liquid impervious but moisture permeable material, which is often used in these days because of its resistance to stuffy feeling. As this liquid impervious but moisture permeable material, for example, a slightly porous sheet can be listed. This is produced in the following way. First, inorganic filler is kneaded with olefin resin such as polyethylene resin, polypropylene resin, or the like so as to form a sheet. Then, this sheet is subjected to uniaxial drawing or biaxial drawing so that the slightly porous sheet can be obtained.

Example 1

Now, the effect of the present invention will be cleared by way of examples.

The present inventors performed the tests for measuring the absorption speed into the body fluid absorbent structures 50 of the first embodiment and that into a conventional body fluid absorbent structure. In the body fluid absorbent structure 50, the assembly of cellulose acetate fibers in tows was used in the body fluid permeable absorbent member 52. On the other hand, in the conventional body fluid absorbent structure, the non-woven fabric was used instead of the body fluid permeable absorbent member 52. As for the absorbed amount, there were 6 kinds; 5 cc, 10 cc, 15 cc, 20 cc, and 30 cc. It should be noted that when the amount was 10 cc or more, all of the water was not absorbed once. Precisely, in each test, 5 cc of water was tested with a cylinder and this is repeated twice to 6 times at 20 minutes interval. The times (sec) required for the absorption were shown in Table 1.

TABLE 1

| | Material of body fluid permeable absorbent member | | |
|---|---|---|---|
| | Absorption (cc) | Cellulose acetate | Non-woven fabric | Comparison (times) |
| Test example 1 | 5 | 0.92 seconds | 2.37 seconds | 2.6 |
| Test example 2 | 10 | 1.51 seconds | 8.11 seconds | 5.4 |
| Test example 3 | 15 | 1.99 seconds | 10.54 seconds | 5.3 |
| Test example 4 | 20 | 2.65 seconds | 13.09 seconds | 4.9 |
| Test example 5 | 25 | 3.11 seconds | 19.43 seconds | 6.2 |
| Test example 6 | 30 | 3.35 seconds | 29.83 seconds | 8.9 |

Table 1 shows that the absorption speed in the absorbent structure using the cellulose acetate was higher than that in the conventional structure. Particularly, as the water absorption was increased, the difference of absorption speed was also increased, between the absorbent structure using the cellulose acetate and the conventional structure. This fact indicates that instead of the non-woven fabric, the assembly of cellulose acetate fibers in tows is preferably used in the body fluid permeable absorbent member 52.

Example 2

Next, the relation between the basis weight of the binder and stiffness and the relation between the basis weight of the binder and body fluid absorption speed were examined through the tests.

(Stiffness Test)

As the binder, triacetin was used. Several kinds of basis weight of triacetin were added to the assembly of fibers. Then, each assembly was used as the absorbent member 53B in each sample.

Each sample was dried for 12 hours in a drafter adjusted at the temperature of 25° and the humidity of 60%. The thickness of the dried sample was used as the thickness before absorbing the body fluid. Next, 5 cc of horse blood was dropped freely to the dried sample and absorbed there. Then, this sample was left for 5 minutes. The thickness of such sample was used as the thickness after absorbing the body fluid. The thickness after absorbing the body fluid/the thickness before absorbing the body fluid was calculated. Thus, the result of such division was determined as the thickness sustainability. Large thickness sustainability means that the absorbent member 53B can keep its stiffness, while the small thickness sustainability means that the absorbent member 53B loses its stiffness. The thickness was measured with Handy-Type Compression Tester (KES-G5:KATO TECH CO., LTD.). The results of this test and the basis weight of the dispersed binder were shown in Table 2.

[Table 2]

Table 2 shows that, as for the absorbent member 53B formed by dispersing the binder to the assembly of fibers in tows, as the added amount of binder was increased, the thickness sustainability of the absorbent member 53B was improved, which means that the member 53B did not lose its stiffness so easily. Additionally, when the basis weight of the dispersed binder was 17 g/m$^2$ or more, the thickness sustainability was not significantly changed. Accordingly, when the triacetin is used as the binder, the preferable basis weight of the dispersed binder is about 16 to 18 g/m$^2$. The density of the assembly of fibers used in the sample was 30 g/m$^2$.

(Body Fluid Absorption Speed Test)

As the binder, triacetin was used. By changing the basis weight of triacetin, several kinds of assemblies were provided. Then, several kinds of absorbent members 53B comprising these assemblies of fibers were used in samples. In each sample, the top sheet 51 made of a perforated film was laminated on the upper surface of the absorbent member 53B while the absorbent member 61 made of finely divided pulp was laminated on the under surface of the absorbent member 53B. Before laminating, the top sheet 51, the absorbent member 53B and the absorbent member 61 were dried for 12 hours in a drafter adjusted at the temperature of 25° and the humidity of 60%. Additionally, a blank sample was provided for each test.

In each test, 5 cc of horse blood was dropped to the laminated sample from the top sheet 51-side and absorbed there and this was repeated 6 times at 20 minutes interval. Then, the absorption speed of the horse blood in each dropping was measured. The basis weights of the binders were same as that of each sample in the stiffness test. The results were shown in Table 3.

TABLE 2

| | Test example 7 | Test example 8 | Test example 9 | Test example 10 | Test example 11 | Test example 12 | Test example 13 | Test example 14 | Test example 15 | Test example 16 | Test example 17 |
|---|---|---|---|---|---|---|---|---|---|---|---|
| Basis weight of triacetin (g/m$^2$) | 0 | 2.4 | 4.9 | 7.3 | 9.8 | 12.2 | 14.6 | 17.1 | 19.5 | 22.0 | 24.4 |
| Thickness before absorption (mm) | 22.0 | 21.0 | 20.0 | 18.0 | 18.0 | 17.0 | 17.0 | 16.5 | 16.5 | 16.0 | 14.5 |
| Thickness after absorption of 5 cc (mm) | 9.8 | 10.5 | 10.5 | 10.7 | 11.0 | 11.0 | 11.5 | 12.0 | 12.1 | 11.6 | 10.5 |
| Thickness sustainability (%) | 44.5 | 49.8 | 52.5 | 59.5 | 61.1 | 64.7 | 67.6 | 72.7 | 73.3 | 72.5 | 72.4 |

[Table 3]

Table 3 shows that by adding the binder to the assembly of fibers, these fibers are contacted each other in the form of dot or line, which improves the absorption speed.

Therefore, by adding the binder for the contact of the fibers in the form of dot or line, the absorption speed as well as the thickness sustainability was improved. Finally, the resultant absorbent member 53B has advantages of high body fluid absorbing power and improved fitting for the wearer.

Example 3

Figure 73:
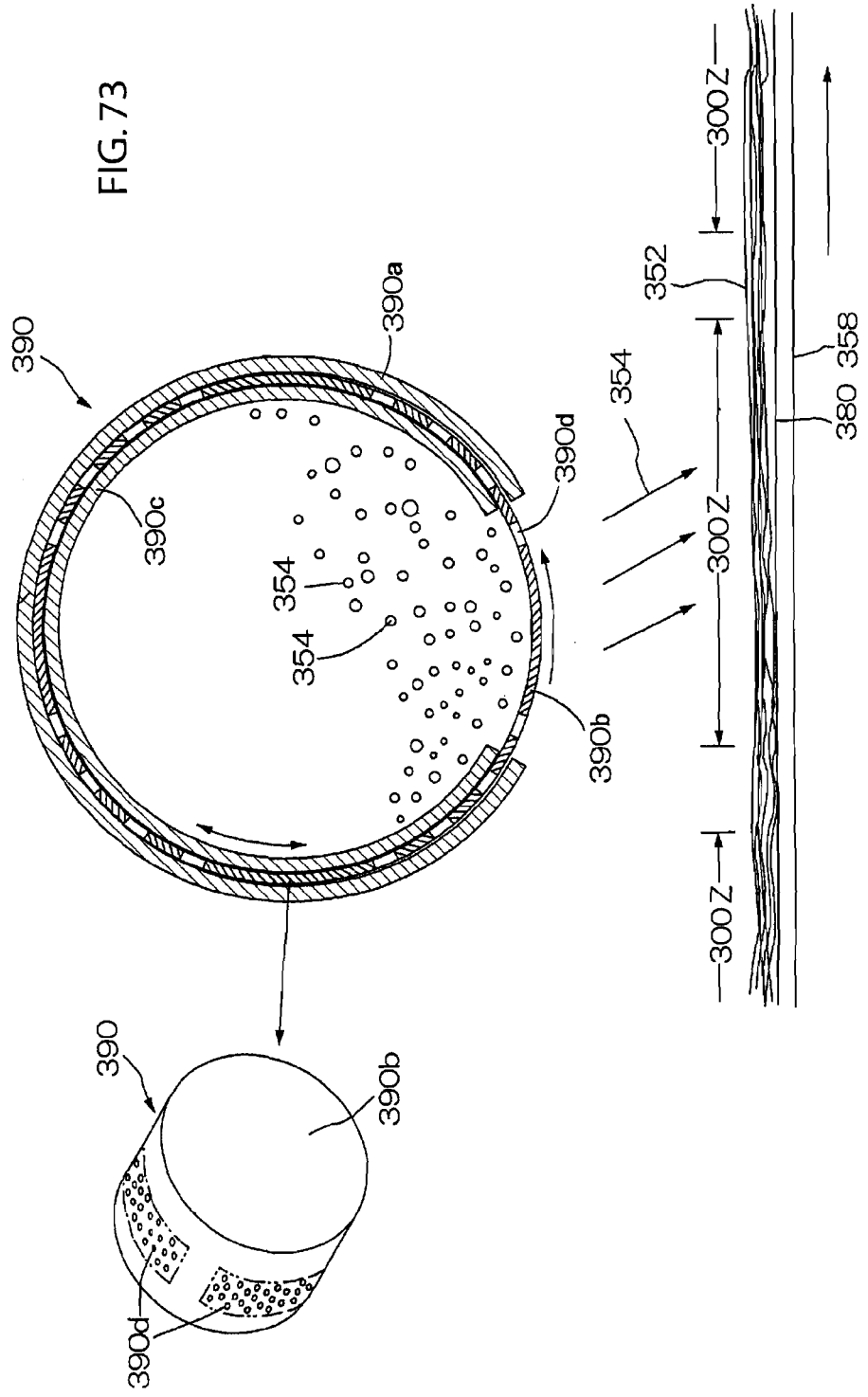
FIG. 73 is a schematic illustration showing means for dispersing super absorbent polymer particles.
Figure 74:
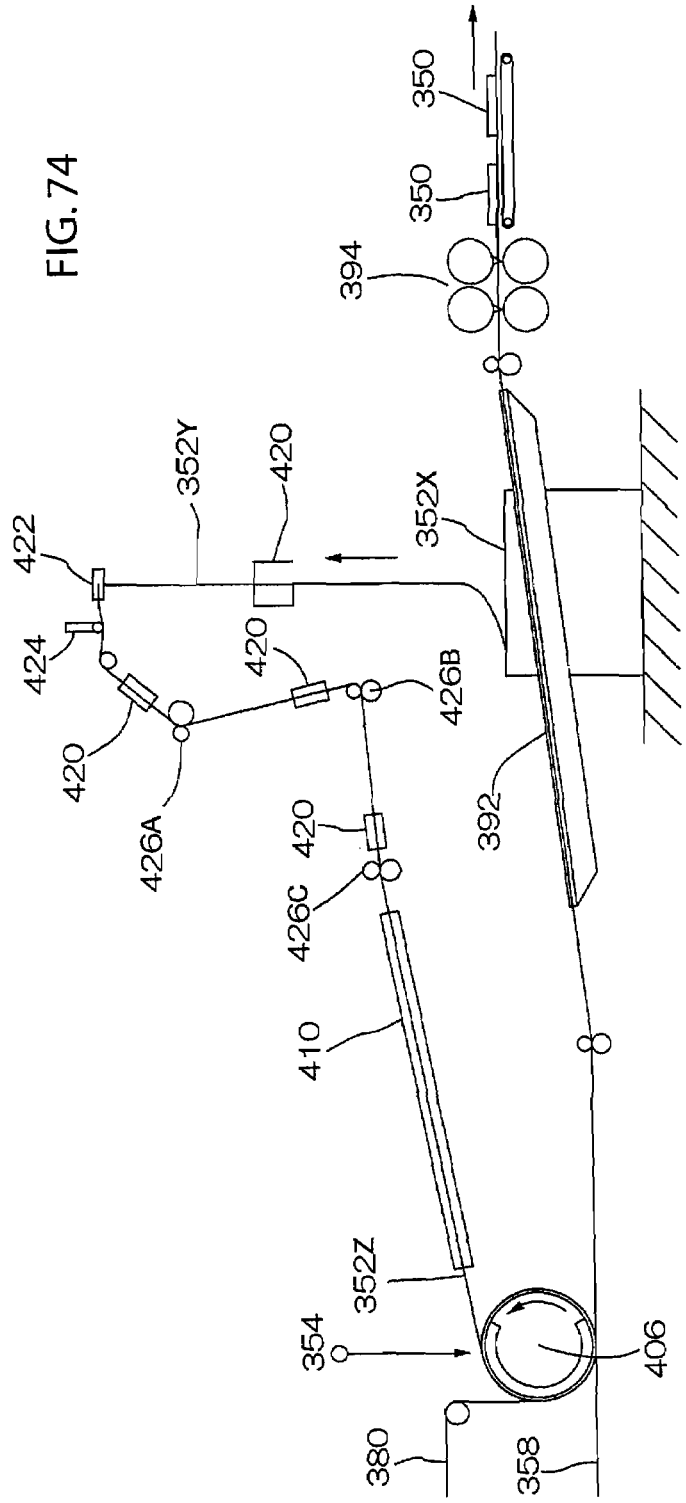
FIG. 74 is a schematic illustration showing another means for dispersing super absorbent polymer particles.

First, the assembly of filaments, which were formed by opening the cellulose diacetate fibers in tows, was used in the producing method shown in FIGS. 69 and 70. Thus, the absorbent member and the absorbent article were obtained for Test example 18 (example according to this invention). Next, using short pulp fibers, the common absorbent member and the common absorbent article were obtained for Test example 19 (conventional example). Finally, the assembly of filaments was used in the producing method shown in FIG. 73. Thus, the absorbent member and the absorbent article were obtained for Test example 20 (comparative example). Detailed explanation about Test example 20 will be stated. In the producing method of Test example 18, as shown in FIG. 71, due to the super absorbent polymer particle disperse means 390, the super absorbent polymer particles 354 are fallen with their own weight, in addition, the component of centrifugal force is also applied to the super absorbent polymer particles. On the other hand, in the producing method of Test example 20, as shown in FIG. 73, the vacuum roll 406 was used instead of the inversion roll of FIG. 70. Then, the super absorbent polymer particles 354 were dispersed on the assembly 352Z of filaments 352, through the means of super absorbent polymer particle disperse means, from the top-side of the vacuum roll 406. In this case, since this means was common lower portion of assembly 352Z of filaments 352 so as not to reach the upper portion (That is, "the super absorbent polymer particles are not substantially dispersed in the full length of thickness of the assembly of filaments").

(Measurement of Absorption of Super Absorbent Polymer Particles)

First, 500.00±0.10 g of 0.9% solution of sodium chloride (prepared by dissolving 9.00 g of special great chemical sodium chloride into 991.0 g of ion exchange water) was fed into an 1 L beaker containing a rotator. Next, 2.0000±0.0002 g of sample was added to the liquid while the liquid was stirred with a magnetic stirrer. Then, the beaker was covered with Saran Wrap and the stirring was continued for one hour.

Subsequently, the content of the beaker was filtered with a standard sieve (38 μm, 200 mm φ×45 mm). The gel remained on the surface of the sieve was drained with a Teflon plate and it was left for 15 minutes. Finally, the weight A of the remained gel on the surface of the sieve was measured and the absorption was obtained from the following equation.

$$C = A/S \quad (1)$$

TABLE 3

|  | Test example 7 | Test example 8 | Test example 9 | Test example 10 | Test example 11 | Test example 12 | Test example 13 | Test example 14 | Test example 15 | Test example 16 | Test example 17 |
|---|---|---|---|---|---|---|---|---|---|---|---|
| Basis weight of binder (g/m$^2$) | 0.0 | 2.4 | 4.9 | 7.3 | 9.8 | 12.2 | 14.6 | 17.1 | 19.5 | 22.0 | 24.4 |
| Drop of 5 cc | 1.08 | 0.94 | 0.84 | 0.84 | 0.80 | 0.85 | 0.75 | 0.89 | 0.76 | 0.76 | 0.81 |
| Drop of 10 cc | 1.01 | 1.06 | 0.99 | 1.14 | 1.23 | 1.22 | 1.01 | 1.31 | 1.35 | 1.00 | 0.97 |
| Drop of 15 cc | 1.63 | 1.45 | 1.77 | 1.41 | 1.73 | 1.73 | 1.41 | 1.89 | 1.64 | 1.52 | 1.56 |
| Drop of 20 cc | 2.37 | 2.25 | 2.01 | 2.12 | 2.13 | 2.17 | 2.24 | 2.57 | 2.15 | 1.90 | 1.99 |
| Drop of 25 cc | 3.54 | 3.33 | 3.08 | 2.78 | 2.65 | 2.40 | 2.30 | 2.52 | 2.41 | 2.36 | 2.49 |
| Drop of 30 cc | 4.00 | 3.92 | 3.65 | 3.39 | 3.09 | 3.19 | 2.91 | 2.84 | 2.74 | 2.60 | 2.65 | type, the component of centrifugal force stated before was not applied. That is to say, the super absorbent polymer particles were fallen only with their own weight. For these three Test examples 18, 19 and 20, several measurements were performed, as stated after. Table 4 included the results of the measurements and evaluations.

In the article used in the comparative example, the super absorbent polymer particles 354 are mainly located on the holding sheet and the small part of them are dispersed only the Wherein, C was the amount of absorbed saline (g/g), A was the weight of the gel remained on the surface of the sieve (g), and S was the weight of the sample (g).

(Measurement of Retaining Capacity of Super Absorbent Polymer Particles)

0.9% solution of sodium chloride was fed into a stainless container until the liquid volume comes to 80% of the container volume. Next, 2.0000±0.0002 g of sample

TABLE 4

|  |  | Test example 18 | Test example 19 | Test example 20 |
|---|---|---|---|---|
| Super absorbent polymer | Amount of SAP (g) | 11 | 11 | 12 |
|  | Basis weight of SAP (g/cm$^2$) | 0.02 | 0.0200 | 0.0312 |
|  | Absorption (g/g) | 52 | 53 | 54 |
|  | Retaining capacity (g/g) | 32 | 34 | 35 |
|  | Absorption speed (sec) | 39 | 40 | 27 |
|  | Absorption under pressure (ml/g) | 33 | 33 | 30 |
|  | Gel strength (Pa) | 1000 | 700 | 2300 |
| Assembly of fibers | Amount of fiber (g) | 3.0 | 9.0 | 3.0 |
|  | Fiber density (g/cm$^3$) | 0.044 | — | — |
|  | Basis weight of fiber (g/cm$^2$) | 0.006 | 0.0164 | 0.0078 |
| Absorbent member | Area of absorbent member (cm$^2$) | 539 | 520 | 410 |
|  | Thickness of absorbent member (cm) | 1.0 | 1.0 | 1.1 |
|  | Weight of absorbent member (g) | 14 | 20 | 16 |
| Absorbing power in condition of diaper | Absorption under pressure (g) | 480 | 520 | 500 |
|  | Absorption speed (sec) | 260 | 238 | 1560 |
|  | Amount of reversing (g) | 3.0 | 7.0 | 9.0 |
| Compressive property of absorbent member | Work of compression WC (gf·cm/cm$^2$) | 4.0-7.0 | 2.5 | 8.1 |
|  | Compressive resilience RC (%) | 46 | 43 | 36 |
|  | Sensory test of recovery after compression | ○ | — | Δ | was weighed precisely and put into a cotton bag (cotton broad #60, 100 mm×200 mm). Then, about 100 ml of 0.9% solution of sodium chloride was poured into the cotton bag. At the same time, the whole of the cotton bag bound with a rubber band was immersed in the solution of the stainless container for 15 minutes.

After that, the cotton bag was dried with a spin dryer (167G) and the weight of the cotton bag and that of gel were measured.

The same operation was repeated except that the sample was not included in the cotton bag. The weight of the empty cotton bag in wet was measured.

The retaining capacity was obtained from the following equation.

$$C=(A-B)/S \qquad (2)$$

Wherein, C was retaining capacity (g/g), A was the weight of the sum of cotton bag and gel (g) and S was the weight of the sample (g).

(Measurement of Absorption Speed of Super Absorbent Polymer)

First, 50.00±0.01 g of 0.9% solution of sodium chloride was fed into an 100 ml beaker containing a rotator, which was, then, kept at the temperature of 25±0.2° C. in a constant-temperature water bath.

Next, with a magnetic stirrer and a measuring instrument for the rotator, the solution was stirred with the rotation speed of 600±10 rpm.

Then, 2.0000±0.0002 g of sample was weighed. This sample was put into the vortex in the beaker. At the same time, the measurement of the absorption speed was started with a stopwatch and each absorption speed was recorded. In this case, the absorption speed was the time (sec) taken since the sample was put into the beaker until the vortex was eliminated and the liquid level became horizontal.

(Measurement of Absorption of Super Absorbent Polymer Under Pressure)

Figure 77:
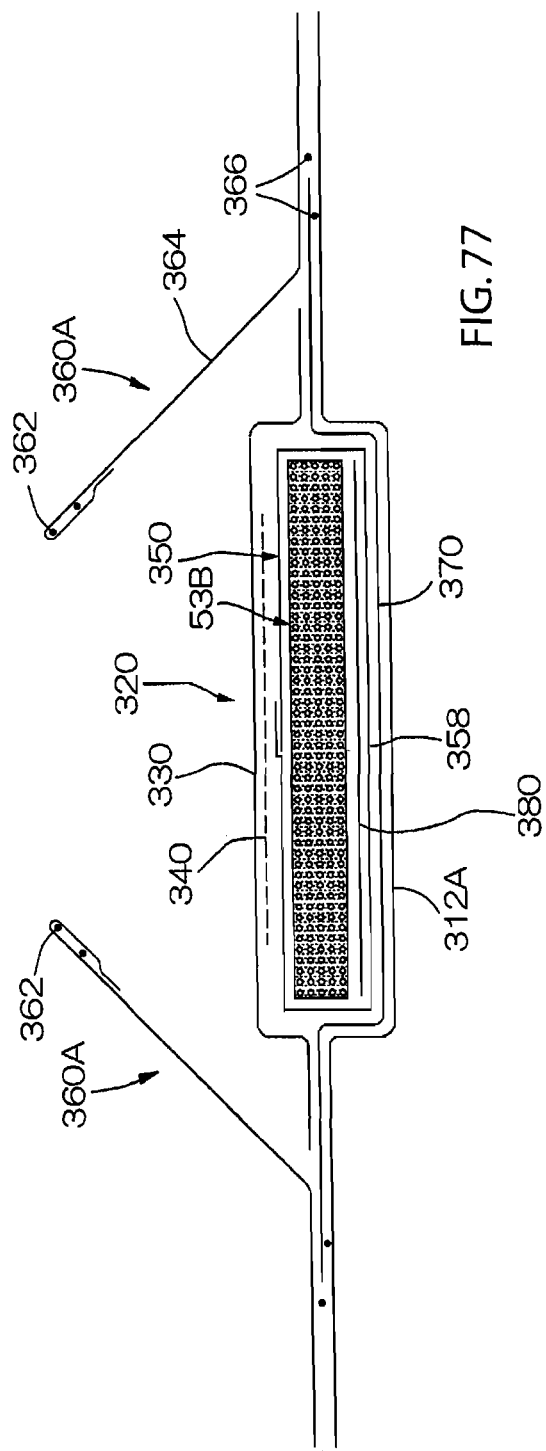
FIG. 77 is a cross section taken on half line of FIG. 75.

As shown in FIG. 77, the acrylic resin cylinder 503 (inner diameter; 2 cm, height; 5 cm, it is equipped at its bottom with a nylon net 501 N having the opening of 75 μm) was provided vertically on the support table 501 so as to be coaxial with a through hole provided at the center of the support table 501. Next, 0.100±0.0002 g of sample 500 was put into the cylinder 503. Further, cylindrical weight 502 (diameter; 1.9 cm, weight; 120 g) was placed on the sample 500.

Then, the outlet of the burette 504 (containing 0.9% solution of sodium chloride) was communicated with the under side opening of the through hole of the support table 501 through the tube 506. The scale of burette 504 was read before opening the valves 300 V1, 300 V2 for starting the absorption. Then, the valves 300V1, 300V2 are opened so that the 0.9% solution of sodium chloride was fed from the burette 504 to the cylinder 503. Subsequently, when 30 minutes had passed since the opening of the valves 300 V1, 300V2, the scale of burette 504 was read again.

The absorption under pressure was obtained from the following equation.

$$C=(A-B)/S \qquad (3)$$

Wherein, C was the absorption under pressure (g/g), A was the scale when 30 minutes had passed since the opening of the valves (ml), B was the scale before the opening of the valves (ml) and S was the weight of the sample (g).

(Measurement of Gel Strength of Super Absorbent Polymer)

First, 20.0 g of urea, 8.0 g of sodium chloride, 0.3 g of calcium chloride, 0.8 g of magnesium sulfate, 970.9 g of ion exchange water and 0.25 g of ferrous sulfate were mixed so as to prepare totally 1 L of artificial urine (ferrous ion 50 ppm).

Next, 49±0.1 g of artificial urine including 50 ppm of ferrous ion was fed into an 100 ml beaker containing a rotator. Then, the artificial urine was stirred with a magnetic stirrer. Subsequently, 1.0000±0.0002 g of sample was weighed and was put into the vortex in the beaker. After that, the content of the beaker was stirred until the vortex was eliminated and the liquid level became horizontal.

Thus resultant gel was left for 3 hours in a box in which constant temperature (40° C.) and constant humidity (60% RH) was maintained.

Then, the gel was soaked for 5 minutes in a constant-temperature water bath (25° C.). Finally, the measurement of the gel strength of the gel was performed with Neocard Meter. Conversion of unit was performed for this result through the following equation so that the gel strength (Pa) was obtained.

$$C=A \times 0.1 \qquad (4)$$

Wherein C was gel strength (Pa), A was gel strength (dyne/cm$^2$) resulted from Neocard Meter and 0.1 was constant.

(Measurement of Absorption Under Pressure in Application to Disposable Diaper)

First, the weight of a sample, into which liquid was not absorbed yet, was measured.

Figure 78:
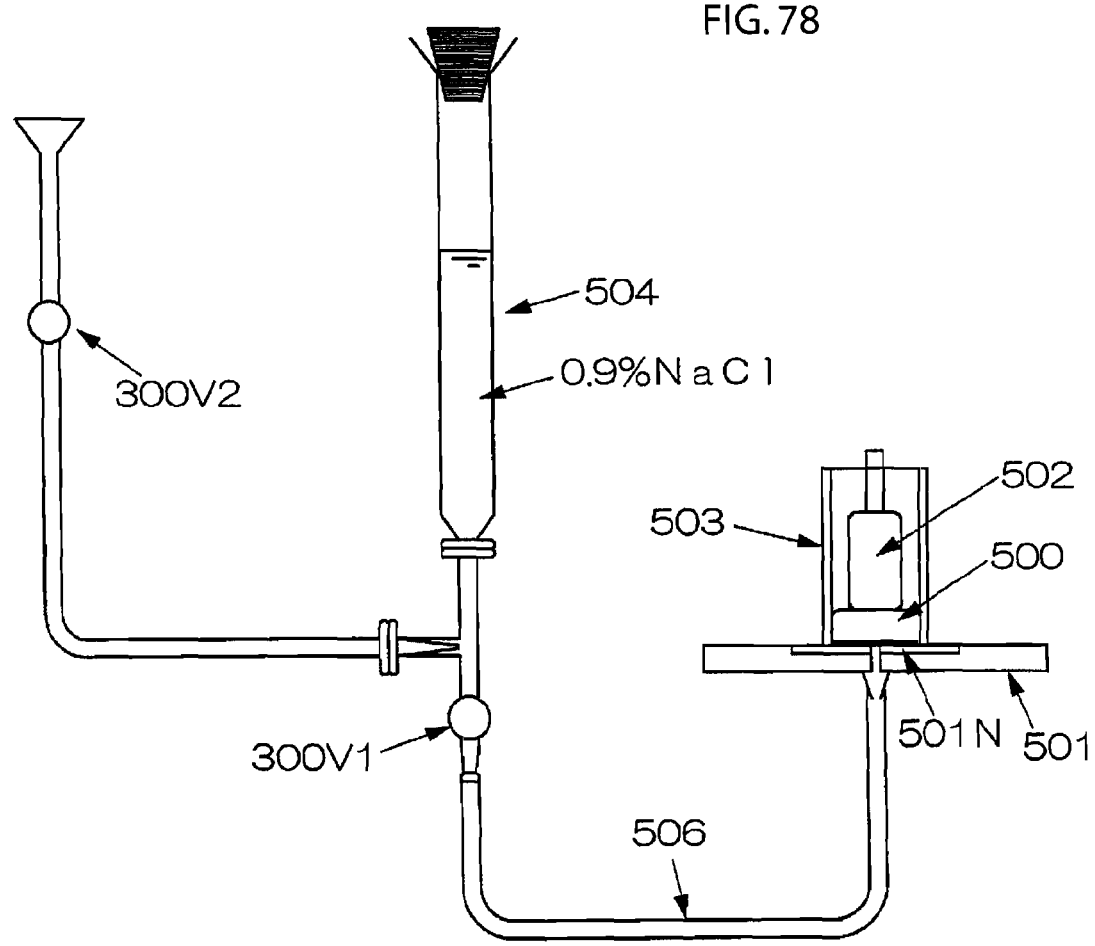
FIG. 78 is a schematic illustration of experimental apparatus.
Figure 79:
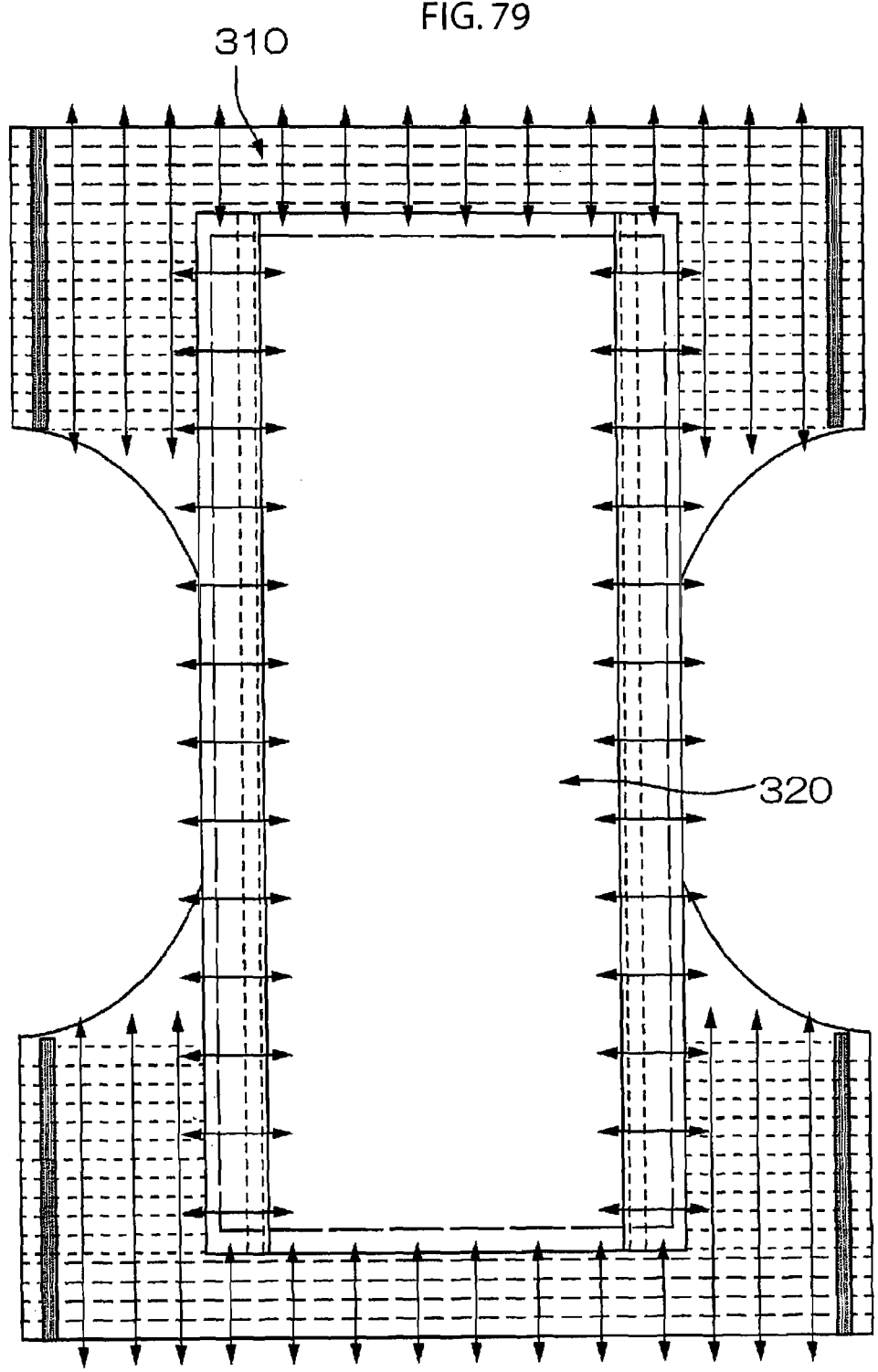
FIG. 79 is a plan view of a developed disposable diaper for explaining a test sample.

In a disposable diaper, there are contracting portions shown in a waist zone, gather zones or the like, formed by rubber strands or the like. Then, in these contracting portions, as the two-headed arrows shown in FIG. 78, the cutting lines were arranged with separation of 2 cm. In this way, the diaper could be flat without application of any force (naturally).

Then, this sample was disposed between an acrylic plate and a metal plate, while the wearer-side surface (internal surface) of the sample was faced up. A weight (10 kg) was placed on the acrylic plate. Thus, the resultant sample set was soaked for 30 minutes in the artificial urine (stated above), which was kept at the temperature of 37° C.

After that, the sample set was pulled out from the artificial urine. Then, the weight and the plates were removed from the sample set. The rest sample was fold into three and weighed with a scale.

Finally, the absorption under pressure was obtained by subtraction of the first weight of the sample, into which liquid was not absorbed yet, from the last weight of the sample, into which the artificial urine was absorbed.

(Measurement of Absorption Speed in Application to Disposable Diaper)

First, a rectangular plate was bent so as to have a U-shape. Such shape was likened abstractly to the part of human body from his or her crotch to hips. Further, this U-member has an inlet at the center in the direction of the width of this member in its bottom.

Next, in an absorbent structure of a disposable diaper as a sample, the center in the longitudinal direction was marked. Then, this sample was applied externally to the U-member so that the marked center of the sample corresponded to the center of the bottom of the U-member.

Then, the U-member equipped with the sample was placed on a hammock so that the U-member was supported by the hammock stably so as not to slant.

Subsequently, a weight (1 kg, 10 cm×10 cm) having a through hole at its center was put on the U-member. In this case, the through hole was corresponded to the inlet of the U-member.

Further, 100 cc of the artificial urine (stated before) was poured into the sample through the through hole of the weight and the inlet of the U-member. Finally, the time required for the absorption of all poured urine was measured as the absorption speed (seconds).

(Measurement of Reversed Amount in Application to Disposable Diaper)

First, an absorbent structure was cut into a piece having the dimension of 100 mm×100 mm. Then, this piece was covered with a top sheet and then, four side edges are sealed to form a sample.

Next, a cylinder having the inner diameter of 27 mm (with a support having the dimension of 150 mm×150 mm) was placed on the center of the sample. The cylinder was weighted as desired.

Then, with the cylinder, 50 cc of the artificial urine was dropped to the sample three times at the interval of 10 minutes.

After 10 minutes from the third dropping, filter papers (ADVANTEC No. 2 10 cm×10 cm, stacked in 30 sheets) are put on the sample. After weighting for 10 seconds by a weight of 5 kg, the weight of papers was measured. Finally, the amount of the artificial urine reversed into the papers was obtained as the reversed amount (g) by subtraction of the previously measured weight of the papers, into which the urine was not absorbed yet, from the last weight of the papers, into which the artificial urine was absorbed.

(Measurement of Compressive Resilience RC and Work of Compression WC)

A sample was compressed, with a compression tester by KATO TECH CO., LTD. The conditions were Speed: 0.01 cm/sec, Pressurization Area 2 cm$^2$, Sensitivity: 2 (Force Sensor 200 g/10 v), and Compression Weighting: 50 gf/cm$^2$. Then, using a correlation chart of pressure-deformation length, compressive resilience RC and work of compression WC were calculated. The higher compressive resilience (RC) is, the higher the recovery after the application of pressure is. On the other hand, the higher the work of compression (WC) is, the easier the application of pressure is.

(Sensory Test)

Two groups of disposable diaper samples were prepared for this sensory test, while each group includes 20 samples. These samples were the same except the absorbent structures, which were formed according to the Test example 18 and the Test example 20 for the two groups, respectively. Then, in each group, the samples are divided into two types. In the first type, each diaper was not compressed after it was produced, while in the second type, each diaper was compressed in the same way before individual packing and after that it was unpacked for the test. Then, through visual and touch comparison, these samples were tested by 20 persons. Precisely, comparing with the conventional disposable diapers, when each sample was determined to be almost the same, its result became Δ while each sample was determined to have higher recovery and softer, its result became ○.

[Table 4]

INDUSTRIAL APPLICABILITY

The present invention can be applied to an absorbent articles such as disposable diapers, sanitary napkins, urine pads, incontinence pads or the like.

EXPLANATION OF REFERENCE

1 . . . tow, 10 . . . assembly of fibers, 11 . . . polymer dispersion box, 12 . . . suction drum, 13 . . . sheet, 14 to 16 . . . adhesive applicator, 50, 60, 70, 80, 90, 100, 110, 120, 130 . . . body fluid absorbent structure, 51 . . . surface sheet, 52 . . . body fluid permeable absorbent member, 52E . . . second sheet, 53A, 53B . . . body fluid retainable absorbent member, 54 . . . back sheet, 300E . . . concave groove, 310 . . . pants-type disposable diaper, 310A . . . tape-type disposable diaper, 312 . . . outer sheet, 312A . . . back sheet, 320 . . . absorbent body, 330 . . . top sheet, 340 . . . interposed sheet, 350 . . . absorbent element, 352 . . . filament, 352X . . . bale, 352Y . . . tow, 352Z . . . assembly of filaments, 354 . . . super absorbent polymer particle, 358 . . . covering sheet, 360, 360A . . . barrier cuff, 364 . . . barrier sheet, 370 . . . body fluid impermeable sheet, 372 . . . second body fluid impermeable sheet, 380 . . . holding sheet, 390 . . . super absorbent polymer particle dispersion means, 390A . . . shooting unit, 390a . . . casing, 390b . . . rotating drum, 390c . . . shutter drum, 392 . . . folding machine, 394, 398 . . . cutter, 402 . . . combining station, 404 . . . applicator for coating the adhesive, 410 . . . second opening apparatus, 410a . . . air jet, 410b . . . venturi chamber, 400 . . . turning means, 424 . . . pretension roll, 426A . . . first nip, 426B . . . second nip, 426C . . . third nip, 430 . . . fastening tape, e . . . emboss, H . . . adhesive point, R1 to R6 . . . roll, Z . . . super absorbent polymer dispersion zone.

The invention claimed is:

1. A body fluid absorbent article, which has a body fluid retainable absorbent member having a pair of side portions with side edges disposed under a face sheet and a body fluid permeable absorbent member having a pair of side portions with side edges interposed between said face sheet and said body fluid retainable absorbent member, comprising:

said body fluid permeable absorbent member including an assembly of fibers in tows, each fiber of which is a continuous cellulose acetate fiber having a fineness of 1 to 16 denier and a porosity in the permeable absorbent member of 60 to 85%;

said body fluid permeable absorbent member disposed only at a zone of said body fluid retainable absorbent member, which is a middle portion in the width direction of said body fluid retainable absorbent member;

gutters inwardly formed by embossed regions of high density on said body fluid retainable absorbent member along the longitudinal direction thereof at a portion on an upper surface of a layer thereof in the both side portions with respect to the respective both side edges of said body fluid permeable absorbent member and at the same time not covered with said body fluid permeable absorbent member, and the gutters are not formed on said body fluid retainable absorbent member at a portion located on the upper surface of the layer thereof and covered with said body fluid permeable absorbent member so that after body fluid is diffused through said body fluid permeable absorbent member, the gutters prevent body fluid from diffusing across the gutters towards the side edges of said body fluid retainable absorbent member;

said body fluid permeable absorbent member is disposed only at a zone of said body fluid retainable absorbent member, which is a middle portion in the width direction and at the same time, which is an intermediate portion in the longitudinal direction of said body fluid retainable absorbent member; and the gutters are inwardly formed by embossed regions of high density on the body fluid retainable absorbent member along the width direction of said body fluid retainable absorbent member at a portion on the upper surface of the layer thereof in back and front with respect to a back edge and a front edge of said body fluid permeable absorbent member, respectively, and at the same time not covered with said body fluid permeable absorbent member.

2. A body fluid absorbent article as defined in claim 1, wherein said body fluid retainable absorbent member is formed with said assembly of fibers in tows, super absorbent polymer dispersed in said assembly of fibers in tows and a liquid permeable sheet with which said assembly of fibers is wrapped.

3. A body fluid absorbent article as defined in claim 1, wherein binder is added to said assembly of fibers in tows in at least one of said body fluid retainable absorbent member and said body fluid permeable absorbent member.

4. A body fluid absorbent article as defined in claim 3, wherein by adding said binder, contacting portions of said fibers are adhered or fused in the form of at least one of a line and dot.

5. A body fluid absorbent article as defined in claim 4, wherein said assembly of fibers in tows comprises at least two zones being different in adhesion degree or fusion degree of said fibers by adjusting the added amount of binder.

6. A body fluid absorbent article as defined in claim 5, wherein, in said assembly of fibers in tows, the adhesion degree or fusion degree of said fibers at a middle portion in the width direction is stronger than the adhesion degrees or fusion degrees of said fibers at both side portions in the width direction by adjusting the added amount of binder to said middle portion so as to be larger than the added amount of binder to said both side portions.

7. A body fluid absorbent article as defined in claim 5, wherein, in said assembly of fibers in tows, the adhesion degrees or fusion degrees of the fibers at both side portions in the width direction are stronger than the adhesion degree or fusion degree of said fibers at a middle portion in the width direction by adjusting the added amount of binder to said both side portions so as to be larger than the added amount of binder to said middle portion.

8. A body fluid absorbent article as defined in claim 5, wherein, in said assembly of fibers in tows, the adhesion degrees or fusion degrees of said fibers at a portion near a top face and a portion near a bottom face are stronger than the adhesion degree or fusion degree of said fibers at an intermediate portion between the top face and the bottom face by adjusting the added amount of binder to said portion near the top face and to said portion near the bottom face so as to be larger than the added amount of binder to said intermediate portion.

9. A body fluid absorbent article as defined in claim 5, wherein, in said assembly of fibers in tows, the adhesion degrees or fusion degrees of said fibers at a portion near a top face and at a portion near a bottom face and at both side end portions on the cross section in the width direction are stronger than the adhesion degree or fusion degree of said fibers at a central portion by adjusting the added amount of binder to said portion near the top face and to said portion near the bottom face and to a pair of side end portions so as to be larger than the added amount of binder to said central portion.

10. A body fluid absorbent article as defined in claim 5, wherein, in the above assembly of fibers in tows, the adhesion degrees or fusion degrees of said fibers at a pair of side end portions on the cross section in the width direction are stronger than the adhesion degree or fusion degree of said fibers at a midway portion on the cross section in the width direction by adjusting the added amount of binder to said both side end portions so as to be larger than the added amount of binder to said midway portion.

11. A body fluid absorbent article as defined in claim 5, wherein, in said assembly of fibers in tows, the adhesion degree or fusion degree of said fibers at a midway portion on the cross section in the width direction is stronger than the adhesion degrees or fusion degrees of said fibers at a pair of side end portions on the cross section in the width direction by adjusting the added amount of binder to said midway portion so as to be larger than the added amount of binder to said both side end portions.

12. A body fluid absorbent article as defined in claim 1, wherein an absorbent member made of an absorbent material other than the tow is laminated on the under surface of said body fluid retainable absorbent member.

13. A body fluid absorbent article as defined in claim 12, wherein said absorbent material other than the tow comprises at least one of a pulp fiber, porous foam, a cotton fiber and a non-woven fabric.

14. A body fluid absorbent article as defined in claim 12, wherein embossing is carried out on said absorbent member made of said absorbent material other than the tow.

15. A body fluid absorbent article as defined in claim 1, wherein said body fluid retainable absorbent member has a compressive resilience RC of 40 to 60%.

16. A body fluid absorbent article as defined in claim 1, wherein the above body fluid retainable absorbent member has a work of compression WC of 4.0 to 10.0 gf·cm/cm$^2$.

17. A body fluid absorbent article as defined in claim 1, wherein said body fluid retainable absorbent member has a tow fiber density of 0.03 to 0.25 g/cm$^3$.

18. A body fluid absorbent article as defined in claim 1, wherein said body fluid retainable absorbent member has a basis weight of 30 to 300 g/m$^2$.

19. A body fluid absorbent article as defined in claim 1, wherein said body fluid retainable absorbent member has a mass of 1 to 15 g.

20. A body fluid absorbent article as defined in claim 1, wherein a body fluid diffusion sheet having a width smaller than that of said body fluid permeable absorbent member is interposed between said body fluid retainable absorbent member and said body fluid permeable absorbent member.

21. A body fluid absorbent article as defined in claim 20, wherein pressing is carried out on said body fluid diffusion sheet along at least the longitudinal direction of said body fluid retainable absorbent member.

22. A body fluid absorbent article as defined in claim 1, wherein a body fluid permeable absorbent sheet is interposed between said face sheet and said body fluid permeable absorbent member and the absorbent sheet has laterally extended portions extending beyond respective both side edges in the width direction of said body fluid permeable absorbent member and said gutters formed along the longitudinal direction are arranged to overlap with the laterally extended portions.

23. A body fluid absorbent article as defined in claim 1, wherein the material fiber of said assembly of fibers in tows has the cross section of a circle or an ellipse.

24. A body fluid absorbent article as defined in claim 1, wherein a holding sheet is provided on the back surface side of said body fluid retainable absorbent member.

25. A body fluid absorbent article as defined in claim 24, wherein said holding sheet is a non-woven fabric having a work of compression of 0.01 to 10.00 gf·cm/cm$^2$ and a compressive resilience of 10 to 100% according to KES test.

26. A body fluid absorbent article as defined in claim 1, wherein said body fluid retainable absorbent member has a thickness of 0.1 to 1 cm.

27. A body fluid absorbent article as defined in claim 1, wherein said body fluid permeable absorbent member is disposed only at a zone of said body fluid retainable member, which is a middle portion in the width direction and at the same time, which is an intermediate portion in the longitudinal direction of said body fluid retainable member while said body fluid permeable absorbent member is wrapped with crepe paper.

* * * * *

UNITED STATES PATENT AND TRADEMARK OFFICE
CERTIFICATE OF CORRECTION

| | |
|---|---|
| PATENT NO. | : 8,466,334 B2 |
| APPLICATION NO. | : 11/631227 |
| DATED | : June 18, 2013 |
| INVENTOR(S) | : Tomonari Takeuchi et al. |

It is certified that error appears in the above-identified patent and that said Letters Patent is hereby corrected as shown below:

Please delete the notice that this patent is subject to a terminal disclaimer.

"(*) Notice: This patent is subject to a terminal disclaimer."

Signed and Sealed this
Third Day of September, 2013

Teresa Stanek Rea
*Acting Director of the United States Patent and Trademark Office*